(12) United States Patent
Iwamoto et al.

(10) Patent No.: US 7,247,705 B2
(45) Date of Patent: Jul. 24, 2007

(54) PROTEINS HAVING GLUCOSE TRANSPORTER ACTIVITY

(75) Inventors: Keiji Iwamoto, Tsukuba (JP); Nozomi Katayama, Tsukuba (JP); Mihoko Kawamura, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 588 days.

(21) Appl. No.: 10/451,822

(22) PCT Filed: Dec. 27, 2001

(86) PCT No.: PCT/JP01/11557

§ 371 (c)(1),
(2), (4) Date: Jun. 25, 2003

(87) PCT Pub. No.: WO02/053738

PCT Pub. Date: Jul. 11, 2002

(65) Prior Publication Data

US 2004/0053397 A1    Mar. 18, 2004

(30) Foreign Application Priority Data

Dec. 28, 2000  (JP) ............................. 2000-403078
Jun. 27, 2001  (JP) ............................. 2001-195467

(51) Int. Cl.
*C07K 14/00*  (2006.01)
*A61K 38/17*  (2006.01)

(52) U.S. Cl. ........................................ 530/350; 514/12

(58) Field of Classification Search ...................... None
See application file for complete search history.

(56) References Cited

U.S. PATENT DOCUMENTS

2005/0196754 A1*  9/2005  Drmanac et al. ............... 435/6

FOREIGN PATENT DOCUMENTS

WO     WO 00/18918     4/2000

OTHER PUBLICATIONS

Database EMBL: Nov. 24, 2000; XP002305383; Database accession No. AL109659/ the N-terminal part of the encoded protein of accession No. Q9NPZ7 (TrEMBL) is 100% identical to SEQ ID. No. 1 in a 68 amino acids overlap.
David G. Wang, et al., "Large-Scale Identification, Mapping, and Genotyping of Single-Nucleotide Polymorphisms in the Human Genome", Science, (1998), pp. 1077-1082, vol. 280.
Jason T. Lam, et al., "Missense Mutations in SGLT1 Cause Glucose-Galactose Malabsorption by Trafficking Defects", Biochimica et Biophysia Acta, (1999), pp. 297-303, vol. 1453, No. 2.
Kenji Tsujihara, "Na+-Glucose Cotransporter (SGLT) Inhibitors as Antidiabetic Agents. 4. Synthesis and Pharmacological Properties of 4'-Dehydroxyphlorizin Derivatives Substituted on the B Ring", Journal of Medicinal Chemistry, (1999), pp. 5311-5324, vol. 42, No. 26.
Tarpey, et al. "Amino acid sequence and the cellular location of the $Na^+$-dependent D-glucose symporters (SGLT1) inthe ovine enterocyte and the parotid acinar cell" BIOCHEM J 312:293-300 (1995).
Ana M. Pajor, "Sequence of aputative transporter from rabbit kidney related to the $Na^+$/glucose cotransporter gene family" Biochem. Biophys. Acta 1194(2): 349-351 (1994).
Turk, et al. Structure of the Human $Na^+$/Glucose Cotransporter Gene SGLT1 J. Biol. Chem. 269(21): 15204-15209 (1994).
Yang, et al. "Expression characteristics and relevance of sodium glucose cotransporter-1 in mammalian renal tubulogenesis" Am. J. Physiol. Renal Physiol. 279(4): F765-777 (2000).
Oku, et al. "T-1095, an Inhibitor of Renal $Na^+$-Glucose Cotransporters, May Provide a Novel Approach to Treating Diabetes" DIABETES 48: 1794-1800 (1999).
C.I. Cheeseman, "Upregulation of SGLT-1 Transport Activity in Rat Jejunum Induced by GLP-2 Infusion in vivo" Am. J. Physiol. 273: R1965-1971 (1997).
Nippon Rinsho (Japan Clinical), 55: 59-64 (1997), Extra Volume "Diabetes 1".

* cited by examiner

*Primary Examiner*—Ruixiang Li
(74) *Attorney, Agent, or Firm*—Edwards Angell Palmer & Dodge LLP; David G. Conlin; Lisa Swiszcz Hazzard

(57) ABSTRACT

The present invention provides proteins having the $Na^+$/glucose transporter activity, DNAs encoding the proteins, a method of screening for a compound enhancing or inhibiting the activity of the proteins, and compounds obtained by the screening method. The proteins having the same or substantially the same amino acid sequence as the amino acid sequence represented by SEQ ID NO: 1, 15 or 26 are useful as a diagnostic marker for a disease such as diabetes. The compounds enhancing or inhibiting the activity of the proteins, obtained the screening method using the proteins, can be used as a prophylactic and/or therapeutic agent for a disease such as diabetes and hyperlipidemia.

4 Claims, 16 Drawing Sheets

Fig. 14

|       | 2300 | -1300 | -500 | -450 | +1 |
|-------|------|-------|------|------|-----|
| K1X1  | K1———————————————————————— X1 |
| K2X1  |      | K2———————————————— X1 |
| K3X1  |      |       |      | K3———— X1 |
| K1X2  | K1————————————————— X2 |
| K2X2  |      | K2———— X2 |

PROTEINS HAVING GLUCOSE TRANSPORTER ACTIVITY

This application is the National Phase filing of International Patent Application No. PCT/JP01/11557, filed 27 Dec. 2001.

TECHNICAL FIELD

The present invention provides proteins having the $Na^+$/glucose transporter activity (SGLT homologs), DNAs encoding the proteins, single nucleotide polymorphisms (SNPs) of the DNAs, a method of screening for a compound promoting or inhibiting the activity of the proteins, and compounds obtained by the screening method.

BACKGROUND ART

A membrane protein called glucose transporter is required on the cell membrane to move glucose across the cell membrane from the outside into the inside, and vice versa.

The glucose transporter is divided into two major classes; one is a passive transporter or the facilitated diffusion-type glucose transporter (GLUT), and the other is an active transporter or the Na+/glucose transporter (SGLT), which transports glucose against its concentration gradient through the coupling with Na+ ion transport. There are 8 GLUT isoforms, which have a common structure having a molecular weight of about 50000 and 12 transmembrane spans.

SGLTs have a common structure having a molecular weight of about 75000 and 14 transmembrane spans.

The functions and expression sites of SGLTs 1 and 2 are outlined in Nippon Rinsho (Japanese Clinical) 55, extra number, Diabetes I, p. 59-64, 1997.

The human SGLT1 is expressed specifically in small intestine and kidney, and has a high affinity to glucose and a low transport activity, while the human SGLT2 is expressed specifically in kidney, and has a low affinity to glucose and a high transport activity. SGLTs have functions of absorbing glucose in small intestine and reabsorbing glucose in kidney, which has been excreted into the urine.

It is shown in a diabetes model rat that in consequence of inhibiting glucose reabsorption in kidney by inhibiting SGLT, glucose is excreted in the urine to decrease the blood glucose level (Diabetes 48: 1794-1800, 1999).

Until now, it has been considered that the passive transporter GLUT2 is primarily expressed in pancreatic beta cells and liver cells. GLUT2 is characterized by a low affinity to glucose and a high maximal transport activity. In pancreatic beta cells, GLUT2 is considered to take in glucose in a blood glucose level-dependent manner and function as glucose sensor along with glucokinase for the glucose level-dependent insulin secretion. In liver cells, GLUT2 is considered to function as glucose transporter to take blood glucose into the cells against the glucose concentration gradient across the cell membrane at high blood glucose level after a meal, and to release glucose into the bloodstream, which is produced intracelluarly through glycogenolysis or gluconeogenesis on an empty stomach.

It is reported that in samll intestine cells, human SGLT1 is moved from the cytoplasma to the cell membrane through the action of gastrointestinal hormone GLP-2, resulting in 3-fold increase in the glucose uptake activity (Am. J. Phsiol. 273, R1965-R1971, 1997).

The currently used insulin secretagogue (SU) closes $K_{ATP}$-channel in pancreatic beta cells to force the cells to secrete insulin irrespective of the blood glucose level. Accordingly, it is difficult to control the blood glucose level with SU, bringing about side effects, such as hypoglycemia, obesity through excessive insulin secretion. A phenomenon called secondary SU failure occurs, in which SU become ineffective after 10-year administration on average. This failure is considered due to fatigue of the pancreatic beta cells.

Therefore, it can be expected that activation of SGLT homolog function may enhance glucose uptake into pancreatic beta cells, and then the blood glucose-dependent insulin secretion. In addition, an activator of SGLT function is expected to cause no side effects, which the currently used insulin secretagogue (SU) shows.

In liver cells, GLUT2 releases glucose from liver into the bloodstream on an empty stomach, but a SGLT homolog is considered to enhance glucose uptake from blood into liver in spite of glucose concentration gradient across the cell membrane. Therefore, it can be expected to prevent glucose release from liver into blood, and thus a high blood glucose level on an empty stomach in a diabetes patient without occurrence of side effects such as hypoglycemia Furthermore, an inhibitor of SGLT is capable of lowering blood glucose level by inhibiting glucose reabsorption in kidney, and thus is expected to prevent fat synthesis by reducing glucose uptake into liver.

DISCLOSURE OF THE INVENTION

We intensively studied to solve the aforementioned problem, and finally found novel Na+/glucose transporter proteins (human SGLT homolog, mouse SGLT homolog, and rat SGLT homolog). The human SGLT homolog shows as high as 52% homology to human SGLT1, 52% homology to human SGLT2, 53% homology to mouse SGLT1, 51% homology to mouse SGLT2, 52% homology to rat SGLT1 and 51% homology to rat SGLT2 in respect of the amino acid sequence. The mouse SGLT homolog shows as high as 52% homology to human SGLT1, 52% homology to human SGLT2, 53% homology to mouse SGLT1, 50% homology to mouse SGLT2, 52% homology to rat SGLT1 and 50% homology to rat SGLT2 in respect of the amino acid sequence. The rat SGLT homolog shows as high as 52% homology to human SGLT1, 52% homology to human SGLT2, 53% homology to mouse SGLT1, 49% homology to mouse SGLT2, 52% homology to rat SGLT1 and 48% homology to rat SGLT2 in respect of the amino acid sequence. All of the human, mouse and rat SGLTs have the 14-transmembran-span structure, and may function as an active glucose transporter. The distribution of the expressed human SGLT homolog is different from those of human SGLT 1 and 2, and the human SGLT homolog is expressed the most highly in pancreas and liver. The rat SGLT homolog is highly expressed in kidney, and the rat SGLT homolog is highly expressed in smooth muscle and kidney.

As a method to activate the SGLT homolog, for example, it is possible to increase its expression level through activation of the promoter for the SGLT homolog, or stabilization of mRNA of the homolog. In addition, it is also possible to increase the number of SGLT homolog working on the cell membrane by moving the SGLT homolog from the cytoplasm to the membrane surface.

A further study based on these findings made us achieve the invention.

The invention provides:

(1) A protein comprising the same or substantially the same amino acid sequence as the amino acid sequence shown by SEQ ID NO: 1, or a salt thereof.

(2) The protein according to (1), which comprises the amino acid sequence shown by SEQ ID NO: 1, or a salt thereof.

(3) A protein comprising the same or substantially the same amino acid sequence as the amino acid sequence shown by SEQ ID NO: 15 or 26, or a salt thereof.

(4) The protein according to (3), which comprises the amino acid sequence shown by SEQ ID NO: 15 or 26, or a salt thereof.

(5) A partial peptide of the protein according to (1), or a salt thereof.

(6) A partial peptide of the protein according to (3), or a salt thereof.

(7) A DNA comprising a DNA encoding the protein according to (1) or the partial peptide according to (5).

(8) A DNA comprising a DNA encoding the protein according to (3) or the partial peptide according to (6).

(9) The DNA according to (7), which has the base sequence shown by SEQ ID NO: 2.

(10) The DNA according to (7), which has the base sequence shown by SEQ ID NO: 7.

(11) The DNA according to (8), which has the base sequence shown by SEQ ID NO: 16 or 27.

(12) A recombinant vector comprising the DNA according to (7).

(13) A recombinant vector comprising the DNA according to (8).

(14) A transformant transformed by the recombinant vector according to (12).

(15) A transformant transformed by the recombinant vector according to (13).

(16) A method of producing the protein according to (1), the partial peptide according to (5) or a salt thereof, which comprises culturing the transformant according to (14) to express and accumulate the protein according to (1) or the partial peptide according to (5); and collecting it.

(17) A method of producing the protein according to (3), the partial peptide according to (6) or a salt thereof, which comprises culturing the transformant according to (15) to express and accumulate the protein according to (3) or the partial peptide according to (6); and collecting it.

(18) A pharmaceutical composition comprising the protein according to (1), the partial peptide according to (5) or a salt thereof.

(19) A pharmaceutical composition comprising the protein according to (3), the partial peptide according to (6) or a salt thereof.

(20) A pharmaceutical composition comprising the DNA according to (7).

(21) A pharmaceutical composition comprising the DNA according to (8).

(22) A diagnostic agent comprising a polynucleotide comprising a polynucleotide encoding the protein according to (1) or (3), or the partial peptide according to (5) or (6).

(23) An antibody to the protein according to (1), the partial peptide according to (5) or a salt thereof.

(24) An antibody to the protein according to (3), the partial peptide according to (6) or a salt thereof.

(25) A diagnostic agent comprising the antibody according to (23) or (24).

(26) A method of screening for a compound or a salt thereof enhancing or inhibiting an activity of the protein according to (1), the partial peptide according to (5) or a salt thereof, which comprises using the protein according to (1), the partial peptide according to (5) or a salt thereof.

(27) A method of screening for a compound or a salt thereof enhancing or inhibiting an activity of the protein according to (3), the partial peptide according to (6) or a salt thereof, which comprises using the protein according to (3), the partial peptide according to (6) or a salt thereof.

(28) A method of screening for a compound or a salt thereof enhancing or inhibiting the expression of the protein according to (1) or (3) or the partial peptide according to (5) or (6), which comprises using a transformant transformed by a recombinant vector comprising a DNA having a reporter gene downstream of a promoter for the DNA according to (7) or (8).

(29) A kit for screening for a compound or a salt thereof enhancing or inhibiting an activity of the protein according to (1), the partial peptide according to (5) or a salt thereof, which comprises the protein according to (1), the partial peptide according to (5) or a salt thereof.

(30) A kit for screening for a compound or a salt thereof enhancing or inhibiting an activity of the protein according to (3), the partial peptide according to (6) or a salt thereof, which comprises the protein according to (3), the partial peptide according to (6) or a salt thereof.

(31) A compound or a salt thereof enhancing the activity of the protein according to (1), the partial peptide according to (5) or a salt thereof, which is obtained by the screening method according to (26) or the screening kit according to (29).

(32) A compound or a salt thereof enhancing the activity of the protein according to (3), the partial peptide according to (6) or a salt thereof, which is obtained by the screening method according to (27) or the screening kit according to (30).

(33) A compound or a salt thereof inhibiting the activity of the protein according to (1), the partial peptide according to (5) or a salt thereof, which is obtained by the screening method according to (26) or the screening kit according to (29).

(34) A compound or a salt thereof inhibiting the activity of the protein according to (3), the partial peptide according to (6) or a salt thereof, which is obtained by the screening method according to (27) or the screening kit according to (30).

(35) A pharmaceutical composition comprising a compound or a salt thereof enhancing the activity of the protein according to (1), the partial peptide according to (5) or a salt thereof, which is obtained by the screening method according to (26) or the screening kit according to (29).

(36) A pharmaceutical composition comprising a compound or a salt thereof enhancing the activity of the protein according to (3), the partial peptide according to (6) or a salt thereof, which is obtained by the screening method according to (27) or the screening kit according to (30).

(37) A pharmaceutical composition comprising a compound or a salt thereof inhibiting the activity of the protein according to (1), the partial peptide according to (5) or a salt thereof, which is obtained by the screening method according to (26) or the screening kit according to (29).

(38) A pharmaceutical composition comprising a compound or a salt thereof inhibiting the activity of the protein according to (3), the partial peptide according to (6) or a salt thereof, which is obtained by the screening method according to (27) or the screening kit according to (30).

(39) The pharmaceutical composition according to (18) or (20), which is a preventive and/or therapeutic agent for diabetes.

(40) The pharmaceutical composition according to (19) or (21), which is a preventive and/or therapeutic agent for diabetes.

(41) The pharmaceutical composition according to (35), which is a preventive and/or therapeutic agent for diabetes.

(42) The pharmaceutical composition according to (36), which is a preventive and/or therapeutic agent for diabetes.

(43) The pharmaceutical composition according to (37), which is a preventive and/or therapeutic agent for hyperlipidemia.

(44) The pharmaceutical composition according to (38), which is a preventive and/or therapeutic agent for hyperlipidemia.

(45) The diagnostic agent according to (22) or (25), which is useful for diabetes or hyperlipidemia.

(46) A method of diagnosing diabetes or hyperlipidemia, which comprises using a polynucleotide comprising a polynucleotide encoding the protein according to (1) or (3), or the partial peptide according to (5) or (6).

(47) A method of diagnosing diabetes or hyperlipidemia, which comprises using the antibody according to (23) or (24).

(48) A method of preventing and/or treating diabetes in a mammal, which comprises administering an effective amount of the compound according to (31) or (32) or a salt thereof to the mammal.

(49) A method of preventing and/or treating hyperlipidemia in a mammal, which comprises administering an effective amount of the compound according to (33) or (34) or a salt thereof to the mammal.

(50) A use of the compound according to (31) or (32) or a salt thereof for producing a preventive and/or therapeutic agent for diabetes.

(51) A use of the compound according to (33) or (34) or a salt thereof for producing a preventive and/or therapeutic agent for hyperlipidemia.

(52) Single nucleotide polymorphisms (SNPs) of a DNA comprising the base sequence shown by SEQ ID NO: 2, 16 or 27.

(53) The single nucleotide polymorphisms (SNPs) according to (52), which comprises the base sequence shown by SEQ ID NO: 40, 42 or 45.

(54) A protein comprising the amino acid sequence encoded by the single nucleotide polymorphisms (SNPs) according to (52), or a salt thereof.

(55) The protein or a salt thereof according to (54), which comprises the amino acid sequence shown by SEQ ID NO: 41, 43 or 46.

(56) A DNA comprising the base sequence shown by SEQ ID NO: 51.

(57) Single nucleotide polymorphisms (SNPs) of a DNA comprising the base sequence shown by SEQ ID NO: 51.

(58) The single nucleotide polymorphisms (SNPs) according to (57), which comprises the base sequence shown by SEQ ID NO: 54, 55 or 56.

(59) A recombinant vector comprising the single nucleotide polymorphisms (SNPs) according to (52).

(60) A recombinant vector comprising the DNA according to (56) or the single nucleotide polymorphisms (SNPs) according to (57).

(61) A transformant transformed by the recombinant vector according to (59).

(62) A transformant transformed by the recombinant vector according to (60).

(63) A method of producing the protein according to (54) or a salt thereof, which comprises culturing the transformant according to (61) to express and accumulate the protein according to (54); and collecting it.

(64) A pharmaceutical composition comprising the single nucleotide polymorphisms (SNPs) according to (52).

(65) A pharmaceutical composition comprising the protein according to (54) or a salt thereof.

(66) The pharmaceutical composition according to (64) or (65), which is a preventive and/or therapeutic agent for diabetes or hyperlipidemia

(67) A diagnostic agent comprising the single nucleotide polymorphisms (SNPs) according to (52) or (57).

(68) The diagnostic agent according to (67), further comprising a DNA comprising the base sequence shown by SEQ ID NO: 2, 16, 27 or 51, or a part of the DNA.

(69) The diagnostic agent according to (67), which is useful for diabetes or hyperlipidemia.

(70) A method of diagnosing diabetes or hyperlipidemia, which comprises analyzing the single nucleotide polymorphisms (SNPs) according to (52) or (57).

BRIEF DESCRIPTION OF THE DRAWINGS

FIG. 14 shows mutants having a deletion in the upstream region of the human SGLT homolog gene.

Figure 1:
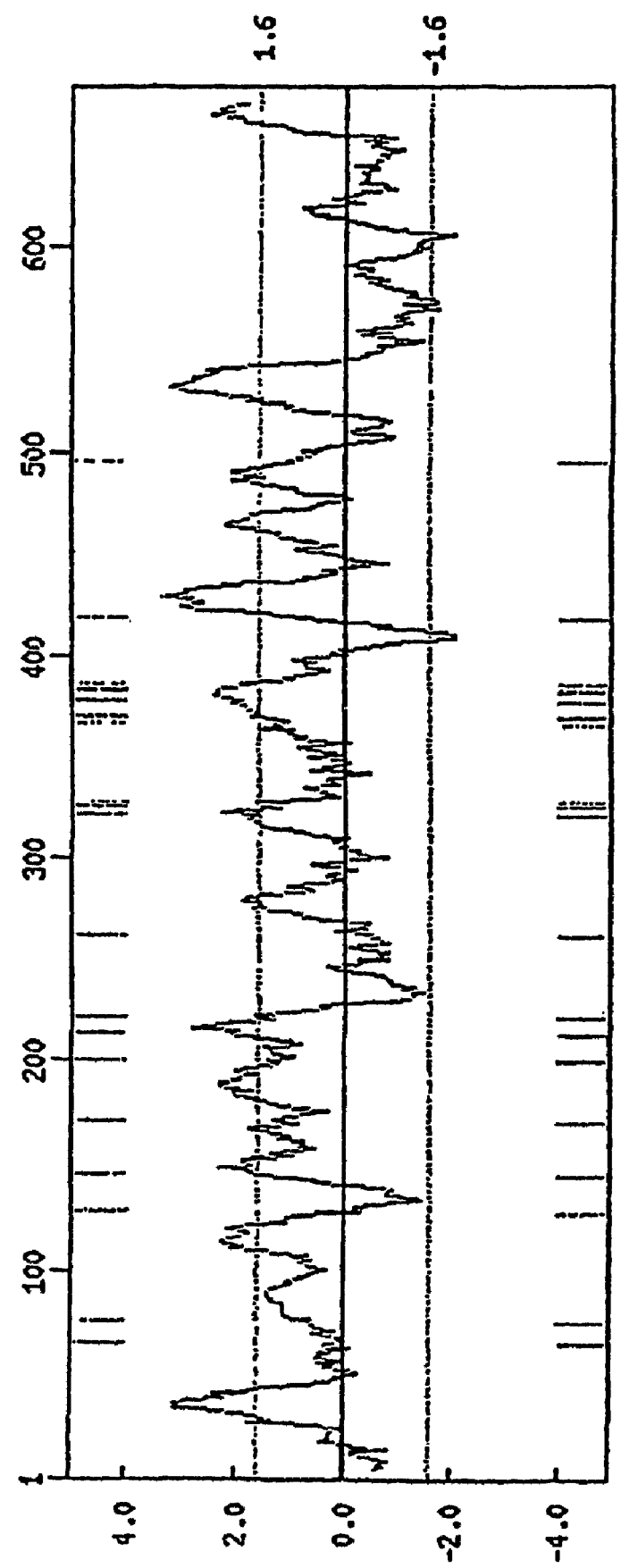
FIG. 1 shows the hydropathy plot of the human SGLT homolog.

The proteins used in the invention comprising the same or substantially the same amino acid sequence as the amino acid sequence represented by SEQ ID NO: 1, 15 or 26 (hereinafter may be referred to the proteins of the invention or the proteins used in the invention) may be derived from any cells of a human or other warm-blooded animals (e.g. guinea pig, rat, mouse, chicken, rabbit, swine, sheep, bovine, monkey) (e.g. hepatocytes, splenocytes, nerve cells, glial cells, cells of pancreas, bone marrow cells, mesangial cells, Langerhans' cells, epidermic cells, epithelial cells, beaker cell, endothelial cells, smooth muscle cells, fibroblasts, fibrocytes, myocytes, fat cells, immune cells (e.g. macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells); or any tissues where such cells are present, such as brain or any brain regions (e.g. olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g. large intestine and small intestine), blood vessel, heart, thymus, spleen, submandibular gland, peripheral blood, prostate, testis, ovary, placenta, uterus, bone, joint, skeletal muscle, etc.; the proteins may also be synthetic proteins.

The amino acid sequence which is substantially the same as the amino acid sequence represented by SEQ ID NO: 1, 15 or 26 includes amino acid sequences having at least about 60% homology, preferably at least about 70% homology, and more preferably at least about 80% homology, even more preferably at least about 90% homology, and most preferably at least about 95% homology to the amino acid sequence represented by SEQ ID NO: 1, 15 or 26.

As the protein comprising substantially the same amino acid sequence as the amino acid sequence represented by SEQ ID NO: 1, 15 or 26, preferred is the protein comprising substantially the same amino acid sequence as the amino acid sequences represented by SEQ ID NO: 1, 15 or 26 and having substantially the same activity in quality as that of the protein comprising the amino acid sequence represented by SEQ ID NO: 1, 15 or 26.

Such substantially the same activity in quality is exemplified by the active glucose transport activity. "Substantially the same in quality" means that the activity is identical in quality (e.g., physiologically or pharmacologically). Thus, it is preferable that the active glucose transport activity shows the same level (e.g. about 0.01 to 100 folds, preferably about 0.1 to 10 folds, more preferably about 0.5 to 2 folds), but any quantitative factors such as the activity level and the molecular weight may be different.

The active glucose transport activity can be measured according to a known method, for example, the method described in "Cloning and functional expression of an SGLT-1-like protein from the *Xenopus laevis* intestine", Am. J. Phisiol. 276: G1251-G1259, 1999 or a modification thereof.

The proteins of the invention also include so-called muteins such as proteins comprising (i) an amino acid sequence represented by SEQ ID NO: 1, 15 or 26, in which one or more (preferably 1 to 30, more preferably 1 to 10, and even more preferably 1 to 5) amino acids are deleted; (ii) an amino acid sequence represented by SEQ ID NO: 1, 15 or 26, to which one or more (preferably 1 to 30, more preferably 1 to 10, and even more preferably 1 to 5) amino acids are added; (iii) an amino acid sequence represented by SEQ ID NO: 1, 15 or 26, into which one or more (preferably 1 to 30, more preferably 1 to 10, and even more preferably 1 to 5) amino acids are inserted, (iv) an amino acid sequence represented by SEQ ID NO: 1, 15 or 26, in which one or more (preferably 1 to 30, more preferably 1 to 10, and even more preferably 1 to 5) amino acids are substituted by other amino acids; and (v) a combination of the above amino acid sequences.

When such an insertion, deletion or substitution is made in the amino acid sequences as described above, there is no special limitation to positions for the insertion, deletion or substitution.

In the present specification, proteins are shown in accordance with the conventional way for peptides with the N-terminal (amino terminal) on the left side and the C-terminal (carboxyl terminal) on the right side. The proteins of the invention including the protein comprising the amino acid sequence shown by SEQ ID NO: 1, 15 or 26, may have their C-terminals in a form of a carboxyl group (—COOH), a carboxylate (—COO-), an amide (—CONH$_2$) or an ester (—COOR).

Examples of the ester group shown by R include a $C_{1-6}$ alkyl group such as methyl, ethyl, n-propyl, isopropyl, n-butyl; a $C_{3-8}$ cycloalkyl group such as cyclopentyl, cyclohexyl; a $C_{6-12}$ aryl group such as pbenyl, α-naphthyl; a $C_{7-14}$ aralkyl such as a phenyl-$C_{1-2}$ alkyl group, e.g. benzyl, phenethyl, and an α-naphthyl-$C_{1-2}$ alkyl group, e.g. α-naphthylmethyl; pivaloyloxymethyl, and the like.

When the protein of the invention contains a carboxyl group (or a carboxylate) at a position other than the C-terminal, it may be amidated or esterified. Such an amide or ester is also included within the protein of the invention. This ester group may be the same as the above-mentioned C-terminal ester group.

Furthermore, examples of the protein of the invention include variants of the above proteins, wherein the amino group at the N-terminal (e.g. methionine residue) of the protein is protected with a protecting group (e.g. $C_{1-6}$ acyl such as $C_{1-6}$ alkanoyl, e.g. formyl, acetyl); those wherein the N-terminal glutamyl group newly formed after cleavage in vivo is pyroglutaminated; those wherein a substituent (e.g. —OH, —SH, amino group, imidazole group, indole group, guanidino group) on the side chain of an amino acid in the molecule is protected with a suitable protecting group (e.g. $C_{1-6}$ acyl such as $C_{1-6}$ alkanoyl, e.g. formyl, acetyl), or conjugated proteins such as glycoproteins having sugar chains.

Specifically, the protein of the invention includes the human pancreas-derived protein having the amino acid sequence represented by SEQ ID NO: 1, the mouse kidney-derived protein having the amino acid sequence represented by SEQ ID NO: 15, and the rat kidney-derived protein having the amino acid sequence represented by SEQ ID NO: 26.

The partial peptide of the protein of the invention may be any partial peptides of the protein of the invention described above, preferably those having a property similar to that of the protein of the invention described above.

For example, employed are peptides having partial sequences of at least 20, preferably at least 50, more preferably at least 70, much more preferably at least 100 and most preferably at least 200 amino acids in the constitutional amino acid sequence of the protein of the invention.

In the partial peptide of the invention, (i) one or more (preferably 1 to 10, more preferably 1 to 5) amino acids in the amino acid sequence of the partial peptide may be deleted; (ii) one or more (preferably 1 to 20, more preferably 1 to 10, even more preferably 1 to 5) amino acids may be added to the amino acid sequence; (iii) one or more (preferably 1 to 20, more preferably 1 to 10, even more preferably 1 to 5) amino acids may be inserted into the amino acid sequence; or (iv) one or more (preferably 1 to 10, more preferably several, even more preferably 1 to 5) amino acids in the amino acid sequence may be substituted by other amino acids.

The partial peptide of the invention preferably includes a peptide comprising the sequence from aa176 to aa201 or from aa471 to aa491 in the amino acid sequence represented by SEQ ID NO: 1; a peptide comprising the sequence from aa172 to aa197 or from aa467 to aa487 in the amino acid sequence represented by SEQ ID NO: 15; and a peptide comprising the sequence from aa175 to aa200 or from aa470 to aa490 in the amino acid sequence represented by SEQ ID NO: 26.

The partial peptide of the invention may have the C-terminal in a form of carboxyl (—COOH,) (—COO⁻,) amide (—CONH₂,) or ester (—COOR).

The partial peptide of the invention includes, as well as the aforementioned protein of the invention, variants which have a carboxyl (or carboxylate) at a position other than the C-terminal; those wherein the amino group at the N-terminal (e.g. methionine residue) of the protein is protected with a protecting group; those wherein the N-terminal glutamyl group newly formed after cleavage in vivo is pyroglutaminated; those wherein a substituent on the side chain of an amino acid in the molecule is protected with a suitable protecting group, or conjugated proteins such as glycoproteins having sugar chains.

The partial peptide of the invention can be used as an antigen for producing an antibody thereto.

To produce the antibody of the invention as described below, for example, used are a peptide comprising the sequence from aa261 to aa275, from aa399 to aa417, or from aa500 to aa649 in the amino acid sequence represented by SEQ ID NO: 1; a peptide comprising the sequence from aa257 to aa271, from aa395 to aa413 or from aa496 to aa645 in the amino acid sequence represented by SEQ ID NO: 15; and a peptide comprising the sequence from aa260 to aa274, from aa398 to aa416 or from aa499 to aa648 in the amino acid sequence represented by SEQ ID NO: 26.

The salt of the protein or the partial peptide of the invention may be a salt with physiologically acceptable acids (e.g. inorganic acids, organic acids) or bases (e.g. alkaline metals), and physiologically acceptable acid addition salts are particularly preferred. Examples of such salts are salts with inorganic acids (e.g. hydrochloric acid, phosphoric acid, hydrobromic acid, sulfuric acid), and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

The protein of the invention, the partial peptide or the salt thereof may be produced by a known method for protein purification from human or other warm-blooded animal tissues or cells described above, or may be produced by culturing a transformant containing a DNA encoding the protein, or may also be produced by the peptide synthesis method described below.

To produce the protein of the invention, the partial peptide or the salt thereof from human or other warm-blooded animal tissues or cells, after these tissues or cells are homogenized and extracted with an acid, the protein is isolated or purified from the obtained extract by a combination of chromatography techniques such as reversed phase chromatography, ion exchange chromatography, and the like.

To synthesize the protein of the invention, the partial peptide thereof, the salt thereof, or the amide thereof, commercially available resins for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin. Using these resins, amino acids in which α-amino groups and functional groups on the side chains are appropriately protected are condensed on the resin in the order of the sequence of the objective protein according to various condensation methods publicly known. At the end of the reaction, the protein or the partial peptide is excised from the resin and at the same time, the protecting groups are removed. Then, intramolecular disulfide bond-forming reaction is performed in a highly diluted solution to obtain the objective protein or partial peptide, or an amide thereof.

For condensation of the protected amino acids described above, a variety of activation reagents for protein synthesis may be used, but carbodiimides are particularly preferably employed. Examples of such carbodiimides include DCC, N,N'-diisopropylcarbodiimide, N-ethyl-N'-(3-dimethylaminopropyl)carbodiimide. For activation by these reagents, the protected amino acids in combination with a racemization inhibitor (e.g. HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents used to activate the protected amino acids or condense with the resin may be chosen from solvents that are known to be usable for protein condensation reactions. Acid amides such as N,N-dimethylformamide, N,N-dimethylacetamide, N-methylpyrrolidone; halogenated hydrocarbons such as methylene chloride, chloroform; alcohols such as trifluoroethanol; sulfoxides such as dimethylsulfoxide; ethers such as pyridine, dioxane, tetrahydrofuran; nitriles such as acetonitrile, propionitrile; esters such as methyl acetate, ethyl acetate; and appropriate mixtures of these solvents are usable. The reaction temperature is appropriately chosen from the range known to be applicable to protein binding reactions and is usually selected in the range of about −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect an amino group in the starting material include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc.

A carboxyl group can be protected by e.g. alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl), aralkyl esterification (e.g. esterification in the form of benzyl ester, 4-nitrobenzyl ester, 4-methoxybenzyl ester, 4-chlorobenzyl ester, benzhydryl ester), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group.

Examples of groups for protecting the phenolic hydroxyl group of tyrosine include Bzl, $Cl_2$-Bzl, 2-nitrobenzyl, Br-Z, t-butyl.

Examples of groups used to protect the imidazole moiety of histidine include Tos, 4-methoxy-2,3,6-trimethylbenzenesulfonyl, DNP, benzyloxymethyl, Bum, Boc, Trt, Fmoc.

Examples of the activated carboxyl group in the starting material include the corresponding acid anhydrides, azides, activated esters [esters with alcohols (e.g. pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. As the activated amino group in the starting material, the corresponding phosphoric amide is employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of about −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups in the starting material, which should not be involved in the reaction, protecting groups, elimination of the protecting groups and activation of functional groups involved in the reaction may be appropriately selected from publicly known groups and publicly known means.

In another method for obtaining an amide of the protein or the partial peptide, for example, the α-carboxyl group of the carboxy terminal amino acid is first protected by amidation; the peptide (protein) chain is then extended to amino group for a desired length. Thereafter, the protein or the partial peptide in which only the protecting group of the N-terminal α-amino group has been eliminated from the protein or the partial peptide in which only the protecting group of the C-terminal carboxyl group has been eliminated are manufactured. The protein or the peptide is condensed in a mixture of the solvents described above. The details of the condensation reaction are the same as described above. After the protected protein or the peptide obtained by the condensation is purified, all the protecting groups are eliminated by the method described above to give the desired crude protein or peptide. This crude protein or peptide is purified by various known purification means. Lyophilization of the major fraction gives the desired amide of the protein or peptide.

To prepare the esterified protein or peptide, for example, the α-carboxyl group of the carboxy terminal amino acid is condensed with a desired alcohol to prepare the amino acid ester, which is then processed by procedure similar to the preparation of the amidated protein or peptide above to give the desired esterified protein or peptide.

The partial peptide of the invention or a salt thereof can be produced by publicly known methods for peptide synthesis, or by cleaving the protein of the invention with an appropriate peptidase. For the peptide synthesis methods, for example, either solid phase synthesis or liquid phase synthesis may be used. Thus, a partial peptide or amino acids that can construct the partial peptide of the invention can be condensed with the remaining part of the partial peptide of the invention. When the product contains protecting groups, these protecting groups are removed to give the desired peptide. Publicly known methods for condensation and elimination of the protecting groups are described in the following 1) to 5.)

1) M. Bodanszky & M. A. Ondetti: Peptide Synthesis, Interscience Publishers, New York (1966)

2) Schroeder & Luebke: The Peptide, Academic Press, New York (1965)

3) Nobuo Izumiya, et al.: Peptide Gosei-no-Kiso to Jikken (Basics and experiments of peptide synthesis), published by Maruzen Co. (1975)

4) Haruaki Yajima & Shunpei Sakakibara: Seikagaku Jikken Koza (Biochemical Experiment) 1, Tanpakushitsu no Kagaku (Chemistry of Proteins) IV, 205 (1977)

5) Haruaki Yajima ed.: Zoku Iyakuhin no Kaihatsu (A sequel to Development of Pharmaceuticals), Vol. 14, Peptide Synthesis, published by Hirokawa Shoten After completion of the reaction, the partial peptide of the invention can be purified or isolated by a combination of conventional purification methods such as solvent extraction, distillation, column chromatography, liquid chromatography and recrystallization to give the partial peptide of the invention. When the partial peptide obtained by the above methods is in a free form, it can be converted into an appropriate salt by a publicly known method; when the partial peptide is obtained in a salt form, it can be converted into a free form or a different salt form by the publicly known method.

The DNA encoding the protein of the invention may be any DNA comprising the base sequence encoding the above-mentioned protein of the invention. The DNA may be derived from a genome DNA, a genome DNA library, cDNAs derived from the aforementioned tissues and cells, a cDNA library derived from the aforementioned tissues and cells, or synthetic DNAs.

Vectors used for the libraries may be any one of bacteriophage, plasmid, cosmid, phagemid, and the like. In addition, the DNA can be amplified by reverse transcriptase polymerase chain reaction (hereinafter abbreviated as RT-PCR) from total RNA or mRNA fraction prepared from the above-mentioned cells or tissues.

The DNA encoding the protein of the invention may be any DNA comprising the base sequence represented by SEQ ID NO: 2, 7, 16 or 27; or any DNA hybridizable to the base sequence represented by SEQ ID NO: 2, 7, 16 or 27 under high stringent conditions and encoding a protein which has a property substantially equivalent to the property of the protein of the invention.

Examples of the DNA that is hybridizable to the base sequence represented by SEQ ID NO: 2 under high stringent conditions include DNAs comprising a base sequence with at least about 50% homology, preferably at least about 60% homology, more preferably at least about 70% homology, even more preferably at least about 80% homology, much more preferably at least about 90% homology, and most preferably at least about 95% homology to the base sequence represented by SEQ ID NO: 2.

Examples of the DNA that is hybridizable to the base sequence represented by SEQ ID NO: 7 under high stringent conditions include DNAs comprising a base sequence with at least about 50% homology, preferably at least about 60% homology, more preferably at least about 70% homology, even more preferably at least about 80% homology, much more preferably at least about 90% homology, and most preferably at least about 95% homology to the base sequence represented by SEQ ID NO: 7.

Examples of the DNA that is hybridizable to the base sequence represented by SEQ ID NO: 16 under high stringent conditions include DNAs comprising a base sequence with at least about 50% homology, preferably at least about 60% homology, more preferably at least about 70% homology, even more preferably at least about 80% homology, much more preferably at least about 90% homology, and most preferably at least about 95% homology to the base sequence represented by SEQ ID NO: 16.

Examples of the DNA that is hybridizable to the base sequence represented by SEQ ID NO: 27 under high stringent conditions include DNAs comprising a base sequence with at least about 50% homology, preferably at least about 60% homology, more preferably at least about 70% homology, even more preferably at least about 80% homology, much more preferably at least about 90% homology, and most preferably at least about 95% homology to the base sequence represented by SEQ ID NO: 27.

The hybridization can be carried out according to a known method or a modification thereof, for example, the method described in Molecular Cloning, 2nd Ed., J. Sambrook et al., Cold Spring Harbor Lab. Press, (1989). A commercially available library may also be used according to the instructions of the attached manufacturer's protocol. The hybridization can be carried out preferably under high stringent conditions.

The high stringent conditions used herein refer to, for example, a sodium concentration of about 19 to 40 mM, preferably about 19 to 20 mM and a temperature of about 50 to 70° C., preferably about 60 to 65° C. In particular, the hybridization condition in a sodium concentration of about 19 mM at a temperature of about 65° C. is most preferred.

More specifically, the DNA encoding the protein comprising the amino acid sequence represented by SEQ ID NO: 1 includes the DNA comprising the base sequence represented by SEQ ID NO: 2 or 7; the DNA encoding the protein comprising the amino acid sequence represented by SEQ ID NO: 15 includes the DNA comprising the base sequence represented by SEQ ID NO: 16; and the DNA encoding the protein comprising the amino acid sequence represented by SEQ ID NO: 26 includes the DNA comprising the base sequence represented by SEQ ID NO: 27.

The DNA encoding the partial peptide of the invention may be any DNA comprising the base sequence encoding the partial peptide of the invention described above. The DNA may be derived from any of genomic DNAs, genomic DNA library, cDNAs derived from the cells and tissues described above, cDNA library derived from the cells and tissues described above and synthetic DNAs.

The DNA encoding the partial peptide of the invention may be any DNA having a partial sequence of the DNA having the base sequence represented by SEQ ID NO: 2, 7, 16 or 27; or any DNA having a partial sequence of a DNA hybridizable to the base sequence represented by SEQ ID NO: 2, 7, 16 or 26 under high stringent conditions and encoding a protein which has an activity substantially equivalent to the activity of the protein of the invention.

The DNA that is hybridizable to the base sequence represented by SEQ ID NO: 2, 7, 16 or 27 is as defined above.

Methods for the hybridization and the high stringent conditions that can be used are the same as described above.

The single nucleotide polymorphisms (SNPs) of the DNA encoding the protein of the invention include the single nucleotide polymorphisms (SNPs) of the DNA comprising the base sequence represented by SEQ ID NO: 2, 16 or 27, and specifically the single nucleotide polymorphisms (SNPs) comprising the base sequence represented by SEQ ID NO: 40, 42 or 45.

Specifically, the proteins encoded by the single nucleotide polymorphisms (SNPs) of the invention include proteins comprising the amino acid sequence represented by SEQ ID NO: 41, 43 or 46.

The promoter for the DNA encoding the protein of the invention includes a DNA comprising the base sequence represented by SEQ ID NO: 51.

The single nucleotide polymorphisms (SNPs) of the DNA comprising the base sequence represented by SEQ ID NO: 51 include the single nucleotide polymorphisms (SNPs) comprising the base sequence represented by SEQ ID NO: 54, 55 or 56.

For cloning of the DNA completely encoding the protein of the invention or the partial peptide thereof (hereinafter sometimes collectively referred to as the protein of the invention in the following description of cloning and expression of the DNA encoding the proteins)(including the single nucleotide polymorphisms of the DNA), the DNA may be either amplified by PCR using synthetic DNA primers containing a part of the base sequence encoding the protein of the invention, or the DNA inserted into an appropriate vector can be selected by hybridization with a labeled DNA fragment or synthetic DNA that encodes a part or the entire region of the protein of the invention. The hybridization can be carried out according to a known method, for example, the method described in Molecular Cloning, 2nd Ed., J. Sambrook et al., Cold Spring Harbor Lab. Press, (1989). A commercially available library may also be used according to the instructions of the attached manufacturer's protocol.

Change of the base sequence of DNA can be conducted by the PCR method or other known methods such as the ODA-LA PCR method, the Gapped duplex method or the Kunkel method, or modifications thereof using publicly known kits such as Mutan™-super Express Km (TaKaRa) or Mutan™-K (TaKaRa).

The cloned DNA encoding the protein of the invention can be used as it is, depending upon purpose or, if desired, after digestion with a restriction enzyme or after addition of a linker thereto. The DNA may contain ATG as a translation initiation codon at the 5' end and TAA, TGA or TAG as a translation termination codon at the 3' end. These translation initiation and termination codons may also be added by using an appropriate synthetic DNA adapter.

The expression vector for the protein of the invention can be produced, for example, by (a) excising the desired DNA fragment from the DNA encoding the protein of the invention, (b) and then ligating the DNA fragment with an appropriate expression vector downstream a promoter in the vector.

Examples of the vector include plasmids derived form *E. coli* (e.g. pBR322, pBR325, pUC12, pUC13), plasmids derived from *Bacillus subtilis* (e.g. pUB110, pTP5, pC194), plasmids derived from yeast (e.g. pSH19, pSH15), bacteriophages such as λ phage, animal viruses such as retrovirus, vaccinia virus, baculovirus, as well as pA1-11, pXT1, pRc/CMV, pRc/RSV, pcDNAI/Neo.

The promoter used in the present invention may be any promoter if it matches well with a host to be used for gene expression. In the case of using animal cells as the host, examples of the promoter include SRα promoter, SV40 promoter, HIV/LTR promoter, CMV promoter, HSV-TK promoter.

Among them, CMV (cytomegalovirus) promoter or SRα promoter is preferably used. When *Escherichia* bacteria are used as the host, preferred examples of the promoter include trp promoter, lac promoter, recA promoter, λPL promoter, lpp promoter, and T7 promoter. When *Bacillus* bacteria are used as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin promoter and P10 promoter.

In addition to the foregoing examples, the expression vector may further optionally contain an enhancer, a splicing signal, a poly A addition signal, a selection marker, or SV40 replication origin (hereinafter sometimes abbreviated as SV40ori). Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), and neomycin resistant gene (hereinafter sometimes abbreviated as Neo, G418 resistance). In particular, when dhfr gene is used as the selection marker together with dhfr gene-deficient Chinese hamster cells, selection can also be made on thymidine-free medium.

If necessary, a signal sequence that matches with a host is added to the N-terminal of the protein of the invention. Examples of the signal sequence that can be used are Pho A signal sequence, OmpA signal sequence in case of using *Escherichia* bacteria as the host; α-amylase signal sequence, subtilisin signal sequence in case of using *Bacillus* bacteria as the host; MFα signal sequence, SUC2 signal sequence in case of using yeast as the host; and insulin signal sequence, α-interferon signal sequence, antibody molecule signal sequence in case of using animal cells as the host, respectively.

Using the vector comprising the DNA encoding the protein of the invention thus constructed, a transformant can be produced.

Examples of the host, which may be employed, are *Escherichia* bacteria, *Bacillus* bacteria, yeasts, insect cells, insects and animal cells.

Examples of *Escherichia* bacteria include *Escherichia coli* K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)).

Examples of *Bacillus* bacteria include *Bacillus subtilis* MI114 (Gene, 24 255 (1983)), 207-21 (Journal of Biochemistry, 95, 87 (1984)).

Examples of yeasts include *Saccharomyces cereviseae* AH22, AH22R⁻, NA87-11A, DKD-5D, 20B-12, *Schizosaccharomyces pombe* NCYC1913, NCYC2036, *Pichia pastoris* KM71.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from *Estigmena acrea*; and for the virus BmNPV, *Bombyx mori* N cell (BmN cell) is used. Examples of the Sf cell which can be used are Sf9 cell (ATCC CRL1711) and Sf21 cell (both cells are described in Vaughn, J. L. et al., In Vivo, 13, 213-217 (1977).

Examples of insects include a larva of *Bombyx mori* (Maeda et al., Nature, 315, 592, 1985).

Examples of animal cells include monkey cell COS-7, Vero, Chinese hamster cell CHO (hereinafter referred to as CHO cell), dhfr gene-deficient Chinese hamster cell CHO (hereinafter simply referred to as CHO (dhfr⁻) cell), mouse L cell, mouse AtT-20, mouse myeloma cell, rat GH 3, human FL cell.

*Escherichia* bacteria can be transformed, for example, by the method described in Proc. Natl. Acad. Sci. U.S.A., 69, 2110 (1972), Gene, 17, 107 (1982).

*Bacillus* bacteria can be transformed, for example, by the method described in Molecular & General Genetics, 168, 111 (1979).

Yeasts can be transformed, for example, by the method described in Methods in Enzymology, 194, 182-187 (1991) or Proc. Natl. Acad. Sci. U.S.A., 75 1929 (1978).

Insect cells or insects can be transformed, for example, according to the method described in Bio/Technology, 6, 47-55(1988).

Animal cells can be transformed, for example, according to the method described in Saibo Kogaku (Cell Engineering), extra issue 8, Shin Saibo Kogaku Jikken Protocol (New Cell Engineering Experimental Protocol), 263-267 (1995), published by Shujunsha, or Virology, 52, 456 (1973).

Thus, the transformant, which is transformed with the expression vector comprising the DNA encoding the protein, can be obtained.

When an *Escherichia* or *Bacillus* bacterium is used as the host, the transformant can be appropriately cultured in a liquid medium which contains materials required for growth of the transformant such as carbon sources, nitrogen sources, and inorganic materials. Examples of the carbon sources include glucose, dextrin, soluble starch, and sucrose. Examples of the nitrogen sources include inorganic or organic materials such as ammonium salts, nitrate salts, corn steep liquor, peptone, casein, meat extract, soybean cake, and potato extract. Examples of the inorganic materials are calcium chloride, sodium dihydrogenphosphate, and magnesium chloride. In addition, yeast extracts, vitamins, and growth-stimulating factors may also be added to the medium. Preferably, pH of the medium is adjusted to about 5 to 8.

A preferred example of the medium for culturing *Escherichia* bacteria is M9 medium supplemented with glucose and casamino acids (Miller, Journal of Experiments in Molecular Genetics, 431-433, Cold Spring Harbor Laboratory, New York, 1972). If necessary, a chemical such as 3β-indolylacrylic acid can be added to the medium thereby to increase the promoter efficiency.

When an *Escherichia* bacterium is used as the host, the transformant is usually cultured at about 15 to 43° C. for about 3 to 24 hours. If necessary, the culture may be aerated or agitated.

When a *Bacillus* bacterium is used as the host, the transformant is cultured generally at about 30 to 40° C. for about 6 to 24 hours. If necessary, the culture can be aerated or agitated.

When a yeast is used as the host, the medium for culturing the transformant may be Burkbolder's minimal medium (Bostian, K. L. et al., Proc. Natl. Acad. Sci. U.S.A., 77, 4505, 1980) or SD medium supplemented with 0.5% Casamino acids (Bitter, G. A. et al., Proc. Natl. Acad. Sci. U.S.A., 81, 5330, 1984). Preferably, pH of the medium is adjusted to about 5 to 8. In general, the transformant is cultured at about 20 to 35° C. for about 24 to 72 hours. If necessary, the culture can be aerated or agitated.

When an insect cell or insect is used as the host, the medium for culturing the transformant may be Grace's Insect Medium (Grace, T. C. C., Nature 195, 788 (1962)) to which an appropriate additive such as 10% inactivated bovine serum is added. Preferably, pH of the medium is adjusted to about 6.2 to 6.4. Generally, the transformant is cultured at about 27° C. for about 3 to 5 days and, if necessary, the culture can be aerated or agitated.

When an animal cell is used as the host, the medium for culturing the transformant may be MEM medium (Science, 122 501 (1952)), DMEM medium (Virology, 8, 396 (1959)), RPMI 1640 medium (The Journal of the American Medical Association, 199, 519 (1967)) or 199 medium (Proceeding of the Society for the Biological Medicine, 73, 1 (1950)), which contains about 5 to 20% fetal bovine serum. Preferably, pH of the medium is adjusted to about 6 to 8. The transformant is usually cultured at about 30 to 40° C. for about 15 to 60 hours and, if necessary, the culture can be aerated or agitated.

As described above, the protein of the invention can be produced intracelluarly, extracellularly, or on the cell membrane by the transformant.

The protein of the invention can be isolated or purified from the culture described above by the following procedures.

To extract the protein of the invention from the culture of bacteria or cells, after the culture is completed, the bacteria or cells are collected by a well known method and suspended in an appropriate buffer. The bacteria or cells are disrupted by a well known method such as ultrasonication, treatment with lysozyme or freeze-thaw cycling, and then subjected to the centrifugation or filtration to obtain the crude protein extract. The buffer may contain a protein denaturing agent such as urea or guanidine hydrochloride, or a surfactant such as Triton X-100™. When the protein of the invention is secreted into the culture broth, after the culture is completed, the supernatant can be separated and collected from the bacteria or cells by a well known method.

The protein of the invention contained in the supernatant or the extract thus obtained can be purified by an appropriate combination of well-known isolation or purification methods. Such isolation or purification methods include a method utilizing difference in solubility such as salting out, solvent precipitation; a method mainly utilizing difference in molecular weight such as dialysis, ultrafiltration, gel filtration, SDS-polyacrylamide gel electrophoresis; a method utilizing difference in electric charge such as ion exchange chromatography; a method utilizing specific affinity such as affinity chromatography; a method utilizing difference in hydrophobicity such as reversed phase high performance liquid chromatography; a method utilizing difference in isoelectric point such as isoelectrofocusing electrophoresis; and the like.

When the protein of the invention thus obtained is in a free form, it can be converted into a salt form by a well known method or a modification thereof. On the other hand, when the protein is obtained in a salt form, it can be converted into the free form or a different salt form by a well known method or a modification thereof.

The protein of the invention produced by the recombinant can be treated, before or after the purification, with an appropriate protein-modifying enzyme so that the protein can be appropriately modified or partially deleted. Examples of the protein-modifying enzyme include trypsin, chymotrypsin, arginyl endopeptidase, protein kinase, glycosidase and the like.

The thus produced protein of the invention can be detected using a specific antibody by an enzyme immunoassay or western blotting method.

The antibody to the protein of the invention, the partial peptide or the salt thereof may be any polyclonal antibodies or monoclonal antibodies, which are capable of recognizing the protein of the invention, the partial peptide or the salt thereof.

The antibody to the protein of the invention, the partial peptide or the salt thereof (occasionally referred to simply as the protein of the invention hereinafter in the description of antibodies) can be produced using the protein of the invention as an antigen by a known production method for antibodies or antisera.

[Preparation of Monoclonal Antibody]

(a) Preparation of Monoclonal Antibody-producing Cells

The protein of the invention is administered to warm-blooded animals either alone or together with carriers or diluents to the site which can induce the antibody production. To potentiate the antibody productivity, complete Freund's adjuvants or incomplete Freund's adjuvants may be administered at the same time. The administration is usually carried out once every 2 to 6 weeks and 2 to 10 times in total. Examples of applicable warm-blooded animals are monkeys, rabbits, dogs, guinea pigs, mice, rats, sheep, goats and chickens, with mice and rats being preferred.

To prepare monoclonal antibody-producing cells, a warm-blooded animal, e.g. mouse is immunized with an antigen, an individual whose antibody titer is high is selected, and then its spleen or lymph node is excised after 2 to 5 days from the final immunization. Antibody-producing cells contained therein are fused with myeloma cells of the same or different type animal to give a monoclonal antibody-producing hybridoma. The antibody titer in antisera may be assayed by reacting the labeled protein as described later, with the antiserum, and assaying the activity of the label bound to the antibody. The cell fusion may be carried out according to the known method by Koehler and Milstein (Nature, 256, 495 (1975)). A fusion promoter such as polyethylene glycol (PEG) and Sendai virus, preferably PEG; may be used.

The myeloma cells are ones derived from warm-blooded animals, such as NS-1, P3U1, SP2/0, AP-1. In particular, P3U1 is preferably employed. A preferred count ratio of the antibody-producing cells (spleen cells) to the myeloma cells is within a range of about 1:1 to 20:1. To efficiently carry out the cell fusion, it is preferred to add PEG (preferably PEG 1000 to PEG 6000) in a concentration of about 10 to 80% and incubate at 20 to 40° C., preferably at 30 to 37° C. for 1 to 10 minutes.

There are various methods used for screening of a monoclonal antibody-producing hybridoma. For example, a method may be used, which comprises adding the supernatant of hybridoma to a solid phase (e.g. microplate) adsorbed with the protein antigen directly or together with a carrier; adding an anti-immunoglobulin antibody (when mouse cells are used for the cell fusion, anti-mouse immunoglobulin antibody is used) which is labeled with a radioactive substance or an enzyme, or adding Protein A; and detecting the monoclonal antibody bound to the solid phase. Another method may be used, which comprises adding the supernatant of hybridoma to a solid phase adsorbed with an anti-immunoglobulin antibody or Protein A; adding the protein labeled with a radioactive substance or an enzyme; and detecting the monoclonal antibody bound to the solid phase.

The monoclonal antibody can be selected according to a publicly known method or its modification. In general, the selection can be carried out in a medium for animal cells supplemented with HAT (hypoxanthine, aminopterin and thymidine). Any medium can be used for the selection and growth as long as the hybridoma can grow there. For example, RPMI 1640 medium containing 1 to 20%, preferably 10 to 20% fetal bovine serum, GIT medium (Wako Pure Chemical Industries) containing 1 to 10% fetal bovine serum, or a serum free medium for hybridoma culture (SFM-101, Nissui Seiyaku) can be used. In general, the hybridoma may be cultured at 20 to 40° C., preferably at 37° C. for about 5 days to about 3 weeks, preferably 1 to 2 weeks under 5% $CO_2$. The antibody titer in the supernatant of the hybridoma culture can be determined in the same way as described above for the antibody titer in antisera.

(b) Purification of Monoclonal Antibody

The monoclonal antibody may be isolated or purified according to a publicly known method, e.g. the method for isolating or purifying immunoglobulins (for example, salting-out, alcohol precipitation, isoelectric point precipitation, electrophoresis, adsorption and desorption with ion exchangers (e.g. DEAE), ultracentrifugation, gel filtration, or a specific purification method which comprises collecting only an antibody with an activated adsorbent such as an antigen-binding solid phase, Protein A or Protein G, and dissociating the binding to obtain the antibody).

[Preparation of Polyclonal Antibody]

The polyclonal antibody of the invention can be produced by publicly known methods or modifications thereof. For example, a warm-blooded animal is immunized with an immunogen (a protein antigen) per se, or a complex of an immunogen and a carrier protein in a manner similar to the method described above for the production of monoclonal antibodies. The product containing the antibody to the protein of the invention is collected from the immunized animal, followed by separation and purification of the antibody.

In the complex of immunogen and carrier protein used to immunize a warm-blooded animal, any type of carrier protein and any mixing ratio of carrier to hapten can be used as long as the antibody is efficiently produced to the immunized hapten crosslinked to the carrier. For example, bovine serum albumin, bovine thyroglobulin or hemocyanin is crosslinked to the hapten in a carrier/hapten weight ratio of about 0.1 to 20, preferably about 1 to 5.

A variety of condensation agents can be used for the coupling of carrier to hapten. Glutaraldehyde, carbodiimide, maleimide-activated ester, activated ester reagents containing thiol group or dithiopyridyl group, and others are used for the coupling.

The condensate is administered to warm-blooded animals either alone or together with carriers or diluents to the site which can induce the antibody production. At the same time, to potentiate the antibody productivity, complete Freund's adjuvant or incomplete Freund's adjuvant may be administered. The administration is usually made once every about 2 to 6 weeks about 3 to 10 times in total.

The polyclonal antibody can be collected from the blood or ascites, preferably from the blood of warm-blooded animals immunized by the method described above.

The polyclonal antibody titer in antiserum can be assayed in the same way as described above for the assay of serum antibody titer. As well as the monoclonal antibody, the polyclonal antibody can also be isolated or purified according to the immunoglobulin purification method.

The antisense nucleotide having a base sequence complementary or substantially complementary to the DNA encoding the protein or the partial peptide of the invention (this DNA may be referred to as the DNA of the invention hereinafter in the description of the antisense nucleotide) refers to any antisense nucleotide having a base sequence complementary or substantially complementary to the DNA of the invention and having an activity to inhibit the expression of the DNA; the antisense DNA is preferred.

The base sequence substantially complementary to the DNA of the invention includes base sequences having at least about 70%, preferably at least about 80%, more preferably at least about 90%, and most preferably at least about 95% homology to the whole or a part of the base sequence complementary to the DNA of the invention (i.e. a complementary strand of the DNA of the invention). In particular, preferred is an antisense nucleotide having at least about 70%, preferably at least about 80%, more preferably at least about 90%, and most preferably at least about 95% homology to the complementary strand of the partial base sequence encoding the N-terminal region of the protein of the invention (e.g. the base sequence around the initiation codon) within the whole base sequence of the complementary strand of the DNA of the invention.

Specifically, the antisense nucleotide includes one having a whole or a part of a base sequence complementary or substantially complementary to the DNA having the base sequence represented by SEQ ID NO: 2, 7, 16 or 27; and preferably one having a whole or a part of a base sequence complementary to the DNA having the base sequence represented by SEQ ID NO: 2, 7, 16 or 27.

The antisense nucleotide may consist of usually about 10 to 40 and preferably 15 to 30 bases.

To prevent the degradation by hydrolase such as nuclease, phosphate residues (phosphates) of respective nucleotides constituting the antisense DNA may be replaced with chemically modified phosphate residues such as phosphorothioate, methyl phosphonate, and phosphorodithionate. These antisense nucleotides can be produced using a well known DNA synthesizer.

Hereinafter, described are utilities of the protein of the invention, the partial peptide or the salt thereof (hereinafter occasionally referred to as the protein of the invention); the DNA encoding the protein of the invention or the partial peptide thereof (hereinafter occasionally referred to as the DNA of the invention); the antibody to the protein of the invention or the partial peptide or the salt thereof (hereinafter occasionally referred to as the antibody of the invention); and the antisense nucleotide to the DNA of the invention (hereinafter occasionally referred to as the antisense nucleotide of the invention).

The protein comprising the same or substantially the same amino acid sequence as the amino acid sequence shown by SEQ ID NO: 1 (referred to as the human SGLT homolog protein) is highly expressed in human pancreas and liver in a tissue-specific manner. Therefore, it can be used as a pathological marker for diabetes, and it may be useful as a marker to make an early diagnosis of diabetes, to determine the severity of diabetes, and to predict progress of diabetes.

A pharmaceutical containing a compound or a salt thereof enhancing the activity of the human SGLT homolog protein is useful as a remedy or preventive for diabetes, because it can enhance glucose uptake into pancreatic beta cells to enhance the blood glucose-dependent insulin secretion; and also enhance glucose uptake from blood into liver in spite of glucose concentration gradient across the cell membrane in liver cells to prevent glucose release from liver into blood.

On the other hand, a pharmaceutical comprising a compound or a salt thereof inhibiting the activity of the human SGLT homolog protein is useful as a remedy or preventive for hyperlipidemia, because it can inhibit glucose reabsorption in kidney to decrease blood glucose, and thus prevent glucose uptake into liver to prevent fat synthesis (in diabetes).

The protein comprising the same or substantially the same amino acid sequence as the amino acid sequence shown by SEQ ID NO: 15 (referred to as the mouse SGLT homolog protein) is highly expressed in mouse kidney in a tissue-specific manner. Therefore, it can be used as a pathological marker for hyperlipidemia, and it may be useful as a marker to make an early diagnosis of hyperlipidemia, to determine the severity of hyperlipidemia, and to predict progress of hyperlipidemia.

A pharmaceutical comprising a compound or a salt thereof inhibiting the activity of the mouse SGLT homolog protein is useful as a remedy or preventive for hyperlipidemia, because it can inhibit glucose reabsorption in kidney to decrease blood glucose, and thus prevent glucose uptake into liver to prevent fat synthesis (in diabetes).

The protein comprising the same or substantially the same amino acid sequence as the amino acid sequence shown by SEQ ID NO: 26 (referred to as the rat SGLT homolog protein) is highly expressed in rat kidney in a tissue-specific manner. Therefore, it can be used as a pathological marker for hyperlipidemia, and it may be useful as a marker to make an early diagnosis of hyperlipidemia, to determine the severity of hyperlipidemia, and to predict progress of hyperlipidemia.

A pharmaceutical comprising a compound or a salt thereof inhibiting the activity of the rat SGLT homolog protein is useful as a remedy or preventive for hyperlipidemia, because it can inhibit glucose reabsorption in kidney to decrease blood glucose, and thus prevent glucose uptake into liver to prevent fat synthesis (in diabetes).

[1] A Prophylactic and/or Therapeutic Agent for Various Diseases Associated with the Protein of the Invention The protein of the invention has an active glucose transport activity as a Na+/glucose transporter, and is involved in the glucose uptake into pancreatic beta cells and the blood glucose-dependent insulin secretion. In liver cells, the protein is involved in the glucose uptake from blood into liver against glucose concentration gradient across the cell membrane.

Accordingly, when the DNA encoding the protein of the invention has an aberration or a deletion, or when the expression amount of the protein is decreased, various diseases such as diabetes are developed.

Thus, the protein of the invention and the DNA of the invention can be used as a medicine such as a prophylactic and/or therapeutic agent for diseases such as diabetes.

When the glucose uptake into pancreatic beta cells and/or liver cells is not shown sufficiently nor normally in a patient due to decrease or deficiency in the protein of the invention in vivo, the function of the protein can be expressed sufficiently or normally in the patient (a) by administering the DNA of the invention to the patient to express the protein of the invention in vivo, (b) by incorporating the DNA of the invention into a cell to express the protein of the invention, and then transplanting the cell to the patient, or (c) by administering the protein of the invention to the patient.

When the DNA of the invention is used as the prophylactic/therapeutic agent described above, the DNA can be administered to a human or another warm-blooded animal in a conventional manner as it is or after being inserted into an appropriate vector such as retrovirus vector, adenovirus vector, adenovirus-associated virus vector. The DNA of the invention may also be administered as it is, or in combination with a physiologically acceptable carrier such as an agent assisting its uptake, with the gene gun or a catheter such as the hydrogel catheter.

When the protein of the invention is used as the therapeutic/propbylactic agent, the protein is advantageously used at a purity of at least 90%, preferably at least 95%, more preferably at least 98% and even more preferably at least 99%.

The protein of the invention can be used orally, for example, in the form of tablets which may be sugar coated if necessary, capsules, elixirs or microcapsules; or parenterally in the form of injectable preparations such as a sterile solution and a suspension with water or other pharmaceutically acceptable liquid. These preparations can be produced by mixing the protein of the invention with a physiologically acceptable carrier, a flavoring agent, an excipient, a vehicle, an antiseptic agent, a stabilizer, a binder in a unit dosage form required for a generally accepted pharmaceutical preparation. The active ingredient in the preparation is adjusted appropriately within the specified range given.

Additives miscible in a tablet, a capsule, etc. include a binder such as gelatin, corn starch, tragacanth and gum arabic; an excipient such as crystalline cellulose; a swelling agent such as corn starch, gelatin and alginic acid; a lubricant such as magnesium stearate; a sweetening agent such as sucrose, lactose and saccharin; and a flavoring agent such as peppermint, akamono oil and cherry. When the unit dosage form is a capsule, liquid carriers such as oils and fats may further be used together with the additives described above. An injectable sterile composition may be formulated by conventional procedures used to make pharmaceutical compositions, e.g., by dissolving or suspending the active ingredients in a vehicle such as water for injection with a naturally occurring vegetable oil such as sesame oil, coconut oil.

Examples of an aqueous medium for injection include a physiological saline and an isotonic solution containing glucose and other auxiliary agents (e.g. D-sorbitol, D-mannitol, sodium chloride) and may be used in combination with an appropriate dissolution aid such as an alcohol (e.g. ethanol), a polyalcohol (e.g. propylene glycol, polyethylene glycol), a nonionic surfactant (e.g. polysorbate 80™ and HCO-50). Examples of the oily medium include sesame oil and soybean oil, which may also be used in combination with a dissolution aid such as benzyl benzoate and benzyl alcohol. The composition may further contain a buffer (e.g. phosphate buffer, sodium acetate buffer), a soothing agent (e.g. benzalkonium chloride, procaine hydrochloride), a stabilizer (e.g. human serum albumin, polyethylene glycol), a preservative (e.g. benzyl alcohol, phenol), an antioxidant, etc. The thus prepared liquid injection is normally filled in an appropriate ampoule.

The vector into which the DNA of the invention is inserted may also be formulated as a pharmaceutical preparation in a manner similar to the procedures above. Such a preparation is generally used parenterally.

Since the thus obtained pharmaceutical preparation is safe and low toxic, it can be administered to a warm-blooded animal (e.g. human, rat, mouse, guinea pig, rabbit, bird, sheep, swine, bovine, horse, cat, dog, monkey, chimpanzee). In particular, the preparation is preferably administered to a human.

The dose of the protein of the invention varies depending on a target disease, a subject, an administration route, etc. For example, in oral administration of the protein to an adult (60 kg body weight) for treatment of diabetes, the daily dose is normally about 0.1 to 100 mg, preferably about 1.0 to 50 mg, and more preferably about 1.0 to 20 mg of the protein. In parenteral administration, the single dose also varies depending on a subject, a target disease, etc., and it is advantageous to administer the protein intravenously at a daily dose of about 0.01 to 30 mg, preferably about 0.1 to 20 mg, and more preferably about 0.1 to 10 mg to an adult (60 kg body weight) for treatment of diabetes. For other animal species, the corresponding dose as converted per 60 kg body weight can be administered.

[2] Screening of a Pharmaceutical Compound Candidate for Diseases

The protein of the invention is useful as a reagent for screening of the compound or a salt thereof, which enhances or inhibits the activity of the protein of the invention.

Thus, the present invention provides:

(1) a method of screening for a compound or a salt thereof enhancing or inhibiting an activity of the protein of the invention (e.g. an active glucose transport activity)(hereinafter, the compound may be referred to as an enhancer or inhibitor, respectively), which comprises using the protein of the invention; and more specifically, for example, (2) the method of screening for the enhancer or inhibitor, which comprises comparing (i) a glucose uptake activity in cells having an ability of producing the protein of the invention, and (ii) a glucose uptake activity in cells having an ability of producing the protein of the invention in the presence of a test compound.

Specifically, in the above screening method, the glucose uptake activity can be determined by measuring radioactivity of the intracellular accumulation of [$^3$H]-labeled glucose or glucose analog such as 2-deoxy-glucose in the cases (i) and (ii), and compared these activities as an index for the active glucose transport activity.

In the screening method of the invention, to the cell having an ability of producing the protein of the invention, an inhibitor of active glucose transport activity (e.g. phlorizin) may be used as positive control.

Thus, the present invention provides the method of screening for the enhancer or inhibitor, which comprises:

(i) adding an inhibitor of active glucose transport activity to a cell having an ability of producing the protein of the invention at the same time of or before the cell takes in [$^3$H]-labeled glucose or glucose analog;

(ii) adding an activator or inhibitor of active glucose transport activity and a test compound to a cell having an ability of producing the protein of the invention at the same time of or before the cell takes in [$^3$H]-labeled glucose or glucose analog;

comparing an amount of the glucose, which the cell takes in in the case (i) and (ii); and determining the change of the uptake amount.

The test compound includes, e.g. peptides, proteins, non-peptide compounds, synthetic compounds, cell extracts, plant extracts, and animal tissue extracts, whichever novel or well known.

To prepare for carrying out the above-described screening methods, the cells having the ability of producing the protein of the invention are suspended in a buffer medium suitable for the screening. Any buffer of pH 4 to 10 (preferably pH about 6 to 8) can be used, which does not inhibit Na+ ion channel activity of the protein of the invention, including a phosphate buffer and a borate buffer.

The cell having the ability of producing the protein of the invention may be, for example, a host cell transformed with a vector comprising the DNA encoding the protein of the invention as described above (a transformant). Preferred hosts are such animal cells as CHO cells. For the screening, suitably used is a transformant expressing the protein of the invention on the cell membrane by being cultured according to the above-described method.

The active glucose transport activity of the protein of the invention can be measured according to a well known method, for example, the method described in "Cloning and functional expression of an SGLT-1-like protein from the *Xenopus laevis* intestine", Am. J. Phisiol. 276: G1251-G1259, 1999 or a modification thereof.

For example, a test compound enhancing the active glucose transport activity in the case (ii) by about 20% or more, preferably about 30% or more, and more preferably about 50% or more as compared with the case (i) can be selected as the compound enhancing the activity of the protein of the invention.

For example, a test compound inhibiting (or preventing) the active glucose transport activity in the case (ii) by about 20% or more, preferably about 30% or more, and more preferably about 50% or more as compared with the case (i) can be selected as the compound inhibiting the activity of the protein of the invention.

Furthermore, it is possible to screen for a compound or a salt thereof enhancing or inhibiting the expression of the protein of the invention (i.e. enhancing or inhibiting the activity of the protein of the invention) by:

inserting such a gene as secretory alkaline phosphatase gene and luciferase gene into the downstream of the promoter for the SGLT homolog protein gene of the invention;

expressing the gene product in a cell as described above;

contacting the cell with a test compound as described above; and screening for a compound or a salt thereof activating or inhibiting the enzyme activity of the gene product.

The screening kit of the invention comprises the protein used in the invention, the partial peptide or the salt thereof, or the cell having the ability of producing the protein used in the invention or the partial peptide thereof.

The compound or the salt thereof, which is obtained by the screening method or the screening kit of the invention, is selected from the above described test compounds such as peptides, proteins, non-peptide compounds, synthetic compounds, fermentation products, cell extracts, plant extracts, animal tissue extracts, blood plasma, and can enhance or inhibit the activity of the protein of the invention (e.g. an active glucose transport activity).

The salts of the compound used are the same kinds as the above-described salts of the protein of the invention.

The compounds or salts thereof capable of enhancing the activity of the protein of the invention are useful as pharmaceuticals such as remedies or preventives for diabetes in a human.

While, the compounds or salts thereof capable of inhibiting the activity of the protein of the invention are useful as pharmaceuticals such as remedies or preventives for hyperlipidemia.

When the compounds or salts thereof, which are obtained by the screening method or the screening kit of the invention, are used as the above-described remedies or preventives, they can be formulated in a conventional manner in a dosage form such as a tablet, capsule, elixir, microcapsule, sterile solution, and suspension.

Since the thus obtained pharmaceutical preparation is safe and low toxic, it can be administered orally or parenterally to, for example, a human or other warm-blooded animals (e.g. mouse, rat, rabbit, sheep, swine, bovine, horse, fowl, cat, dog, monkey, chimpanzee).

The dose of the compound or the salt thereof varies depending on its effect, a target disease, a subject, an administration route, etc. For example, when administering orally the compound or the salt thereof enhancing the activity of the protein of the invention to an adult (60 kg body weight) for treatment of diabetes, the daily dose is normally about 0.1 to 100 mg, preferably about 1.0 to 50 mg, and more preferably about 1.0 to 20 mg of the compound. In parenteral administration, the single dose of the compound or the salt thereof also varies depending on a subject, a target disease, etc. For example, when administering the compound or the salt thereof enhancing the activity of the protein of the invention to an adult (60 kg body weight) for treatment of diabetes in an injectable form, it is advantageous to inject intravenously the compound or the salt thereof in a daily dose of about 0.01 to 30 mg, preferably about 0.1 to 20 mg, and more preferably about 0.1 to 10 mg. For other animal species, the corresponding dose as converted per 60 kg body weight can be administered.

[3] Quantification of the Protein of the Invention, the Partial Peptide or the Salt Thereof The antibody to the protein of the invention (hereinafter sometimes simply referred to as the antibody of the invention) is capable of specifically recognizing the protein of the invention, and thus can be used for a quantification of the protein of the invention in a test liquid sample, in particular, for the quantification by sandwich immunoassay.

Thus, the present invention provides:

(i) a method of quantifying the protein of the invention in a test liquid sample, which comprises competitively reacting the antibody of the invention with the test liquid sample and a labeled form of the protein of the invention, and measuring the ratio of the labeled protein bound to the antibody; and (ii) a method of quantifying the protein of the invention in a test liquid sample, which comprises reacting the test liquid sample simultaneously or sequentially with the antibody of the invention immobilized on a carrier and a labeled form of another antibody of the invention, and then measuring the activity of the label on the immobilizing carrier.

In the quantification method (ii) described above, it is preferred that one antibody is capable of recognizing the N-terminal region of the protein of the invention, and the other antibody is capable of reacting the C-terminal region of the protein of the invention.

The monoclonal antibody to the protein of the invention (hereinafter sometimes referred to as the monoclonal antibody of the invention) can be used to quantify the protein of the invention, and to detect the protein in a tissue staining method as well. For these purposes, the antibody molecule per se may be used, or $F(ab')_2$, Fab' or Fab fraction of the antibody molecule may also be used.

There is no particular limitation for the type of quantification method using the antibody to the protein of the invention, and any assay methods can be used whereby the amount of antibody, antigen, or antibody-antigen complex corresponding to the amount of antigen (e.g. the amount of the protein) in a test liquid sample can be detected by chemical or physical means and the amount of the antigen can be calculated from a standard curve prepared from standard solutions containing known amounts of the antigen. Advantageously used are, for example, nephrometry, competitive method, immunometric method and sandwich method. In terms of sensitivity and specificity, the sandwich method, as described below, is particularly preferred.

Examples of the labeling agent used in the assay method using the labeled substance include radioisotopes, enzymes, fluorescent substances and luminescent substances, etc. Examples of the radioisotope include $[^{125}I]$, $[^{131}I]$, $[^{3}H]$, and $[^{14}C]$. Preferred examples of the enzyme are ones that are stable and have a high specific activity, including β-galactosidase, β-glucosidase, alkaline phosphatase, peroxidase, and malate dehydrogenase. Examples of the fluorescent substance include fluorescamine and fluorescein isothiocyanate. Examples of the luminescent substance include luminol, luminol derivatives, luciferin, and lucigenin. Furthermore, the biotin-avidin system may also be used for coupling of an antibody or antigen to the labeling agent.

For the immobilization of antigens or antibodies, physical attachment may be used. Alternatively, chemical coupling that is conventionally used for immobilization of proteins or enzymes may be used as well. Examples of the carrier include insoluble polysaccharides such as agarose, dextran and cellulose; synthetic resins such as polystyrene, polyacrylamide, silicone; or glass.

In the sandwich method, a test liquid sample is reacted with an immobilized monoclonal antibody of the invention (primary reaction), then reacted with another labeled monoclonal antibody of the invention (secondary reaction) and the activity of the label on the immobilizing carrier is assayed, whereby the amount of the protein of the invention in the test liquid sample can be quantified. The primary and secondary reactions may be carried out in a reversed order, simultaneously or sequentially with an interval. The type of the labeling agent and the method for the immobilization may be the same as those described above. In the immunoassay by the sandwich method, it is not always necessary that one type of the antibody is used for the immobilized or labeled antibody, but a mixture of two or more antibodies may also be used for the purpose of improving the measurement sensitivity.

In the quantification of the protein of the invention by the sandwich method, it is preferred that the monoclonal antibodies of the invention used for the primary and secondary reactions have different binding sites on the protein of the invention, respectively. Thus, in respect to the antibodies used in the primary and secondary reactions, for example, when the antibody used in the secondary reaction recognizes the C-terminal region of the protein of the invention, the antibody used in the primary reaction preferably recognizes a region other than the C-terminal region, for example, the N-terminal region.

The monoclonal antibody of the invention may be used in an assay system other than the sandwich method, such as a competitive method, an immunometric method, and a nephrometry.

In the competitive method, an antigen in a test liquid sample and a labeled antigen are competitively reacted with an antibody, and then the unreacted labeled antigen (F) and the labeled antigen bound to the antibody (B) are separated (i.e. B/F separation), and the amount of the label present in either B or F is measured to determine the amount of the antigen in the test liquid sample. For this reaction, used are a liquid phase method in which the used antibody is soluble and the B/F separation is performed by polyethylene glycol and a second antibody to the said antibody; and a solid phase method in which the first antibody is an immobilized one, or the first antibody is soluble and the second antibody is an immobilized one.

In the immunometric method, an antigen in a test liquid sample and an immobilized antigen are competitively reacted with a given amount of the labeled antibody, and then the solid phase is separated from the liquid phase; or an antigen in a test liquid sample and an excess amount of the labeled antibody are reacted, and then an immobilized antigen is added to bind the unreacted labeled antibody to the solid phase and the solid phase is separated from the liquid phase. Subsequently, the amount of the label in either of the phases is measured to determine the antigen amount in the test liquid sample.

In the nephrometry, the amount of insoluble sediment, which is produced as a result of the antigen-antibody reaction in a gel or in a solution, is measured. Even when the amount of an antigen in a test liquid sample is small and only a small amount of the sediment is obtained, a laser nephrometry utilizing laser scattering can be suitably used.

For applying these immunological methods to the quantification method of the invention, any special conditions or procedures are not required. A system for quantifying the protein of the invention may be constructed according to the combination of the usual technical consideration in the art and the conventional conditions and procedures. For the details of these general techniques, reference can be made to any reviews and textbooks.

See, for example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies))(all published by Academic Press).

As described above, the protein of the invention can be quantified with high sensitivity, using the antibody of the invention.

Furthermore, (1) when a decreased level of the protein of the invention is detected in a subject by quantifying the protein level using the antibody of the invention, the subject may be diagnosed as highly likely to suffer from such a disease as diabetes at that time or in the future.

The antibody of the invention can be used for detecting the protein of the invention in a test sample such as a body fluid and a tissue. The antibody can also be used for preparation of an antibody column for purification of the protein of the invention, detection of the protein in fractions upon purification, and analysis of the behavior of the protein in cells under investigation.

[4] Genetic Diagnosis Agents

The DNA of the invention or the single nucleotide polymorphisms (SNPs) thereof can be used as a probe, for example, to detect an abnormality of the DNA or mRNA encoding the protein of the invention or the partial peptide thereof in a human or other warm-blooded animals (e.g. rat, mouse, guinea pig, rabbit, fowl, sheep, swine, bovine, horse, cat, dog, monkey, chimpanzee)(gene abnormality). Therefore, it is useful as a genetic diagnosis agent for detecting the damage, mutation, decreased expression, or increased expression or overexpression of said DNA or mRNA.

The genetic diagnosis described above using the DNA of the invention can be performed by, for example, the well known northern hybridization assay or the PCR-SSCP assay (Genomics, 5 874-879 (1989); Proceedings of the National Academy of Sciences of the United States of America, 86, 2766-2770 (1989)), etc.

For example, when a decreased expression of the DNA is detected in a subject by the northern hybridization assay or when a mutation of the DNA is detected by the PCR-SSCP assay, the subject can be diagnosed as highly likely to suffer from such diseases as diabetes.

In very recent years, the polymorphic markers called SNPs (single nucleotide polymorphisms) appear as a very important tool for investigating a disease-related gene. The makers draw sudden attention as ones which define the susceptibility to a disease (easiness or difficulty to develop a disease), and have an influence on the responsiveness to a drug and development of side effects. A variety of methods of typing the SNPs can be used depending on the actual purpose, including the direct sequencing method, the Invader method, the Sniper method, MALDI-TOF/MS method, and oligo-SNP chip method (Jikken Igaku (Experimental Medicine) Vol. 18, No. 12, 2000).

The SNPs in the DNA encoding the protein of the invention (including a promoter region, exons, introns), as found in these ways, are useful, alone by itself or in combination with the analysis of SNPs in other genes, for determining the susceptibility to diabetes and hyperlipidemia; predicting the onset time of diabetes and hyperlipidemia; or making a diagnosis of diabetes and hyperlipidemia.

[5] Pharmaceuticals Containing the Antisense Nucleotide

The antisense nucleotide of the invention capable of binding complementally to the DNA of the invention and of suppressing the expression of the DNA shows low toxicity and can inhibit in vivo the functions of the protein or the DNA of the invention (e.g. Na+ ion channel activity, active glucose transport activity). Therefore, for example, it can be used as the prophylactic and therapeutic agent for hyperlipidemia and the like.

When used as the prophylactic and therapeutic agent as described above, the said antisense nucleotide can be formulated and administered according to a well-known method.

For example, when used, the antisense nucleotide can be orally or parenterally administered to a human or other mammals (e.g. rat, rabbit, sheep, swine, bovine, feline, canine, monkey) in a conventional manner, alone or after inserted into a suitable vector such as retrovirus vector, adenovirus vector, or adenovirus-associated virus vector. The antisense nucleotide can be administered using a gene gun or such a catheter as a hydrogel catheter, as it is or as formulated with a physiologically acceptable carrier such as an auxiliary material for uptake enhancement.

The dose of the antisense nucleotide varies depending on a target disease, a subject, an administration route, etc. For example, when the antisense nucleotide of the invention is locally administered to liver of an adult (60 kg body weight) for treatment of hyperlipidemia, it is generally administered in a daily dose of about 0.1 to 100 mg.

Further, the antisense nucleotide can be used as a diagnostic oligonucleotide probe to examine the presence or expression profile of the DNA of the invention in a tissue or a cell.

[6] DNA-transfected Animals

The present invention provides a non-human mammal having the foreign DNA encoding the protein of the present invention (abbreviated hereinafter as "the foreign DNA of the invention") or a mutated DNA thereof (sometimes abbreviated hereinafter as "the foreign mutated DNA of the present invention").

Thus, the invention provides:

(1) A non-human mammal having the foreign DNA of the present invention or the mutated DNA thereof;

(2) The animal described in (1) above, wherein the non-human mammal is a rodent;

(3) The animal described in (2) above, wherein the rodent is a mouse or rat; and (4) A recombinant vector comprising the foreign DNA of the present invention or the mutated DNA thereof, and having the ability of expressing the DNA in a mammal.

The non-human mammal having the foreign DNA of the present invention or the mutated DNA thereof (hereinafter abbreviated as "the DNA-transfected animal of the present invention") can be prepared by transfecting the desired foreign DNA of the present invention by a method such as the calcium phosphate method, electrical pulse method, lipofection method, agglutination method, microinjection method, particle gun method or DEAE-dextran method into germ cells and the like including unfertilized eggs, fertilized eggs, sperm and primordial cells thereof, preferably during the embryonic stage of non-human mammalian development (and more preferably during the single-cell or fertilized egg cell stage, generally before the eight-cell stage). Such DNA-transfection methods can also be used to transfect the desired foreign DNA of the present invention into somatic cells, living organs or tissue cells for cell culture or tissue culture. The DNA-transfected animal of the present invention can also be produced by fusing these cells with the aforementioned germ cells according to a well-known cell fusion method.

Non-human mammals that can be used include cows, pigs, sheep, goats, rabbits, dogs, cats, guinea pigs, hamsters mice and rats. Among them, from the standpoint of preparing a pathological animal model, a rodent is preferred which has relatively short ontogeny and life cycles and which are easy to breed, especially a mouse (e.g. pure strains such as C57BL/6 and DBA2; and hybrid strains such as B6C3F$_1$, BDF$_1$, B6D2F$_1$, BALB/c and ICR strains) and a rat (such as Wistar and SD strain).

In the context of the recombinant vector which can express the DNA in a mammal, the term "mammal" includes a human as well as a non-human mammal.

The foreign DNA of the present invention refers to the DNA of the present invention that has been previously isolated and extracted from mammals, but not the DNA of the present invention which the non-human mammals have intrinsically.

The mutated DNA of the present invention includes a DNA having a mutation (such as various mutations) in the original nucleotide sequence of the DNA of the present invention, specifically, a DNA having addition, deletion, or substitution of a nucleic acid, and also an abnormal DNA.

The abnormal DNA refers to a DNA which expresses the abnormal protein of the present invention, and includes a DNA which expresses a protein which can inhibit the function of the normal protein of the present invention.

The foreign DNA of the present invention may be derived from a mammal of either the same species or different species from the target animal. When transfecting the DNA of the present invention into the target animal, it is generally advantageous to use a DNA construct having the DNA ligated downstream of a promoter which can function in the animal cell. For example, when transfecting the human DNA of the present invention, a DNA-transfected mammal can be prepared, which highly expresses the DNA of the present invention, by microinjecting into the fertilized eggs of the target mammal, such as fertilized mouse eggs, a DNA construct (such as a vector) having the human DNA of the present invention ligated downstream of various promoters which can express a DNA derived from various mammals (such as rabbits, dogs, cats, guinea pigs, hamsters, rats or mice) having the DNA of the present invention, which is highly homologous to the human DNA.

Plasmids derived from E. coli, B. subtilis or yeast, bacteriophages such as λ-phage, retroviruses such as Moloney leukemia virus and animal viruses such as vaccinia virus and baculovirus may be used as the expression vector of the protein of the present invention. Among them, plasmids derived from E. coli, B. subtilis or yeast are preferred.

Promoters that can be used to regulate the DNA expression include (i) promoters derived from viruses (such as simian virus, cytomegalovirus, Moloney leukemia virus, JC virus, mammary tumor virus or polio virus), and (ii) promoters derived from various mammals (humans, rabbits, dogs, cats, guinea pigs, hamsters, rats, mice, etc.), such as promoters of albumin, insulin II, uroplakin II, elastase, erythropoietin, endothelin, muscle creatine kinase, glial fibrillary acidic protein, glutathione S-transferase, platelet derived growth factor β, keratin K1, K10 and K14, collagen Type I and Type II, cyclic AMP-dependent protein kinase βI subunit, dystrophin, tartaric acid-resistant alkali phosphatase, cardiac sodium diuretic factor, endothelial receptor tyrosine kinase (normally abbreviated as Tie2), sodium-potassium ATPase (Na,K-ATPase), neurofilament light chain, metallothionein I and IIA, tissue inhibitor of metalloproteinase-1, MHC class I antigen (H-2L), H-ras, renin, dopamine β-hydroxylase, thyroid peroxidase (TPO), polypeptide chain elongation factor 1α(EF-1α), β-actin, α- and β-myosin heavy chains, myosin light chains 1 and 2, myelin basic protein, thyroglobulin, Thy-1, immunoglobulin, H chain variable region (VNP), serum amyloid P component, myoglobin, troponin C, smooth muscle α-actin, preproenkephalin A, vasopressin. Particularly suitable are cytomegalovirus promoter, human polypeptide chain elongation factor 1α (EF-1α) promoter and human and chicken β-actin promoters, which allow strong expression throughout the body.

The said vectors should preferably have the sequence (generally called the terminator) which terminates transcription of the target mRNA in DNA-transfected mammals. Terminator DNA sequences derived from viruses and mammals can be used, and the simian virus SV40 terminator is preferably used.

In order to achieve greater expression of the desired foreign DNA, it is also possible depending on the purpose to attach various DNA splicing signals, enhancer regions or parts of eukaryote-derived DNA introns at 5'-upstream of the promoter region, between the promoter region and the translation region, or at 3'-downstream of the translation region.

The translation region of the normal protein of the present invention may be obtained as a whole or part of genomic DNA from DNAs derived from liver, kidney, thyroid cells or fibroblasts of various mammals (e.g. humans, rabbits, dogs, cats, guinea pigs, hamsters, rats, mice) or from various commercial genomic DNA libraries, or may be obtained from complement DNAs prepared by a well-known method from RNAs derived from liver, kidney, thyroid cells, or fibroblasts. To prepare the abnormal foreign DNA, the translation region of normal protein obtained from the aforementioned cells or tissues can be mutated by point mutagenesis.

A DNA construct enabling the expression of the translation region in the DNA-transfected animal can be produced by a conventional genetic engineering method of inserting the translation region after the aforementioned promoter, or if desired, before the transcription termination site.

Transfection of the foreign DNA of the present invention at the fertilized egg cell stage ensures that the DNA of the present invention will be present in all germ and somatic cells of the target mammal. The presence of the foreign DNA of the present invention in the animal's germ cells after the DNA transfection means that all the animal's progenies will retain the foreign DNA of the present invention in all their germ and somatic cells. The progenies of this animal that inherit the foreign DNA of the present invention have the DNA in all their germ and somatic cells.

The non-human mammal into which the normal foreign DNA of the present invention has been transfected can be bred after confirmation of stable retention of the foreign DNA, and can be successively reared in a normal environment as an animal retaining the DNA.

Transfection of the foreign DNA of the present invention at the fertilized egg cell stage ensures that the DNA of the present invention will be present in excess in all germ and somatic cells of the target mammal. The excessive presence of the foreign DNA of the present invention in the animal's germ cells after the DNA transfection means that all the animal's progenies will retain an excess of the foreign DNA of the present invention in all their germ and somatic cells. The progenies of this animal that inherit the foreign DNA of the present invention have an excess of the foreign DNA of the present invention in all their germ and somatic cells.

It is possible to obtain homozygotic animals having the transfected DNA in both homologous chromosomes, and to breed the male and female so that all the progenies have the DNA in excess.

The normal DNA of the present invention is highly expressed in the non-human mammal having the normal DNA of the present invention, leading to the promotion of the function of the intrinsic normal DNA and ultimately to the hyperfunction of the protein of the present invention. Such an animal is useful as a pathological animal model. For example, the normal DNA-transfected animal can be used to elucidate the pathology of hyperfunction of the protein of the present invention and other diseases related to the protein of the present invention, and to investigate therapies for these conditions.

Furthermore, since the mammal into which the normal foreign DNA of the present invention is transfected has symptoms due to increased free protein of the present invention, it can also be used in screening tests for pharmaceuticals for treatment of conditions related to the protein of the present invention.

The non-human mammal having the abnormal foreign DNA of the present invention can be bred after confirmation of stable retention of the foreign DNA, and can be successively reared in a normal environment as an animal retaining the DNA. Furthermore, the desired foreign DNA can be incorporated into one of the aforementioned plasmids and used as a material. A DNA construct with a promoter can be produced according to ordinary DNA engineering techniques. Transfection of the abnormal DNA of the present invention at the fertilized egg stage ensures that the abnormal DNA of the present invention is present in all the germ and somatic cells of the target mammal. The presence of the abnormal DNA of the present invention in the animal's germ cells after the DNA transfection means that all the animal's progenies will retain the abnormal DNA of the present invention in all their germ and somatic cells. The progenies of this animal that inherit the foreign DNA will have the abnormal DNA of the present invention in all their germ and somatic cells. It is possible to obtain homozygote animals having the transfected DNA in both homologous chromosomes, and to breed the male and female so that all the progenies have this DNA.

The abnormal DNA of the present invention is highly expressed in the non-human mammal having the abnormal DNA of the present invention, leading to the inhibition of the function of the intrinsic normal DNA, and ultimately to the dysfunction of the protein of the present invention. Such an animal is useful as a pathological animal model. For example, the abnormal DNA-transfected animal can be used to elucidate the pathology of dysfunction of the protein of the present invention, and to investigate therapies for this condition.

In a specific possible application, the animal that highly expresses the abnormal DNA of the present invention could be a model for elucidating the inhibitory mechanism of normal protein function (dominant negative effect) mediated by the abnormal protein in the dysfunction of the protein of the present invention.

Moreover, since the mammal into which the abnormal foreign DNA of the present invention is transfected has symptoms due to increased free protein of the present invention, it can also be used in screening tests for pharmaceuticals for treatment of dysfunction of the protein of the present invention.

Other possible applications of the said two types of DNA-transfected animals of the present invention include:
  (1) use as cell sources for tissue culture;
  (2) direct analysis of DNA or RNA in the tissue of DNA-transfected mammals of the present invention or analysis of proteins expressed in tissues to elucidate the involvement of proteins that are specifically expressed or activated by the protein of the present invention;
  (3) researching the function of cells derived from a tissue which is generally difficult to culture, by using cells derived from a tissue having the DNA of the present invention, wherein such cells can be cultured by standard tissue culture techniques;
  (4) screening for pharmaceuticals that enhance the cellular functions using the cells described in (3) above; and
  (5) isolation and purification of the mutated protein of the present invention, and production of antibodies thereto.

The DNA-transfected animals of the present invention could also be used to investigate the clinical symptoms of diseases related to the protein of the present invention, including dysfunction of the protein of the present invention, to obtain more detailed pathologies of various organs of the disease models related to the protein of the present invention, to develop new therapies, and to contribute to research and therapies for secondary conditions stemming from such diseases.

It is also possible to remove various organs from the DNA-transfected animals of the present invention, mince them, treat them with a protease such as trypsin to obtain free DNA-transfected cells, and culture the cells to prepare a cell line from the cultured cells. Since it is possible to specify the cells producing the protein of the present invention, and investigate the cells for apoptosis, differentiation and proliferation, and signal transduction, the cells can be effective research materials for understanding the protein of the present invention and action thereof.

Moreover, the DNA-transfected animals of the present invention may also be used to provide a rapid method of screening for a pharmaceutical for the treatment of diseases related to the protein of the present invention, including dysfunction of the protein of the present invention in the drug development using the assay methods and the quantifying method as described above. The DNA-transfected animals of the present invention or the vectors expressing the foreign DNA of the present invention may also be used to investigate and develop DNA therapies for diseases related to the protein of the present invention.

[7] Knockout Animals

The present invention provides a non-human mammal embryonic stem cell bearing the DNA of the invention inactivated and a non-human mammal deficient in expressing the DNA of the invention.

Thus, the present invention provides:

(1) a non-human mammal embryonic stem cell in which the DNA of the invention is inactivated;

(2) the embryonic stem cell according to (1), in which the DNA is inactivated by introducing a reporter gene (e.g. β-galactosidase gene derived from *Escherichia coli*);

(3) the embryonic stem cell according to (1), which is resistant to neomycin;

(4) the embryonic stem cell according to (1), wherein the non-human mammal is a rodent;

(5) the embryonic stem cell according to (4), wherein the rodent is mouse;

(6) a non-human mammal deficient in expressing the DNA of the invention, in which the DNA of the invention is inactivated;

(7) the non-human mammal according to (6), in which the DNA is inactivated by introducing a reporter gene (e.g. β-galactosidase derived from *Escherichia coli*) therein and the reporter gene can be expressed under the control of a promoter for the DNA of the invention;

(8) the non-human mammal according to (6), which is a rodent;

(9) the non-human mammal according to (8), wherein the rodent is a mouse; and,

(10) a method of screening for a compound that enhances or inhibits the promoter activity for the DNA of the invention, which comprises administering a test compound to the mammal of (7) and detecting expression of the reporter gene.

The non-human mammal embryonic stem cell in which the DNA of the invention is inactivated refers to the embryonic stem cells (abbreviated hereinafter as "ES cells") of a non-human mammal either in which the DNA expression ability is suppressed by the artificial mutation of the DNA of the invention present in the non-human mammal, or in which the activity of the protein of the invention encoded by said DNA has substantially been eliminated so that the DNA is not substantially capable of expressing the protein of the invention (sometimes referred to hereinafter as the knockout DNA of the invention).

The non-human mammals used are similar to those as described above.

Techniques for artificially mutating the DNA of the invention include deletion of a part or all of the DNA sequence and insertion of or substitution with other DNA, by genetic engineering. The knockout DNA of the invention may be prepared by these mutations, for example, by shifting the reading frame of a codon or by disrupting the function of a promoter or exon.

Specifically, the non-human mammal embryonic stem cell in which the DNA of the invention is inactivated (abbreviated hereinafter as the ES cells with the DNA of the invention inactivated or the knocked-out ES cells of the invention) can be produced as follows. For example, the DNA of the invention that the target non-human mammal has is isolated, a drug-resistant gene, of which typical examples are neomycin-resistant, hygromycin-resistant or other drug-resistant genes, or a reporter gene or the like, of which typical examples are 1 acZ (β-galactosidase gene) or cat (chloramphenicol acetyltransferase gene), is inserted into the exon to disrupt the function of the exon, or else a DNA sequence (such as polyA addition signal) which terminates the gene transcription is inserted into the intron between the exons to prevent synthesis of the complete mRNA. A DNA strand having the thus constructed DNA sequence to disrupt the gene (abbreviated hereinafter as "the targeting vector") is introduced into the chromosomes of the animal by homologous recombination. The knocked-out ES cell of the invention can be selected by analyzing the thus obtained ES cells either by the southern hybridization analysis using a DNA sequence on or near the DNA of the invention as a probe, or by the PCR analysis using as primers a DNA sequence on the targeting vector and a DNA sequence of a nearby region of the DNA of the invention used in producing the targeting vector.

The parent ES cells to inactivate the DNA of the invention by homologous recombination, etc. may be of a strain already established as described above, or may be originally established in accordance with a modification of the publicly known method by Evans and Kaufman. For example, in the case of mouse ES cells, currently it is common practice to use ES cells of the 129 strain, but their immunological genetic background is obscure. Accordingly, to establish another pure ES cell line, of which the immunological genetic background is clear, the C57BL/6 mouse or the BDF1 mouse (F1 hybrid between C57BL/6 and DBA/2), in which the low egg availability in the C57BL/6 mouse has been improved by crossing with DBA/2, may be preferably used. The BDF1 mouse is advantageous in that, when a pathologic model mouse is generated using the ES cells obtained therefrom, the genetic background can be changed to that of the C57BL/6 mouse by back-crossing with the C57BL/6 mouse, since its background is of the C57BL/6 mouse, as well as being advantageous in that egg availability is high and eggs are robust.

In establishing ES cells, blastocytes at 3.5 days after fertilization are normally used. As well, embryos can be collected at the 8-cell stage, and cultured until the blastocyte stage to efficiently obtain a large number of early stage embryos.

Although the ES cells used may be of either sex, male ES cells are generally more convenient for generation of a germ chimera cell. It is also desirable that sex of the ES cells is determined as soon as possible to save painstaking culture time.

Methods for sex determination of the ES cell include the method in which a gene in the sex-determining region on the Y-chromosome is amplified by the PCR process and detected. When this method is used, one colony of ES cells (about 50 cells) is sufficient for sex-determination, while karyotype analysis requires about $10^6$ cells. Therefore, the first selection of ES cells at the early stage of culture can be based on sex determination, and male cells can be selected early, which saves a significant amount of time at the early stage of culture.

Second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical procedures, etc. in the cell establishment, it is desirable that the ES cell is again cloned to a normal cell (e.g. a mouse cell having the number of chromosomes being 2n=40) after knockout of the gene of the ES cells.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and 90% air) in the presence of LIF (1 to 10000 U/ml) on appropriate feeder cells such as STO fibroblasts, and treated with a trypsin/EDTA solution (normally about 0.001 to about 0.5% trypsin/about 0.1 to about 5 mM EDTA, preferably about 0.1% trypsin/1 mM EDTA) at the time of passage to obtain separate single cells, which are then seeded on freshly prepared feeder cells. The passage is normally conducted every 1 to 3 days; it is desirable that cells be observed at passage and cells found to be morphologically abnormal in culture, if any, be discarded.

By culturing ES cells to reach a high density in monolayers or to form cell aggregates in suspension under appropriate conditions, they can differentiate to various cell types, for example, pariental and visceral muscles, cardiac muscle or the like (M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985). The cells deficient in expression of the DNA of the invention, which are obtained from the differentiated ES cells of the invention, are useful for an in vitro cell biological study of the function of the protein of the invention.

The non-human mammal deficient in expression of the DNA of the invention can be distinguished from a normal animal by measuring the mRNA amount in the subject animal by a publicly known method, and indirectly comparing the levels of expression.

The non-human mammals used are similar to those as described above.

With respect to the non-human mammal deficient in expression of the DNA of the invention, the DNA of the invention can be knocked out by transfecting a targeting vector, prepared as described above, into mouse embryonic stem cells or egg cells thereof, and conducting homologous recombination in which the DNA sequence in the transfected targeting vector, wherein the DNA of the invention is inactivated, replaces the DNA of the invention on a chromosome of mouse embryonic stem cells or egg cells thereof.

The cells in which the DNA of the invention is knocked out can be identified either by the southern hybridization analysis using a DNA sequence on or near the DNA of the invention as a probe, or by the PCR analysis using as primers a DNA sequence on the targeting vector and another DNA sequence of a nearby region of the mouse-derived DNA of the invention used in creating the targeting vector. When using non-human mammal embryonic stem cells, a cell line in which the DNA of the invention is inactivated by homologous recombination can be cloned, and the cloned cells are injected into an embryo or blastocyst of a non-human mammal at an appropriate stage such as the 8-cell stage. The resulting chimera embryo is then transplanted to the uterus of the pseudopregnant non-human mammal. The resulting animal is a chimera animal comprising both cells having the normal locus of the DNA of the invention and the artificially mutated locus of the DNA of the invention.

When some germ cells of the chimera animal have a mutation on the locus of the DNA of the invention, an individual, whose entire tissue is composed of cells having a mutation on the locus of the DNA of the invention can be selected from a series of offsprings obtained by crossing such a chimera animal and a normal animal, e.g., by coat color identification, etc. The individuals thus obtained are normally deficient in heterozygous expression of the protein of the invention. The individuals are deficient in homozygous expression of the protein of the invention and can be obtained from offsprings of the intercross of the individuals deficient in heterozygous expression of the protein of the invention.

When using egg cells, it is possible to obtain a transgenic non-human mammal having the targeting vector inserted into the chromosomes by microinjection of the DNA solution into an egg cell nucleus. From such transgenic non-human mammals, selected is one having the mutation on the DNA locus of the invention due to homologous recombination.

The animal in which the DNA of the invention has been knocked out in this way can be successively reared in a normal environment after confirmation that the DNA is knocked out in its offsprings obtained by breeding.

Reproductive lineages can also be obtained and maintained by ordinary methods. Thus, female and male animals having the inactivated DNA can be bred to obtain homozygote animals having the inactivated DNA in both loci of homologous chromosomes. The resulting homozygote animals can be efficiently reproduced by rearing under the condition of one normal individual and multiple homozygote individuals to a mother animal. By crossing male and female heterozygotes, homozygotes and heterozygotes having the inactivated DNA are successively reproduced.

The non-human mammal embryonic stem cell, in which the DNA of the invention is inactivated, is very useful for preparing a non-human mammal deficient in expression of the DNA of the invention.

Since the non-human mammal, in which the DNA of the invention is inactivated, lacks various biological activities derived from the protein of the invention, such an animal can be a model for a disease resulted from inactivated biological activities of the protein of the invention and thus, offers an effective study to investigate the causes for and therapy for these diseases.

[7a] A Method of Screening for a Compound Having a Therapeutic/Prophylactic Effect on Diseases Caused by Deletion, Damage, or the Like of the DNA of the Invention The non-human mammal deficient in expression of the DNA of the present invention can be employed for screening of a compound having therapeutic/prophylactic effects for diseases caused by deletion, damages, etc. of the DNA of the present invention (e.g. arteriosclerosis, hyperlipidemia, obesity, diabetes).

Thus, the present invention provides a method of screening for a compound or a salt thereof having therapeutic/prophylactic effects for diseases caused by deletion, damages, etc. of the DNA of the present invention, which comprises administering a test compound to the non-human mammal deficient in expression of the DNA of the present invention, and monitoring a change occurred in the animal.

As the non-human mammal deficient in expression of the DNA of the present invention which can be employed for the screening method, the same examples as given hereinabove apply.

Examples of the test compound include peptides, proteins, non-peptide compounds, synthetic compounds, fermentation products, cell extracts, vegetable extracts, animal tissue extracts, blood plasma and the like, and these compounds may be novel or known.

Specifically, after treating the non-human mammal deficient in expression of the DNA of the present invention with a test compound, and making a comparison with an intact control animal, a change in each organ, tissue, disease conditions, etc. of the animal is used as an index to assess the therapeutic/prophylactic effects of the test compound.

The method of treating an test animal with a test compound includes oral administration, intravenous injection, etc., and it is appropriately selected depending upon conditions of the test animal, properties of the test compound, etc. In addition, the dose of the test compound can be appropriately selected depending on the administration route, nature of the test compound and the like.

For example, for screening for a compound having a therapeutic/prophylactic effect on arteriosclerosis, the sugar loading is conducted to the non-human mammal deficient in expression of the DNA of the present invention. A test compound is administered before or after the sugar loading, and changes of the blood glucose level and body weight of the animal are measured with time.

In the screening method supra, when a test compound is administered to an test animal and then found to reduce the blood glucose level of the test animal by at least about 10%, preferably at least about 30%, and more preferably at least about 50%, the test compound can be selected to be a compound having a therapeutic/prophylactic effect on arteriosclerosis.

The compound obtained using the above screening method is selected from test compounds as described above and exhibits a therapeutic and prophylactic effect on the diseases caused by deficiencies, damages, etc. of the protein of the present invention (e.g. diabetes, hyperlipidemia). Therefore, the compound can be employed as a safe and low-toxic therapeutic and/or prophylactic agent for the diseases. Furthermore, a derivative from the compound obtained by the screening supra can be likewise employed.

The compound obtained by the screening above may be used in a salt form with a physiologically acceptable acid (e.g. inorganic acids or organic acids) or base (e.g. alkali metals), preferably in the form of a physiologically acceptable acid addition salt. Examples of such salts include salts with inorganic acids (e.g. hydrochloric acid, phosphoric acid, hydrobromic acid, sulfuric acid), salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A pharmaceutical composition comprising the compound obtained by the above screening method or a salt thereof may be manufactured in a manner similar to the method for preparing the composition comprising the protein of the present invention as described above. Since the pharmaceutical composition thus obtained is safe and low toxic, it can be administered to a mammal (e.g. human, rat, mouse, guinea pig, rabbit, sheep, swine, bovine, horse, cat, dog, monkey).

The dose of the compound or the salt thereof varies depending on a target disease, a subject to be administered, a route for administration, etc. For example, in oral administration of the compound to an adult (60 kg body weight) for treatment of diabetes, the daily dose is normally about 0.1 to 100 mg, preferably about 1.0 to 50 mg, and more preferably about 1.0 to 20 mg of the protein. In parenteral administration, the single dose also varies depending on a subject to be administered, a target disease, etc., and it is advantageous to administer the compound intravenously at a daily dose of about 0.01 to 30 mg, preferably about 0.1 to 20 mg, and more preferably about 0.1 to 10 mg to an adult (60 kg body weight) for treatment of diabetes. For other animal species, the corresponding dose as converted per 60 kg body weight can be administered.

[7b] A Method of Screening for a Compound that can Enhance or Inhibit the Activity of the Promoter for the DNA of the Invention The present invention provides a method for screening a compound that can enhance or inhibit the activity of the promoter for the DNA of the present invention or a salt thereof, which comprises administering a test compound to the non-human mammal deficient in expression of the DNA of the present invention and detecting expression of the reporter gene.

In the screening method supra, used is the non-human mammal deficient in expression of the DNA of the present invention in which the DNA of the present invention is inactivated by introducing a reporter gene and the reporter gene is expressed under control of the promoter for the DNA of the present invention.

Examples of the test compound are as described above.

Examples of the promoter for the DNA of the invention in the gene thereof include a promoter comprising the base sequence represented by SEQ ID NO: 51, 52, 53 or 54.

Examples of the reporter gene are as described above. Preferably employed are β-galactosidase gene (lacZ), soluble alkaline phosphatase gene, luciferase gene and the like.

In the non-human mammal deficient in expression of the DNA of the present invention wherein the DNA is substituted with the reporter gene, since the reporter gene is present under control of the promoter for the DNA of the present invention, the activity of the promoter can be detected by monitoring the expression of the substance encoded by the reporter gene.

For example, when a part of the DNA region encoding the protein of the present invention is substituted with β-galactosidase gene (lacZ) derived from *Escherichia coli*, β-galactosidase is expressed in place of the protein of the present invention in a tissue where the protein of the present invention should originally be expressed. Thus, the expression state of the protein of the present invention can be readily observed in an animal body by staining with a reagent, e.g. 5-bromo-4-chloro-3-indolyl-β-galactopyranoside (X-gal) which is substrate for β-galactosidase. Specifically, a mouse deficient in the protein of the present invention, or its tissue section is fixed with glutaraldehyde, washed with phosphate buffered saline (PBS), and then incubated with a staining solution containing X-gal at room temperature or about 37° C. for about 30 minutes to an hour. After the β-galactosidase reaction is terminated by washing the tissue preparation with 1 mM EDTA/PBS solution, the color change is observed. Alternatively, the mRNA encoding lacZ may be detected in a conventional manner.

The compound or a salt thereof obtained using the screening method supra is selected from the test compounds described above and can enhance or inhibit the activity of the promoter for the DNA of the present invention.

The compound obtained by the screening above may be used in a salt form with a physiologically acceptable acid (e.g. inorganic acids or organic acids) or base (e.g. alkali metals), preferably in the form of a physiologically acceptable acid addition salt. Examples of such salts include salts with inorganic acids (e.g. hydrochloric acid, phosphoric acid, hydrobromic acid, sulfuric acid), salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The compound or the salt thereof that can enhance the promoter activity for the DNA of the present invention can enhance the expression of the protein of the present invention, and finally enhance the function of the protein of the present invention. Accordingly, it is useful as a safe and low-toxic therapeutic and/or prophylactic agent for such a disease as diabetes.

The compound or a salt thereof that can inhibit the promoter activity for the DNA of the present invention can inhibit the expression of the protein of the present invention, and finally inhibit the function of the protein of the present invention. Accordingly, it is useful as a safe and low-toxic therapeutic and/or prophylactic agent for such a disease as hyperlipidemia.

A pharmaceutical composition comprising the compound or a salt thereof obtained by the screening method supra may be produced in a manner similar to the method for preparing the composition comprising the protein of the present invention as described above.

Since the pharmaceutical composition thus obtained is safe and low toxic, it can be administered to a mammal (e.g. human, rat, mouse, guinea pig, rabbit, sheep, swine, bovine, horse, cat, dog, monkey).

The dose of the compound or the salt thereof varies depending on a target disease, a subject to be administered, a route for administration, etc. For example, in oral administration of the compound enhancing the promoter activity for the DNA of the present invention to an adult (60 kg body weight) for treatment of diabetes, the daily dose is normally about 0.1 to 100 mg, preferably about 1.0 to 50 mg, more preferably about 1.0 to 20 mg for adult (as 60 kg body weight). In parenteral administration, the single dose of the compound also varies depending on a subject to be administered, a target disease, etc. For example, it is advantageous to administer intravenously in an injectable form the compound enhancing the promoter activity for the DNA of the present invention at a daily dose of about 0.01 to 30 mg, preferably about 0.1 to 20 mg, more preferably about 0.1 to 10 mg to an adult (60 kg body weight) for treatment of diabetes. For other animal species, the corresponding dose as converted per 60 kg weight can be administered.

As stated above, the non-human mammal deficient in expression of the DNA of the present invention is extremely useful for screening the compound or the salt thereof that can enhance the activity of the promoter for the DNA of the present invention, and can greatly contribute to the elucidation of causes for various diseases related to deficiency in expression of the DNA of the present invention, and to the development of a prophylactic/therapeutic agent for the diseases.

Furthermore, in case that a so-called transgenic animal (gene-transferred animal) is prepared by inserting various protein-coding genes to the downstream of the promoter region for the protein of the present invention in a DNA containing the promoter, and injecting the same into an animal egg, it can be used to study the functions of such a protein in vivo which can be expressed in a specific manner. As well, in case that a cell line is established in which an appropriate reporter gene is ligated to the said promoter site, it can be used as a research system for a low-molecular weigh compound capable of enhancing or inhibiting specifically the in vivo production of the protein of the present invention. It is also possible to search for a novel cis-element and a transcriptional factor capable of binding to the element through analysis of the promoter site.

In the specification and drawings, bases, amino acids, and the like are abbreviated in accordance with the IUPAC-IUB Commission on Biochemical Nomenclature or the conventional usage in the art, as shown below for example. When an amino acid has optical isomers, its L form is selected unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGlu | pyroglutamic acid |

Substituents, protecting groups and reagents used often in this specification are shown by the following codes.

| | |
|---|---|
| Me | methyl |
| Et | ethyl |
| Bu | butyl |
| Ph | phenyl |
| TC | thiazolidine-4(R)-carboxamido |
| Tos | p-toluenesulfonyl |
| CHO | formyl |
| Bzl | benzyl |
| Cl$_2$-Bzl | 2,6-dichlorobenzyl |
| Bom | benzyloxymethyl |
| Z | benzyloxycarbonyl |
| Cl-Z | 2-chlorobenzyloxycarbonyl |
| Br-Z | 2-bromobenzyloxycarbonyl |
| Boc | t-butoxycarbonyl |
| DNP | dinitrophenol |
| Trt | trityl |
| Bum | t-butoxymethyl |
| Fmoc | N-9-fluorenyl methoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboxyimide |
| DCC | N,N'-dichlorohexylcarbodiimide |

SEQ ID NOs in the sequence listing of the specification indicate the following sequences, respectively.

[SEQ ID NO: 1]
This shows the amino acid sequence of a human SGLT homolog protein.

[SEQ ID NO: 2]
This shows the base sequence of the DNA encoding the human SGLT homolog protein having the amino acid sequence represented by SEQ ID NO: 1.

[SEQ ID NO: 3]
This shows the base sequence of primer 1 used in Example 1.

[SEQ ID NO: 4]
This shows the base sequence of primer 2 used in Example 1.

[SEQ ID NO: 5]
This shows the base sequence of primer 3 used in Example 1.

[SEQ ID NO: 6]
This shows the base sequence of primer 4 used in Example 1.

[SEQ ID NO: 7]
This shows the base sequence of the DNA encoding the human SGLT homolog protein and containing 3'-untranslated region (2026-3140).

[SEQ ID NO: 8]
This shows the base sequence of primer 5 used in Example 2.

[SEQ ID NO: 9]
This shows the base sequence of primer 6 used in Example 2.

[SEQ ID NO: 10]
This shows the base sequence of primer 7 used in Example 3.

[SEQ ID NO: 11]
This shows the base sequence of primer 8 used in Example 3.

[SEQ ID NO: 12]
This shows the base sequence of the probe used in Example 3.

[SEQ ID NO: 13]
This shows the base sequence of primer 9 used in Example 3.

[SEQ ID NO: 14]
This shows the base sequence of primer 10 used in Example 3.

[SEQ ID NO: 15]
This shows the amino acid sequence of a mouse SGLT homolog protein.

[SEQ ID NO: 16]
This shows the base sequence of the DNA encoding the mouse SGLT homolog protein having the amino acid sequence represented by SEQ ID NO: 15.

[SEQ ID NO: 17]
This shows the base sequence of primer 11 used in Example 6.

[SEQ ID NO: 18]
This shows the base sequence of primer 12 used in Example 6.

[SEQ ID NO: 19]
This shows the base sequence of primer 13 used in Example 6.

[SEQ ID NO: 20]
This shows the base sequence of primer 14 used in Example 6.

[SEQ ID NO: 21]
This shows the base sequence of primer 15 used in Example 7.

[SEQ ID NO: 22]
This shows the base sequence of primer 16 used in Example 7.

[SEQ ID NO: 23]
This shows the base sequence of the probe used in Example 7.

[SEQ ID NO: 24]
This shows the base sequence of primer 17 used in Example 7.

[SEQ ID NO: 25]
This shows the base sequence of primer 18 used in Example 7.

[SEQ ID NO: 26]
This shows the amino acid sequence of a rat SGLT homolog protein.

[SEQ ID NO: 27]
This shows the base sequence of the DNA encoding the rat SGLT homolog protein having the amino acid sequence represented by SEQ ID NO: 26.

[SEQ ID NO: 28]
This shows the base sequence of primer 19 used in Example 10.

[SEQ ID NO: 29]
This shows the base sequence of primer 20 used in Example 10.

[SEQ ID NO: 30]
This shows the base sequence of primer 21 used in Example 10.

[SEQ ID NO: 31]
This shows the base sequence of primer 22 used in Example 10.

[SEQ ID NO: 32]
This shows the base sequence of primer 23 used in Example 11.

[SEQ ID NO: 33]
This shows the base sequence of primer 24 used in Example 11.

[SEQ ID NO: 34]
This shows the base sequence of the probe used in Example 11.

[SEQ ID NO: 35]
This shows the base sequence of primer 25 used in Example 11.

[SEQ ID NO: 36]
This shows the base sequence of primer 26 used in Example 11.
[SEQ ID NO: 37]
This shows the amino acid sequence of the immunogen peptide used in Example 14.
[SEQ ID NO: 38]
This shows the base sequence of the primer for introduction of C1 mutation, used in Example 17.
[SEQ ID NO: 39]
This shows the base sequence of the primer for introduction of C2 mutation, used in Example 17.
[SEQ ID NO: 40]
This shows the base sequence of the DNA having the C1 base substitution, obtained in Example 17.
[SEQ ID NO: 41]
This shows the amino acid sequence of the peptide derived from the C1 base substitution, obtained in Example 17.
[SEQ ID NO: 42]
This shows the base sequence of the DNA having the C2 base substitution, obtained in Example 17.
[SEQ ID NO: 43]
This shows the amino acid sequence of the peptide derived from the C2 base substitution, obtained in Example 17.
[SEQ ID NO: 44]
This shows the base sequence of the primer for introduction of C3 mutation, used in Example 17.
[SEQ ID NO: 45]
This shows the base sequence of the DNA having the C3 base substitution, obtained in Example 17.
[SEQ ID NO: 46]
This shows the amino acid sequence of the peptide derived from the C3 base substitution, obtained in Example 17.
[SEQ ID NO: 47]
This shows the base sequence of primer 27 used in Example 20.
[SEQ ID NO: 48]
This shows the base sequence of primer 28 used in Example 20.
[SEQ ID NO: 49]
This shows the base sequence of primer K1 used in Example 20.
[SEQ ID NO: 50]
This shows the base sequence of primer X1 used in Example 20.
[SEQ ID NO: 51]
This shows the base sequence of the DNA region from 2261 bp to 8 bp upstream of the translation start of the human SGLT homolog gene, obtained in Example 20.
[SEQ ID NO: 52]
This shows the base sequence of the primer for introduction of P1 mutation, used in Example 21.
[SEQ ID NO: 53]
This shows the base sequence of the primer for introduction of P2 mutation, used in Example 21.
[SEQ ID NO: 54]
This shows the base sequence of the DNA having the P2 base substitution, obtained in Example 21.
[SEQ ID NO: 55]
This shows the base sequence of the DNA having the P1 base substitution, obtained in Example 21.
[SEQ ID NO: 56]
This shows the base sequence of the DNA having both P1 and P2 base substitutions, obtained in Example 21.
[SEQ ID NO: 57]
This shows the base sequence of primer K2 used in Example 22.
[SEQ ID NO: 58]
This shows the base sequence of primer K3 used in Example 22.
[SEQ ID NO: 59]
This shows the base sequence of primer X2 used in Example 22.
[SEQ ID NO: 60]
This shows the base sequence of primer 29 used in Example 24.
[SEQ ID NO: 61]
This shows the base sequence of primer 30 used in Example 24.
[SEQ ID NO: 62]
This shows the base sequence of primer 31 used in Example 24.
[SEQ ID NO: 63]
This shows the base sequence of primer 32 used in Example 24.
[SEQ ID NO: 64]
This shows the base sequence of primer 33 used in Example 24.
[SEQ ID NO: 65]
This shows the base sequence of primer 34 used in Example 24.
[SEQ ID NO: 66]
This shows the base sequence of primer 35 used in Example 24.
[SEQ ID NO: 67]
This shows the base sequence of primer 36 used in Example 24.
[SEQ ID NO: 68]
This shows the base sequence of primer 37 used in Example 24.
[SEQ ID NO: 69]
This shows the base sequence of primer 38 used in Example 24.
[SEQ ID NO: 70]
This shows the base sequence of primer 39 used in Example 24.
[SEQ ID NO: 71]
This shows the base sequence of primer 40 used in Example 24.

The transformant *Escherichia coli* DH5α/pTB2193, obtained in Example 1 is deposited at International Patent Organism Depositary, National Institute of Advanced Industrial Science and Technology (now-definct National Institute of Bioscience and Human Technology (NIBH), Agency of Industrial Science and Technology, Ministry of International Trade and Industry), located at Center No. 6, 1-1-1 Higasi, Tukuba-shi, Ibaraki 305-8566, Japan, under Accession Number FERM BP-7410 since Dec. 22, 2000; and at Institute for Fermentation, Osaka (IFO), located at 2-17-85, Jyuso-Honmati, Yodogawa-ku, Osaka-shi, Osaka 532-8686, Japan, under Accession Number IFO 16516 since Dec. 14, 2000.

The transformant *Escherichia coli* DH5α/TKD-1, obtained in Example 2 is deposited at International Patent Organism Depositary, National Institute of Advanced Industrial Science and Technology (now-defunct National Institute of Bioscience and Human Technology (NIBH), Agency of Industrial Science and Technology, Ministry of International Trade and Industry), located at Center No. 6, 1-1-1 Higasi, Tukuba-shi, Ibaraki 305-8566, Japan, under Accession Number FERM BP-7629 since Jun. 14, 2001; and at Institute for Fermentation, Osaka (IFO), located at 2-17-85, Jyuso-Honmati, Yodogawa-ku, Osaka-shi, Osaka 532-8686, Japan, under Accession Number IFO 16648 since Jun. 5, 2001.

The transformant *Escherichia coli* DH5α/pTB2238, obtained in Example 6 is deposited at International Patent Organism Depositary, National Institute of Advanced Industrial Science and Technology (now-defunct National Institute of Bioscience and Human Technology (NIBH), Agency of Industrial Science and Technology, Ministry of International Trade and Industry), located at Center No. 6, 1-1-1 Higasi, Tukuba-shi, Ibaraki 305-8566, Japan, under Accession Number FERM BP-7776 since Oct. 15, 2001; and at Institute for Fermentation, Osaka (IFO), located at 2-17-85, Jyuso-Honmati, Yodogawa-ku, Osaka-shi, Osaka 532-8686, Japan, under Accession Number IFO 16708 since Sep. 27, 2001.

The transformant *Escherichia coli* DH5α/pTB2239, obtained in Example 10 is deposited at International Patent Organism Depositary, National Institute of Advanced Industrial Science and Technology (now-defunct National Institute of Bioscience and Human Technology (NIBH), Agency of Industrial Science and Technology, Ministry of International Trade and Industry), located at Center No. 6, 1-1-1 Higasi, Tukuba-shi, Ibaraki 305-8566, Japan, under Accession Number FERM BP-7777 since Oct. 15, 2001; and at Institute for Fermentation, Osaka (IFO), located at 2-17-85, Jyuso-Honmati, Yodogawa-ku, Osaka-shi, Osaka 532-8686, Japan, under Accession Number IFO 16709 since Sep. 27, 2001.

The transformant *Escherichia coli* XL1-Blue/pTB2251, obtained in Example 17 is deposited at International Patent Organism Depositary, National Institute of Advanced Industrial Science and Technology (now-defunct National Institute of Bioscience and Human Technology (NIBH), Agency of Industrial Science and Technology, Ministry of International Trade and Industry), located at Center No. 6, 1-1-1 Higasi, Tukuba-shi, Ibaraki 305-8566, Japan, under Accession Number FERM BP-7815 since Dec. 6, 2001; and at Institute for Fermentation, Osaka (IFO), located at 2-17-85, Jyuso-Honmati, Yodogawa-ku, Osaka-shi, Osaka 532-8686, Japan, under Accession Number IFO 16726 since Nov. 13, 2001.

The transformant *Escherichia coli* XL1-Blue/pTB2252, obtained in Example 17 is deposited at International Patent Organism Depositary, National Institute of Advanced Industrial Science and Technology (now-defunct National Institute of Bioscience and Human Technology (NIBH), Agency of Industrial Science and Technology, Ministry of International Trade and Industry), located at Center No. 6, 1-1-1 Higasi, Tukuba-shi, Ibaraki 305-8566, Japan, under Accession Number FERM BP-7816 since Dec. 6, 2001; and at Institute for Fermentation, Osaka (IFO), located at 2-17-85, Jyuso-Honmati, Yodogawa-ku, Osaka-shi, Osaka 532-8686, Japan, under Accession Number IFO 16727 since Nov. 13, 2001.

The transformant *Escherichia coli* DH5α/pTB2253, obtained in Example 17 is deposited at International Patent Organism Depositary, National Institute of Advanced Industrial Science and Technology (now-defunct National Institute of Bioscience and Human Technology (NIBH), Agency of Industrial Science and Technology, Ministry of International Trade and Industry), located at Center No. 6, 1-1-1 Higasi, Tukuba-shi, Ibaraki 305-8566, Japan, under Accession Number FERM BP-7817 since Dec. 6, 2001; and at Institute for Fermentation, Osaka (IFO), located at 2-17-85, Jyuso-Honmati, Yodogawa-ku, Osaka-shi, Osaka 532-8686, Japan, under Accession Number IFO 16729 since Nov. 13, 2001.

The transformant *Escherichia coli* XL1-Blue/pTB2254, obtained in Example 20 is deposited at International Patent Organism Depositary, National Institute of Advanced Industrial Science and Technology (now-defunct National Institute of Bioscience and Human Technology (NIBH), Agency of Industrial Science and Technology, Ministry of International Trade and Industry), located at Center No. 6, 1-1-1 Higasi, Tukuba-shi, Ibaraki 305-8566, Japan, under Accession Number FERM BP-7818 since Dec. 6, 2001; and at Institute for Fermentation, Osaka (IFO), located at 2-17-85, Jyuso-Honmati, Yodogawa-ku, Osaka-shi, Osaka 532-8686, Japan, under Accession Number IFO 16729 since Nov. 20, 2001.

The transformant *Escherichia coli* XL1-Blue/pTB2255, obtained in Example 21 is deposited at International Patent Organism Depositary, National Institute of Advanced Industrial Science and Technology (now-defunct National Institute of Bioscience and Human Technology (NIBH), Agency of Industrial Science and Technology, Ministry of International Trade and Industry), located at Center No. 6, 1-1-1 Higasi, Tukuba-shi, Ibaraki 305-8566, Japan, under Accession Number FERM BP-7819 since Dec. 6, 2001; and at Institute for Fermentation, Osaka (IFO), located at 2-17-85, Jyuso-Honmati, Yodogawa-ku, Osaka-shi, Osaka 532-8686, Japan, under Accession Number IFO 16730 since Nov. 20, 2001.

The transformant *Escherichia coli* XL1-Blue/pTB2256, obtained in Example 21 is deposited at International Patent Organism Depositary, National Institute of Advanced Industrial Science and Technology (now-defunct National Institute of Bioscience and Human Technology (NIBH), Agency of Industrial Science and Technology, Ministry of International Trade and Industry), located at Center No. 6, 1-1-1 Higasi, Tukuba-shi, Ibaraki 305-8566, Japan, under Accession Number FERM BP-7820 since Dec. 6, 2001; and at Institute for Fermentation, Osaka (IFO), located at 2-17-85, Jyuso-Honmati, Yodogawa-ku, Osaka-shi, Osaka 532-8686, Japan, under Accession Number IFO 16731 since Nov. 20, 2001.

The transformant *Escherichia coli* DH5α/pTB2257, obtained in Example 21 is deposited at International Patent Organism Depositary, National Institute of Advanced Industrial Science and Technology (now-defunct National Institute of Bioscience and Human Technology (NIBH), Agency of Industrial Science and Technology, Ministry of International Trade and Industry), located at Center No. 6, 1-1-1 Higasi, Tukuba-shi, Ibaraki 305-8566, Japan, under Accession Number FERM BP-7832 since Dec. 19, 2001; and at Institute for Fermentation, Osaka (IFO), located at 2-17-85, Jyuso-Honmati, Yodogawa-ku, Osaka-shi, Osaka 532-8686, Japan, under Accession Number IFO 16732 since Nov. 20, 2001.

EXAMPLES

The invention is specifically described below with reference to Examples, but not limited thereto. Genetic procedures using *Escherichia coli* followed methods described in "Molecular Cloning".

Example 1

Cloning of the cDNA Encoding the Human Pancreas-derived Na+/Glucose Transporter Protein and Determination of the Base Sequence A PCR was carried out using human pancreas cDNA (CLONTECH) as a template and 2 primers, i.e. primer 1 (SEQ ID NO: 3) and primer 2 (SEQ ID NO: 4). The reaction solution for the PCR contained 1 µl of the said cDNA as the template, 1 µl of Pfu Turbo DNA polymerase (STRATAGENE), 0.5 µM each of primer 1 (SEQ ID NO: 3) and primer 2 (SEQ ID NO: 4), 200 µM dNTPs, and 5 µl of the buffer solution attached to the enzyme product in a total volume of 50 µl. The PCR consisted of a reaction at 94° C. for 1 minute; next 35 cycles of reactions at 96° C. for 20 seconds, at 60° C. for 30 seconds and 72° C. for 2 minutes; and a final elongation reaction at 72° C. for 7 minutes.

A further PCR was carried out using the resulting PCR product as a template and 2 primers, i.e. primer 3 (SEQ ID NO: 5) and primer 4 (SEQ ID NO: 6). The reaction solution for the PCR contained 1 µl of the PCR product as the template, 1 µl of Pfu Turbo DNA polymerase (STRATAGENE), 0.5 µM each of primer 3 (SEQ ID NO: 5) and primer 4 (SEQ ID NO: 6), 200 µM dNTPs, and 5 µl of the buffer solution attached to the enzyme product in a total volume of 50 µl. The PCR consisted of a reaction at 94° C. for 1 minute; next 35 cycles of reactions at 96° C. for 20 seconds, at 60° C. for 30 seconds and 72° C. for 2 minutes; and a final elongation reaction at 72° C. for 7 minutes.

The resulting PCR product and the plasmid vector pME18S were digested overnight at 37° C. with EcoRI and SpeI. After separated by electrophoresis on 1% agarose gel, 2 Kbp DNA fragment (SGLT homolog) and 3 Kbp DNA fragment (pME18S) were excised and extracted with Gel Extraction Kit (Qiagen). The SGLT homolog was subcloned into pME18S using Ligation Kit (Takara). The resulting product was transfected into *E. coli* DH5α, and clones containing the cDNA were selected on LB agar media containing ampicillin. After analysis of the sequence of each clone, the cDNA sequence (SEQ ID NO: 2) encoding a novel Na+/glucose transporter protein was obtained. This novel Na+/glucose transporter protein comprising the amino acid sequence (SEQ ID NO: 1) was referred to as the human SGLT homolog, and the transformant was referred to as *Escherichia coli* DH5α/pTB2193.

The hydropathy plot of the human SGLT homolog is shown in FIG. 1.

Example 2

Cloning of the cDNA Encoding the Human Liver-derived Na+/Glucose Transporter Protein and Determination of the Base Sequence The cDNA was cloned from the human liver cDNA library (CLONTECH) using ClonCapture cDNA Selection Kit (CLONTECH). The biotinylated probe used was a 403 bp fragment, which was amplified by PCR using the human SGLT homolog cDNA as a template, and primer 5 (5'-ggtctgcgggggctgatgattg-3')(SEQ ID NO: 8) and primer 6 (5'-aggctggcgctgggtatgagaac-3')(SEQ ID NO: 9).

A colony PCR was carried out using primers 1 and 2 to select *E. coli* having the SGLT homolog cDNA. After analysis of base sequences of the obtained clones, the cDNA sequence (SEQ ID NO: 7) encoding the SGLT homolog protein and also containing 3'-untranslated region (2026-3140) was obtained. The transformant was referred to as *Escherichia coli* DH5α/TKD-1.

Example 3

Analysis of Distribution of the Expressed Human SGLT Homolog Using Taqman PCR The primers and probe used for Taqman PCR were searched using Primer Express ver. 1.0 (PE Biosystem, Japan) and selected as follows:

```
                                        (SEQ ID NO: 10)
primer 7:   (5'-cccgatgctttccacattcttc-3');

(SEQ ID NO: 11)
primer 8:   (5'-acaatgacctggtctgtgcacc-3');

(SEQ ID NO: 12)
probe:      (5'-acatcccttggccaggtctcattttcgg-3').
```

A reporter dye FAM (6-carboxyfluorescein) was added to the probe.

The PCR fragment of the human SGLT homolog was used as a standard DNA. The reaction solution for the PCR contained 1 µl of pTB2193 DNA as the template, 1 µl of Pfu Turbo DNA polymerase (STRATAGENE), 0.5 µM each of primer 9 (5'-gggggccagaggatccaggtgta-3', SEQ ID NO: 13) and primer 10 (5'-gcaatcatcagcccccgcagac-3', SEQ ID NO: 14), 200 µM dNTPs, and 5 µl of the buffer solution attached to the enzyme product in a total volume of 50 µl. The PCR consisted of a reaction at 94° C. for 1 minute; next 35 cycles of reactions at 96° C. for 20 seconds, at 60° C. for 30 seconds and 72° C. for 1 minutes; and a final elongation reaction at 72° C. for 7 minutes. The PCR product was subjected to electrophoresis on 1% agarose gel, and 0.7 Kbp DNA fragment was excised and extracted with Gel Extraction Kit (Qiagen). The PCR fragment, adjusted in concentrations of $10^0$ to $10^6$ copies/µl, was used as the standard DNA.

Human Multiple Tissue cDNA Panel I and II (CLONTECH) were used as cDNA sources of various tissues. The PCR for the analysis was carried out using 200 nM of primer 7, 100 nM of primer 8, 50 nM of the probe and each template DNA, all of which were added to a given amount of Taqman Universal PCR Master Mix (PE Biosystems, Japan) according to the manufacture's instructions, on ABI PRISM 7700 Sequence Detection System (PE Biosystems, Japan).

Figure 2:
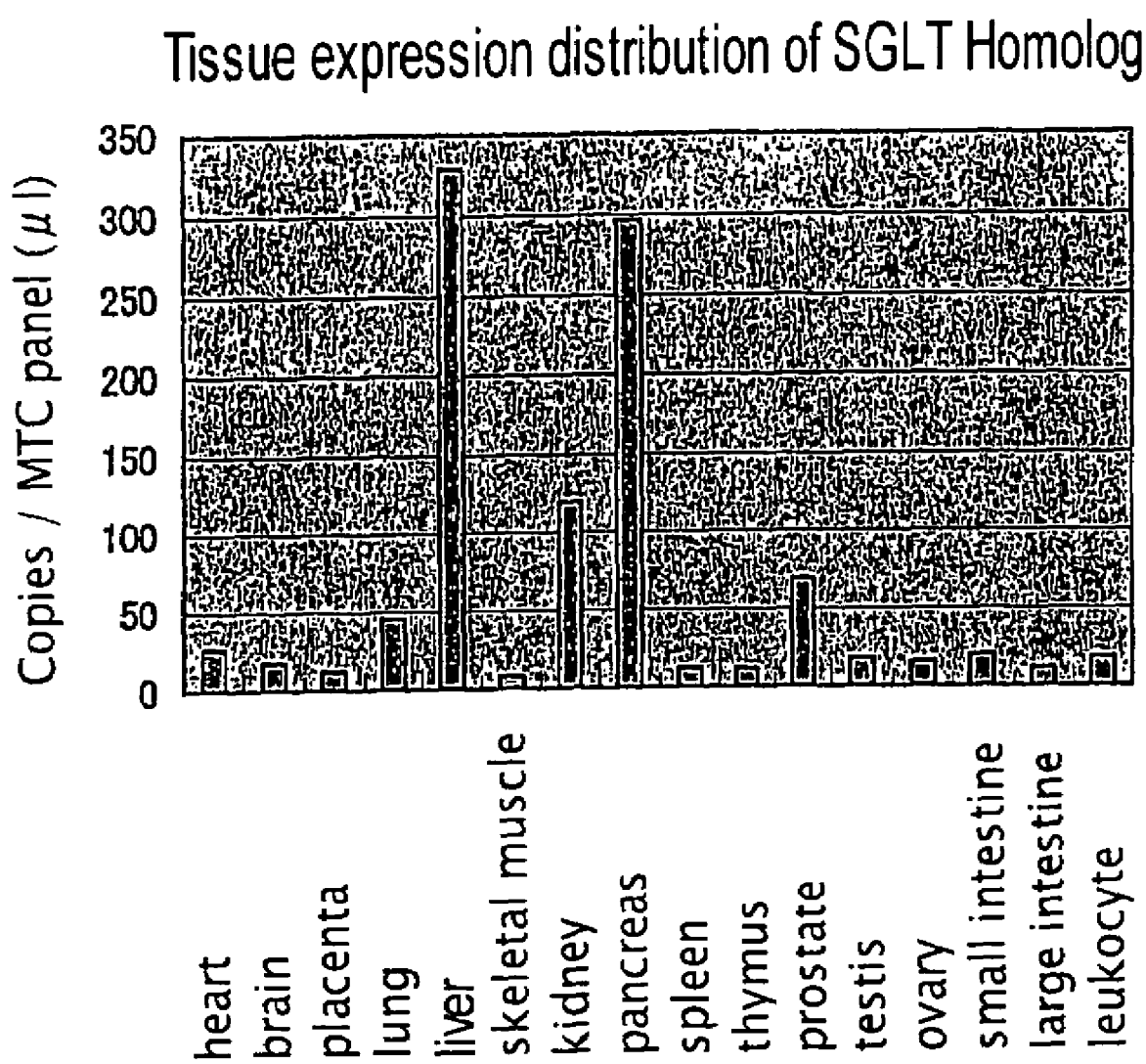
FIG. 2 shows the tissue expression distribution of the human SGLT homolog. The MTC panel contains a standardized amount of each cDNA.

The results are shown in FIG. 2. The expression of the human SGLT homolog was primarily observed in pancreas and liver.

Example 4

Preparation of Cells Expressing SGLTs

Each cDNA of human SGLT1 (NCBI Accession NM_000343) and SGLT2 (NCBI Accession NM_003041) was amplified by PCR from Clontech MTC panel kidney cDNA library, and subcloned into the expression vector for animal cells, pME18S between EcoRI and SpeI sites to prepare pME18S-hSGLT1 and pME18S-hSGLT2. CHO cells ($1 \times 10^6$ cells) were co-transfected with each 5 µg of plasmids pME18S, pMEI 8S-SGLT homolog, pMEI 8S-hSGLT1, and pME18S-hSGLT2, and the expression vector for animal cells, pRSVneo 0.5 µl according to the Lipo-fectAMINE PLUS method (GIBCOBRL). These cells were cultured in DMEM containing G418 (500 µg/ml) and 10% FBS for 2 weeks to select the drug-resistant clones.

Total RNAs were extracted from respective G418-resistant CHO cells using RNAeasy Mini Kit (Quiagen). The expression of the SGLT homolog, hSGLT1 and hSGLT2 was quantified using TaqMan Gold RT-PCR Kit (PE Biosystems) according to the TaqMan PCR method to select CHO cells expressing each gene.

Example 5

Quantification of Glucose Uptake

Experimental incorporation of α-methyl glucose into the CHO cell expressing the SGLT homolog, the CHO cell expressing hSGLT1, the CHO cell expressing hSGLT2, and the CHO cell having pME18S was carried out according to the method described in Am. J. Physiol. 270:G833-G843 (1996) and J. Clin. Invest. 93:397-404, 1994. The cells were plated on a 96-well plate in a cell density of $1 \times 10^5$ cells/well and in a volume of 100 µl of DMEM containing 10% FBS per well, and cultured overnight at 37° C. The cells were washed 3 times with 150 µl of a buffer solution (125 mM KCl, 1.2 mM $KH_2PO_4$, 2.5 mM $CaCl_2$, 1.2 mM $MgSO_4$, 4 mM Glutamine, 10 mM HEPES (pH 7.2), 0.1 mg/ml BSA), and cultured for an hour in the same buffer solution to remove the rest of glucose. The buffer solution was removed and replaced with 90 µl of the same buffer solution or the buffer solution containing NaCl or NaCl +10 µM or 100 µM Phlorizin (Sigma) in place of KCl. After one-hour incubation with 10 µl of 1 mM α-methyl glucose (containing 0.02 µCi of [$^{14}C$]-α-methyl glucose (Amersham Pharmacia Biotech)) per well, the cells were washed 3 times with 200 µl of cold PBS. The radioactivity of $^{14}C$ incorporated into the cells was counted with 100 µl of a liquid scintillator added per well.

Figure 3:
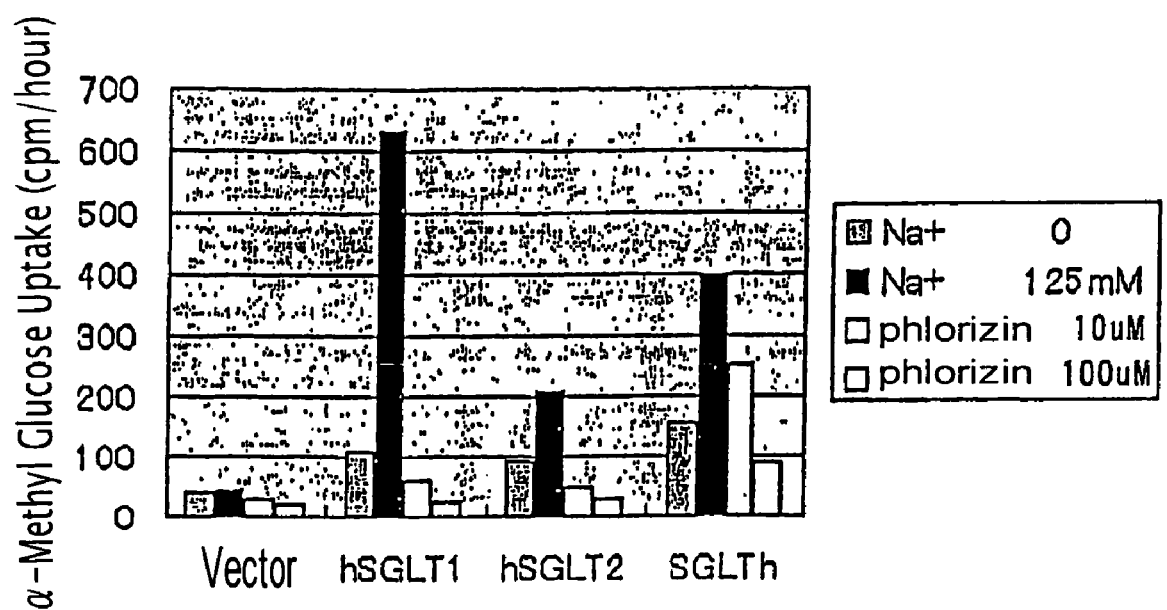
FIG. 3 shows the a-methyl glucose uptake activity of the human SGLT homolog, hSGLT1 and hSGLT2.

As shown in FIG. 3, the results show that the SGLT homolog as well as hSGLT1 and hSGLT2 took in α-methyl glucose in Na concentration-dependent manner, the glucose analog being selectively taken into cells by SGLTs, and that the activity was inhibited by phlorizin, demonstrating that the SGLT homolog has the SGLT function.

Example 6

Cloning of the cDNA Encoding the Mouse Kidney-derived Na+/Glucose Transporter Protein and Determination of the Base Sequence A PCR was carried out using mouse kidney cDNA (CLONTECH) as a template and 2 primers, i.e. primer 11 (SEQ ID NO: 17) and primer 12 (SEQ ID NO: 18). The reaction solution for the PCR contained 1 µl of the said cDNA as the template, 1 µl of Pfu Turbo DNA polymerase (STRATAGENE), 0.5 µM each of primer 11 (SEQ ID NO: 17) and primer 12 (SEQ ID NO: 18), 200 µM dNTPs, and 5 µl of the buffer solution attached to the enzyme product in a total volume of 50 µl. The PCR consisted of a reaction at 94° C. for 1 minute; next 40 cycles of reactions at 96° C. for 20 seconds, at 62° C. for 30 seconds and 72° C. for 2 minutes 30 seconds; and a final elongation reaction at 72° C. for 7 minutes.

The next PCR was carried out using the resulting PCR product as a template and 2 primers, i.e. primer 13 (SEQ ID NO: 19) and primer 14 (SEQ ID NO: 20). The reaction solution for the PCR contained 1 µl of the PCR product as the template, 1 µl of Pfu Turbo DNA polymerase (STRATAGENE), 0.5 µM each of primer 13 (SEQ ID NO: 19) and primer 14 (SEQ ID NO: 20), 200 µM dNTPs, and 5 µl of the buffer solution attached to the enzyme product in a total volume of 50 µl. The PCR consisted of a reaction at 94° C. for 1 minute; next 40 cycles of reactions at 96° C. for 20 seconds, at 62° C. for 30 seconds and 72° C. for 2 minutes 30 seconds; and a final elongation reaction at 72° C. for 7 minutes.

The resulting PCR product and the plasmid vector pME18S were digested overnight at 37° C. with EcoRI and SpeI. After separated by electrophoresis on 1% agarose gel, 2 Kbp DNA fragment (mouse SGLT homolog) and 3 Kbp DNA fragment (pME18S) were excised and extracted with Gel Extraction Kit (Qiagen). The SGLT homolog was subcloned into pME18S using Ligation Kit (Takara). The resulting product was transfected into *E. coli* DH5α, and clones containing the cDNA were selected on LB agar media containing ampicillin. After analysis of the sequence of each clone, a cDNA sequence (SEQ ID NO: 16) encoding a novel Na+/glucose transporter protein was obtained. This novel Na+/glucose transporter protein comprising the amino acid sequence (SEQ ID NO: 15) was referred to as the mouse SGLT homolog, and the transformant was referred to as *Escherichia coli* DH5α/pTB2238.

Figure 4:
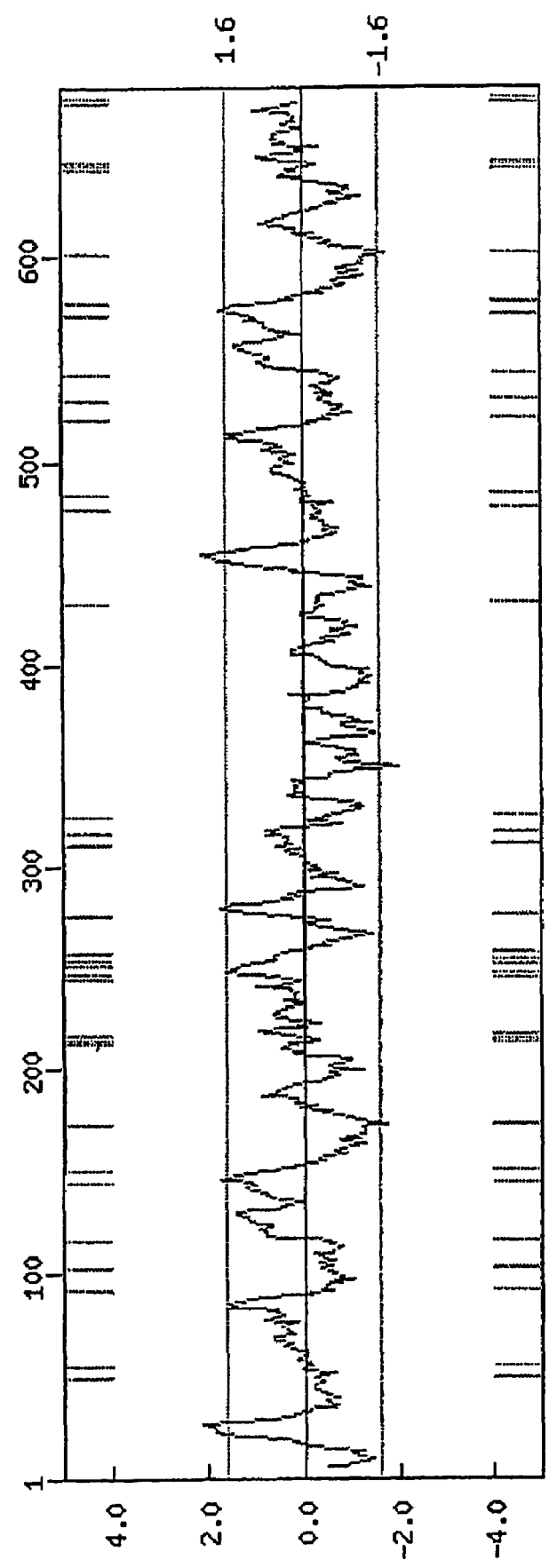
FIG. 4 shows the hydropathy plot of the mouse SGLT homolog.

The hydropathy plot of the mouse SGLT homolog is shown in FIG. 4.

Example 7

Analysis of Distribution of the Expressed Mouse SGLT Homolog Using Taqman PCR

The primers and probe used for Taqman PCR were searched using Primer Express ver. 1.0 (PE Biosystem, Japan) and selected as follows:

```
                                         (SEQ ID NO: 21)
primer 15:    (5'-tgcacagaccaggtgattgtg-3');

(SEQ ID NO: 22)
primer 16:    (5'-gcacggagcctcccttg-3');

(SEQ ID NO: 23)
probe:        (5'-ctcgcagccaacaatctttcacatg-3').
```

A reporter dye FAM (6-carboxyfluorescein) was added to the probe.

The PCR fragment of the mouse SGLT homolog was used as a standard DNA. The reaction solution for the PCR contained 1 µl of pTB2238 DNA as the template, 1 µl of Pfu Turbo DNA polymerase (STRATAGENE), 0.5 µM each of primer 17 (5'-atctctaatgtccagcaatgtg-3', SEQ ID NO: 24) and primer 18 (5'-accagcttggggtaggcaat-3', SEQ ID NO: 25), 200 µM dNTPs, and 5 µl of the buffer solution attached to the enzyme product in a total volume of 50 µl. The PCR consisted of a reaction at 94° C. for 1 minute; next 40 cycles of reactions at 96° C. for 20 seconds, at 62° C. for 30 seconds and 72° C. for 30 seconds; and a final elongation reaction at 72° C. for 7 minutes. The PCR product was subjected to electrophoresis on 2% agarose gel, and 0.9 kbp DNA fragment was excised and extracted with Gel Extraction Kit (Qiagen). The PCR fragment, adjusted in concentrations of $10^0$ to $10^6$ copies/µl, was used as the standard DNA.

Total RNA was extracted as cDNA source from liver, kidney, pancreas, skeletal muscles, white adipose tissue and brown adipose tissue, excised from a 6-week old C57BL/6 mouse (Charles River). The extraction of total RNA was carried out using ISOGEN (Nippon Gene). cDNA was synthesized using 0.1 µg of the thus obtained RNA as a template and TaqMan Reverse Transcription Reagents (Roche). The PCR for the analysis was carried out using 1 µl of the cDNA as a template, 200 nM of primer 15 (SEQ ID NO: 21), 200 nM of primer 16 (SEQ ID NO: 22), and 50 nM of the probe (SEQ ID NO: 23), all of which were added to a given amount of Taqman Universal PCR Master Mix (PE Biosystems, Japan) according to the manufacture's instructions, on ABI PRISM 7700 Sequence Detection System (PE Biosystems, Japan).

The amount of mRNA of each tissue was normalized on the basis of the amount of GAPDH. The PCR for the analysis of GAPDH was carried out using a given amount of TaqMan Rodent GAPDH Control Reagents VIC Probe (Applied Biosystems, Japan) according to the manufacture's instructions as described above, on ABI PRISM 7700 Sequence Detection System.

Figure 5:
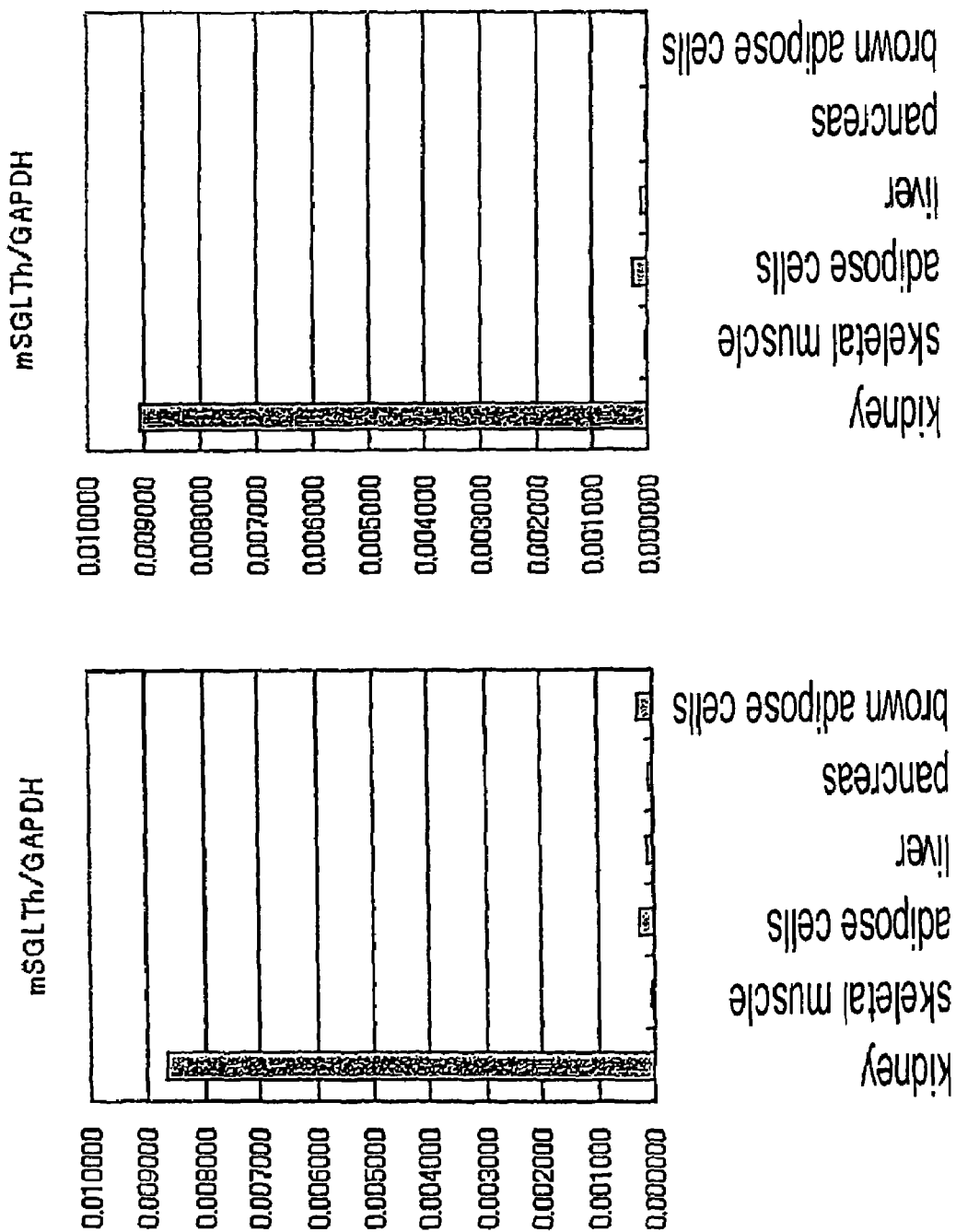
FIG. 5 shows the tissue expression distribution of the mouse SGLT homolog. The MTC panel contains a standardized amount of each cDNA.

The results are shown in FIG. 5. The high expression of the mouse SGLT homolog was observed in kidney.

Example 8

Preparation of Cells Expressing the Mouse SGLT Homolog

The cDNA of human SGLT1 (NCBI Accession NM_000343) was amplified by PCR from Clontech MTC panel kidney cDNA library, and subcloned into the expression vector for animal cells, pME18S between EcoRI and SpeI sites to prepare pME18S-hSGLT1. COS7 cells ($5 \times 10^5$ cells) were transfected with each 1 µg of plasmids pME18S, pME18S-hSGLT1, and pME18S-mouse-SGLT-homolog according to the FuGENE6 method (Roche).

Example 9

Quantification of Glucose Uptake

Experimental incorporation of α-methyl glucose into the COS7 cell having pMEI 8S, the COS7 cell expressing hSGLT1, and the COS7 cell expressing the mouse SGLT homolog was carried out according to the method described in Am. J. Physiol. 270:G833-G843 (1996) and J. Clin. Invest. 93:397-404,1994. These cells were plated on a 96-well plate in a cell density of $3 \times 10^4$ cells/well and in a volume of 100 µl of DMEM containing 10% FBS per well, and cultured overnight at 37° C. The cells were washed 3 times with 150 µl of a buffer solution (125 mM KCl, 1.2 mM $KH_2PO_4$, 2.5 mM $CaCl_2$, 1.2 mM $MgSO_4$, 4 mM Glutamine, 10 mM HEPES (pH 7.2), 0.1 mg/ml BSA), and cultured for an hour in the same buffer solution to remove the rest of glucose. The buffer solution was removed and replaced with 90 µl of the same buffer solution or the buffer solution containing NaCl, or NaCl +100 µM phlorizin (Sigma), or NaCl +1 mM phlorizin in place of KCl. After one-hour incubation with 10 µl of 1 mM α-methyl glucose (containing 0.02 µCi of [$^{14}$C]-α-methyl glucose (Amersham Pharmacia Biotech)) per well, the cells were washed 3 times with 200 µl of cold PBS. The radioactivity of $^{14}$C incorporated into the cells was counted with 100 µl of a liquid scintillator added per well.

Figure 6:
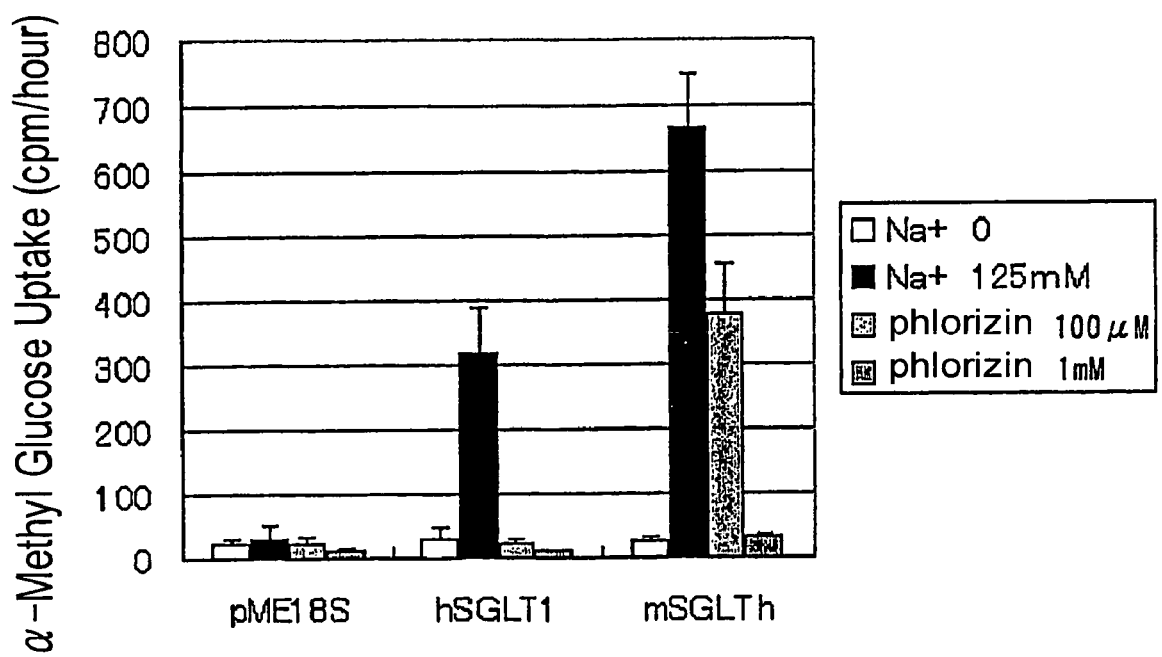
FIG. 6 shows the α-methyl glucose uptake activity of the mouse SGLT homolog, hSGLT1 and hSGLT2.

As shown in FIG. 6, the results show that the mouse SGLT homolog as well as hSGLT1 took in α-methyl glucose in $Na^+$-dependent manner, the glucose analog being selectively taken into cells by SGLTs, and that the activity was inhibited by phlorizin, demonstrating that the mouse SGLT homolog has the SGLT function.

Example 10

Cloning of the cDNA Encoding the Rat Kidney-derived Na+/Glucose Transporter Protein and Determination of the Base Sequence A PCR was carried out using rat kidney cDNA (CLONTECH) as a template and 2 primers, i.e. primer 19 (SEQ ID NO: 28) and primer 20 (SEQ ID NO: 29). The reaction solution for the PCR contained 1 µl of the said cDNA as the template, 1 µl of Pfu Turbo DNA polymerase (STRATAGENE), 0.5 µM each of primer 19 (SEQ ID NO: 28) and primer 20 (SEQ ID NO: 29), 200 µM dNTPs, and 5 µl of the buffer solution attached to the enzyme product in a total volume of 50 µl. The PCR consisted of a reaction at 94° C. for 1 minute; next 40 cycles of reactions at 96° C. for 20 seconds, at 62° C. for 30 seconds and 72° C. for 2 minutes 30 seconds; and a final elongation reaction at 72° C. for 7 minutes.

The next PCR was carried out using the resulting PCR product as a template and 2 primers, i.e. primer 21 (SEQ ID NO: 30) and primer 22 (SEQ ID NO: 31). The reaction solution for the PCR contained 1 µl of the PCR product as the template, 1 µl of Pfu Turbo DNA polymerase (STRATAGENE), 0.5 µM each of primer 21 (SEQ ID NO: 30) and primer 22 (SEQ ID NO: 31), 200 µM dNTPs, and 5 µl of the buffer solution attached to the enzyme product in a total volume of 50 µl. The PCR consisted of a reaction at 94° C. for 1 minute; next 40 cycles of reactions at 96° C. for 20 seconds, at 62° C. for 30 seconds and 72° C. for 2 minutes 30 seconds; and a final elongation reaction at 72° C. for 7 minutes.

The resulting PCR product and the plasmid vector pME18S were digested overnight at 37° C. with EcoRI and SpeI. After separated by electrophoresis on 1% agarose gel, 2 Kbp DNA fragment (rat SGLT homolog) and 3 Kbp DNA fragment (pME18S) were excised and extracted with Gel Extraction Kit (Qiagen). The SGLT homolog was subcloned into pME18S using Ligation Kit (Takara). The resulting product was transfected into *E. coli* DH5α, and clones containing the cDNA were selected on LB agar media containing ampicillin. After analysis of the sequence of each clone, a cDNA sequence (SEQ ID NO: 27) encoding a novel Na+/glucose transporter protein was obtained. This novel Na+/glucose transporter protein comprising the amino acid sequence (SEQ ID NO: 26) was referred to as the rat SGLT homolog, and the transformant was referred to as *Escherichia coli* DH5α/pTB2239.

Figure 7:
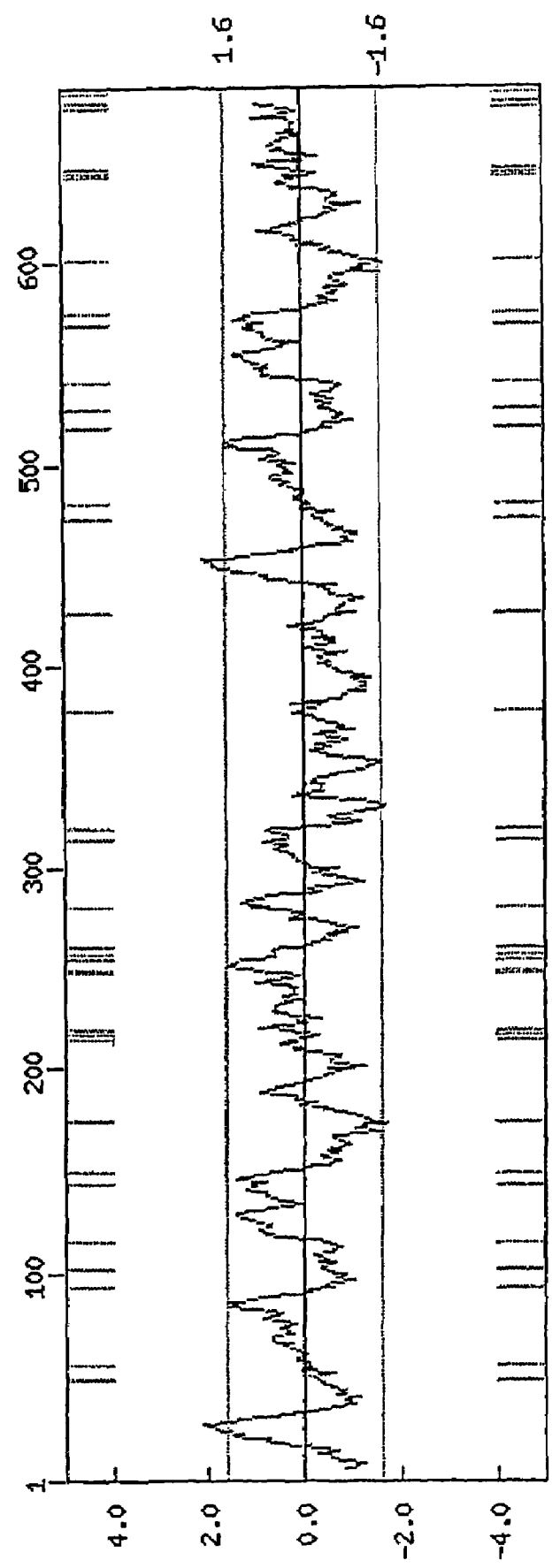
FIG. 7 shows the hydropathy plot of the rat SGLT homolog.

The hydropathy plot of the rat SGLT homolog is shown in FIG. 7.

Example 11

Analysis of Distribution of the Expressed Rat SGLT Homolog Using Taqman PCR

The primers and probe used for Taqman PCR were searched using Primer Express ver. 1.0 (PE Biosystem, Japan) and selected as follows:

```
                                    (SEQ ID NO: 32)
    primer 23:   (5'-ctcacagtcttggccacctg-3');

(SEQ ID NO: 33)
    primer 24:   (5'-agaaccggctctctctggag-3');

(SEQ ID NO: 34)
    probe:       (5'-tgcacggaccaggtgattgtgc-3').
```

A reporter dye FAM (6-carboxyfluorescein) was added to the probe.

The PCR fragment of the rat SGLT homolog was used as a standard DNA. The reaction solution for the PCR contained 1 µl of pTB2239 DNA as the template, 1 µl of Pfu Turbo DNA polymerase (STRATAGENE), 0.5 µM each of primer 25 (5'-tctggagtcagcctgcacacct-3', SEQ ID NO: 35) and primer 26 (5'-cagccttctcagctgggctcag-3', SEQ ID NO: 36), 200 µM dNTPs, and 5 µl of the buffer solution attached to the enzyme product in a total volume of 50 µl. The PCR consisted of a reaction at 94° C. for 1 minute; next 40 cycles of reactions at 96° C. for 20 seconds, at 62° C. for 30 seconds and 72° C. for 30 seconds; and a final elongation reaction at 72° C. for 7 minutes. The PCR product was subjected to electrophoresis on 2% agarose gel, and 0.9 kbp DNA fragment was excised and extracted with Gel Extraction Kit (Qiagen). The PCR fragment, adjusted in concentrations of $10^0$ to $10^6$ copies/µl, was used as the standard DNA.

Sprague-Dawley Rat Poly A$^+$ RNA (CLONTECH)(Brain, Heart, Kidney, Liver, Lung, Pancreas, Retina, Skeletal Muscle, Smooth muscle, Spleen, and Testis) was used as cDNA sources of each tissue. cDNA was synthesized using 0.1 µg of the above RNA as a template and TaqMan Reverse Transcription Reagents (Roche). The PCR for the analysis was carried out using 1 µl of the cDNA as a template, 200 nM of primer 23 (SEQ ID NO: 32), 200 nM of primer 24 (SEQ ID NO: 33), and 50 nM of the probe (SEQ ID NO: 34), all of which were added to a given amount of Taqman Universal PCR Master Mix (PE Biosystems, Japan) according to the manufacture's instructions, on ABI PRISM 7700 Sequence Detection System (PE Biosystems, Japan).

The amount of mRNA of each tissue was normalized on the basis of the amount of GAPDH. The PCR for the analysis of GAPDH was carried out using a given amount of TaqMan Rodent GAPDH Control Reagents VIC Probe (Applied Biosystems, Japan) according to the manufacture's instructions as described above, on ABI PRISM 7700 Sequence Detection System.

Figure 8:
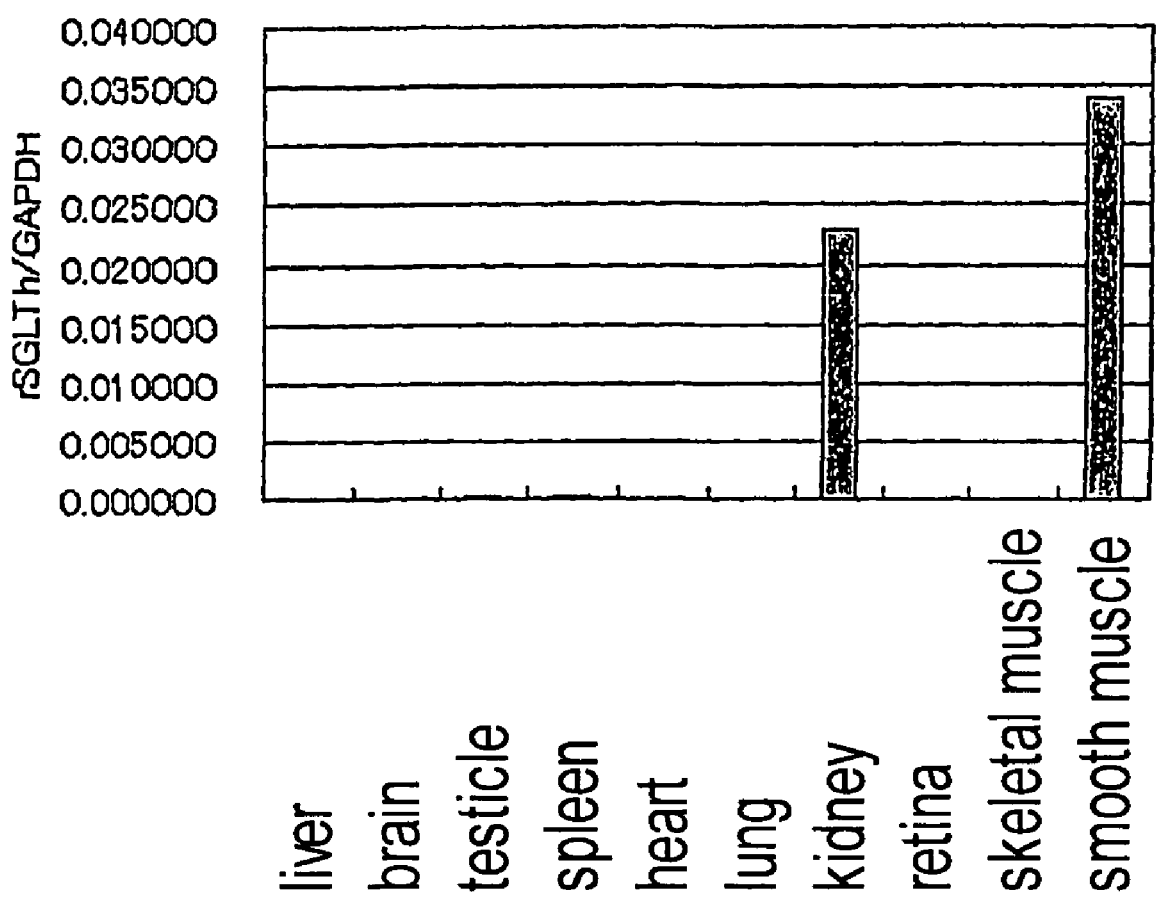
FIG. 8 shows the tissue expression distribution of the rat SGLT homolog. The MTC panel contains a standardized amount of each cDNA.

The results are shown in FIG. 8. The high expression of the rat SGLT homolog was observed in kidney and smooth muscle.

Example 12

Preparation of Cells Expressing the Rat SGLT Homolog

The cDNA of human SGLT1 (NCBI Accession NM_000343) was amplified by PCR from Clontech MTC panel kidney cDNA library, and subcloned into the expression vector for animal cells, pME18S between EcoRI and SpeI sites to prepare pME18S-hSGLT1. COS7 cells ($5\times10^5$ cells) were transfected with each 1 µg of plasmids pME18S, pME18S-hSGLT1, and pME18S-rat-SGLT-homolog according to the FuGENE6 method (Roche).

Example 13

Quantification of Glucose Uptake

Experimental incorporation of α-methyl glucose into the COS7 cell having pME18S, the COS7 cell expressing hSGLT1, and the COS7 cell expressing the rat SGLT homolog was carried out according to the method described in Am. J. Physiol. 270:G833-G843 (1996) and J. Clin. Invest. 93:397-404, 1994. These cells were plated on a 96-well plate in a cell density of $3\times10^4$ cells/well and in a volume of 100 µl of DMEM containing 10% FBS per well, and cultured overnight at 37° C. The cells were washed 3 times with 150 µl of a buffer solution (125 mM KCl, 1.2 mM KH$_2$PO$_4$, 2.5 mM CaCl$_2$, 1.2 mM MgSO$_4$, 4 mM Glutamine, 10 mM HEPES (pH 7.2), 0.1 mg/ml BSA), and cultured for an hour in the same buffer solution to remove the rest of glucose. The buffer solution was removed and replaced with 90 µl of the same buffer solution or the buffer solution containing NaCl, or NaCl +100 µM phlorizin (Sigma), or NaCl +1 mM phlorizin in place of KCl. After one-hour incubation with 10 µl of 1 mM α-methyl glucose (containing 0.02 µCi of [$^{14}$C]-α-methyl glucose (Amersham Pharmacia Biotech)) per well, the cells were washed 3 times with 200 µl of cold PBS. The radioactivity of $^{14}$C incorporated into the cells was counted with 100 µl of a liquid scintillator added per well.

Figure 9:
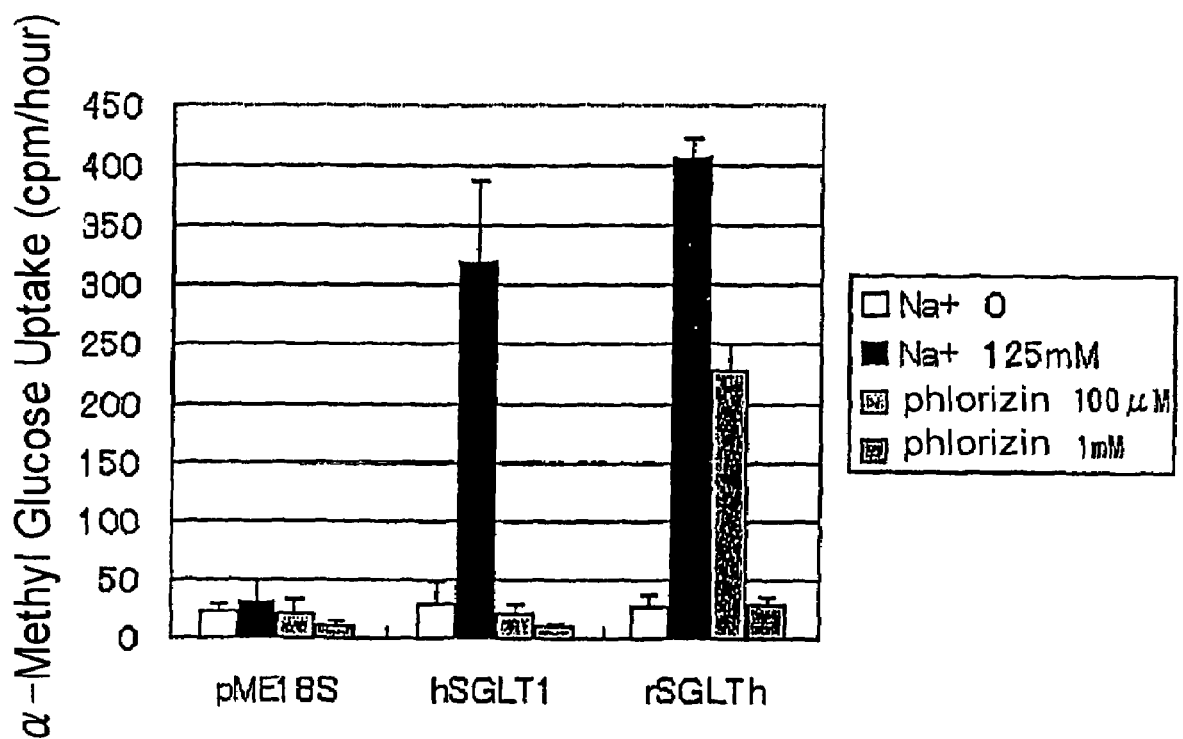
FIG. 9 shows the α-methyl glucose uptake activity of the rat SGLT homolog, hSGLT1 and hSGLT2.

As shown in FIG. 9, the results show that the rat SGLT homolog as well as hSGLT1 took in α-methyl glucose in Na$^+$-dependent manner, the glucose analog being selectively taken into cells by SGLTs, and that the activity was inhibited by phlorizin, demonstrating that the rat SGLT homolog has the SGLT function.

Example 14

Production of a Peptide Antibody Against the Human SGLT Homolog

The used immunogen peptide is a peptide having the amino acid sequence from the residues 261 to 275 of the human SGLT homolog and a cysteine residue added to the 275th residue (SEQ ID NO: 37). N-(γ-maleimidobutyryloxy)succinimide (GMBS) was mixed and reacted with Keyhole Limpet Hemocyanin (KLH) for 40 min at room temperature. KLH having the introduced maleimido groups was fractionated by Sephadex G-25 column. The immunogen peptide (5 mg) was mixed and reacted with the equal amount of the KLH having the introduced maleimido groups at 4° C. for one day. The reaction product was dialyzed against PBS buffer for 2 days, and suspended in PBS buffer in a concentration of 1 mg/ml.

Equal volumes of Freund's complete adjuvant and the antigen were mixed (0.6 ml in total), and a 3-month old New Zealand white rabbit was immunized subcutaneously with the mixture. Then, the rabbit was boosted 3 times every 2 to 3 weeks with the equal amount of the immunogen with Freund's incomplete adjuvant.

The synthetic peptide (5 mg) was coupled to Sulfo-Link gel (5 ml) through cysteine bond, and equilibrated with PBS buffer. The antiserum (5 ml) was passed through the gel coupled to the peptide, and then washed 3 times with PBS buffer (5 ml). The antibody bound to the peptide was eluted with 8 ml of 0.1N glycine/HCl buffer solution (pH 2.5). The eluate was neutralized with 2.4 ml of Tris buffer to give the peptide antibody against the human SGLT homolog.

Example 15

Western Blotting with the Peptide Antibody Against the Human SGLT Homolog

The CHO cell expressing the human SGLT homolog, the CHO cell expressing hSGLT1, the CHO cell expressing hSGLT2, and the CHO cell having pME18S were subjected to western blotting analysis using the peptide antibody against the human SGLT homolog. These cells were plated on 6-well plates in a cell density of $1\times10^5$ cells/2 ml of MEMα containing 10% FBS per well, and cultured overnight at 37° C. These cells were suspended in a buffer (62.5 mM Tris (pH 6.8), 2% SDS) and disrupted by ultra-sonication. To the disrupted cells, 5% volume of 2-mercaptoethanol and 10% volume of glycerol were added, boiled for 5 min and then cooled on ice.

Respective samples (equivalent to 50 µg) were subjected to SDS-PAGE on 7.5% acrylamide gel. After the electrophoresis, proteins on the gel were transferred onto a nitrocellulose membrane (BIO-RAD) according to the semidry transfer method. After the transfer, the nitrocellulose membrane was incubated overnight at 4° C. in TBST buffer solution (10 mM Tris (pH 7.5), 150 mM NaCl, 0.05% Tween20) containing 5% skim milk.

The first antibody solution was made by diluting 50 times the peptide antibody against the human SGLT homolog with TBST buffer solution, and the membrane was incubated in the antibody solution for 4 hours at room temperature. After the membrane was washed 5 times with TBST buffer, to the membrane, added was an anti-rabbit IgG antibody-HRP (Amersham-Pharmacia) as the second antibody, which was diluted 10000 times with TBST buffer. After incubation for an hour at room temperature, the membrane was washed 5 times with TBST buffer. The membrane was then incubated for a minute in Renaissance™ luminol Western Blot Chemiluminescence Reagent Plus (NEN life science) solution, and exposed to an X-ray film, which was then developed.

Figure 10:
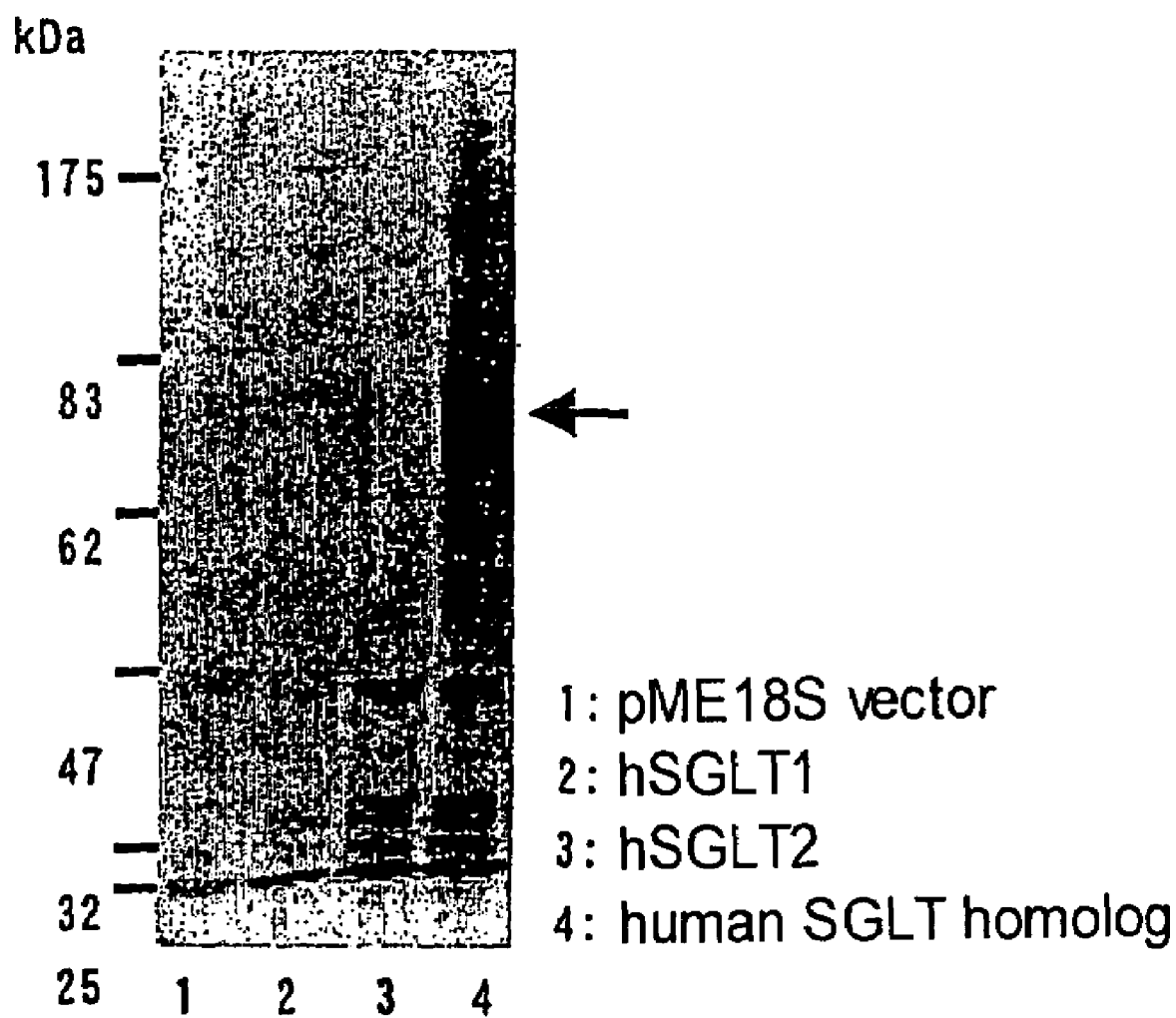
FIG. 10 shows the western blot analysis using the peptide antibody to the human SGLT homolog.

The result is shown in FIG. 10, demonstrating that the peptide antibody against the human SGLT homolog specifically recognizes the human SGLT homolog indicated by an arrow.

Example 16

Immunostaining of Human Pancreas and Liver Slices with the Peptide Antibody to the Human SGLT Homolog.

The PCR analysis shows that the SGLT homolog gene is highly expressed in pancreas, liver and kidney in a human. Thus, in order to select an organ to be targeted for development of a diabetic medicine using the SGLT homolog gene, and to make clear the function of the gene, human normal pancreas and liver were examined for the expression of the SGLT homolog gene through the immunostaining using the polyclonal antibody to the human SGLT homolog (Kurabo Industries Ltd).

Tissue samples of human normal pancreas and liver were purchased from BioChain Inc., mounted on the slide glasses, being commercially available and ethical problem-free. Some of the slices were deparaffinized, stained with hematoxylin/eosin and embedded in a conventional manner for the morphological observation (Sosikigaku Kenkyuhou (Histological protocols), Yutaka SANO, published by Nanzan-Dou, 1985). Further, an almost complete series of slices with the same lot number were immunostained using the polyclonal antibody to the human SGLT homolog. The tissues mounted on slide glasses were deparaffinized and then immunostained. The immunostaining was carried out using Vecstain ABC Kit (peroxidase method, Vector Lab) and DAB as the substrate for coloring, according to the manufacture's protocol attached to the kit.

The expression of the SGLT homolog gene was detected highly in acinous cells in case of pancreas, and detected generally throughout hepatic parechymal cells in case of liver. The expression in hepatic parechymal cells shows no polarity.

Example 17

Preparation of Expression Vectors for SNPs of the Human SGLT Homolog

Figure 11:
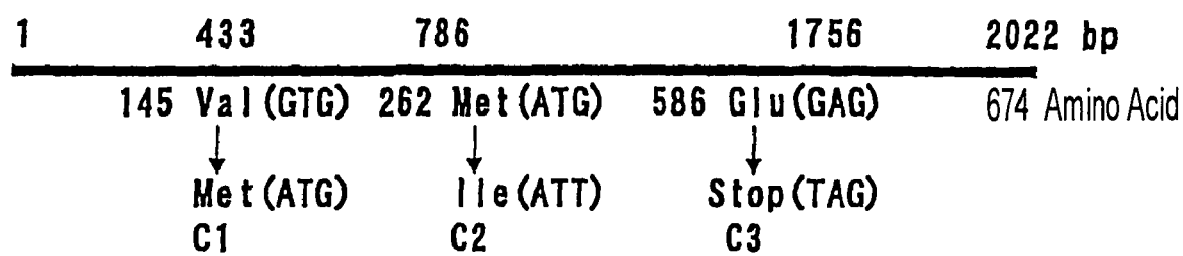
FIG. 11 shows the SNPs in the human SGLT homolog structural gene.

After the Celela's SNP Database was searched for the structure gene of the human SGLT homolog, 3 different SNPs were found (FIG. 11). The base substitution G433A, referred to SNP C1, causes the amino acid substitution Val145Met. The base substitution G786T, referred to SNP C2, causes the amino acid substitution Met262Ile. The base substitution G1756T, referred to SNP C3, causes the amino acid substitution Glu586Stop.

The base substitutions of SNP C1 and C2 were introduced into pME18S-human-SGLT-homolog (pTB2193) DNA using QuickChange XL Site-Directed Mutagenesis Kit (STRATAGENE). The reaction solution contained 10 ng of pTB2193, 5 µl of the reaction buffer, 125 ng of a primer for C1 mutation (SEQ ID NO: 38) or a primer for C2 mutation (SEQ ID NO: 39), 1 µl of dNTP mix, 3 µl of QuickSolution and a sufficient volume of distilled water for a total volume of 50 µl, to which 1 µl of Pfu Turbo DNA polymerase (2.5U/µl) was added. The PCR consisted of a reaction at 95° C. for 1 minute; next 18 cycles of reactions at 95° C. for 50 seconds, at 60° C. for 50 seconds and 68° C. for 12 minutes; and a final elongation reaction at 68° C. for 7 minutes.

The resulting PCR product was treated with a restriction enzyme, DpnI (10U) for an hour at 37° C. to digest parent methylated DNAs. This product was transfected into *E. coli* XL1-Blue, and clones containing the cDNA were selected on LB agar media containing ampicillin. After analysis of the sequence of each clone, the cDNA sequence (SEQ ID NO: 40) having the C1 base substitution and encoding the amino acid sequence (SEQ ID NO: 41) was obtained. The obtained transformant was referred to as *Escherichia coli* XL1-Blue/pTB2251. In the same way, the cDNA sequence (SEQ ID NO: 42) having the C2 base substitution and encoding the amino acid sequence (SEQ ID NO: 43) was obtained. This transformant was referred to as *Escherichia coli* XL1-Blue/pTB2252.

A PCR was carried out using pME18S-human-SGLT-homolog (pTB2193) DNA as a template and 2 primers, i.e. primer 3 (SEQ ID NO: 5) and a primer for C3 mutation (SEQ ID NO: 44) to introduce the base substitution of SNP C3. The reaction solution for the PCR contained 10 ng of the said cDNA as the template, 1 µl of Pfu Turbo DNA polymerase (STRATAGENE), 0.5 µM each of primer 3 (SEQ ID NO: 5) and a primer for C3 mutation (SEQ ID NO: 44), 200 µM dNTPs, and 5 µl of the buffer solution attached to the enzyme product in a total volume of 50 µl. The PCR consisted of a reaction at 94° C. for 1 minute; next 40 cycles of reactions at 96° C. for 20 seconds, at 62° C. for 30 seconds and 72° C. for 2 minutes 30 seconds; and a final elongation reaction at 72° C. for 7 minutes.

The resulting PCR product and the plasmid vector pME18S were digested overnight at 37° C. with restriction enzymes EcoRI (10U) and SpeI (10U). After separated by electrophoresis on 1% agarose gel, 1.8 Kbp DNA fragment (SGLT homolog) and 3 Kbp DNA fragment (PME18S) were excised and extracted with Gel Extraction Kit (Qiagen). The SGLT homolog having the C3 mutation was subcloned into pME18S using Ligation Kit (Takara). The resulting product was transfected into *E. coli* DH5α, and clones containing the cDNA were selected on LB agar media containing ampicillin. After analysis of the sequence of each clone, the cDNA sequence (SEQ ID NO: 45) having the C3 mutation and encoding the amino acid sequence (SEQ ID NO: 46) was obtained. The transformant was referred to as *Escherichia coli* DH5α/pTB2253.

Example 18

Preparation of Cells Expressing SNPs of the Human SGLT Homolog

Each 1 μg of the expression vectors for animal cells: pME18S, pME18S-hSGLT2, pME18S-human-SGLT-homolog (pTB2193), pME18S-human-SGLT-homolog-SNP-C1 (pTB2251), pME18S-human-SGLT-homolog-SNP-C2 (pTB2252) and pME18S-human-SGLT-homolog-SNP-C3 (pTB2253), and 3 μl of FuGENE 6 (Roche) were added to Opti-MEM (Gibco-BRL) 100 μl for 15 min at room temperature. These mixtures were then added to COS7 cells (1×10$^6$ cells/1 ml of DMEM containing 10% FBS/well in 6-well plate) so that each gene was introduced into the cells.

Example 19

Assay of Glucose Uptake Activity of Cells Expressing SNPs of the Human SGLT Homolog Experimental incorporation of α-methyl glucose into the COS7 cells carrying pME 18S, pME18S-hSGLT2, pME 18S-human-SGLT-homolog (pTB2193), pME18S-human-SGLT-homolog-SNP-C 1 (pTB2251), pME18S-human-SGLT-homolog-SNP-C2 (pTB2252), and pME18S-human-SGLT-homolog-SNP-C3 (pTB2253) was carried out according to the method described in Am. J. Physiol. 270: G833-G843 (1996) and J. Clin. Invest. 93:397-404 (1994).

These gene-transfected cells were cultured for a day, and then plated on a 96-well plate in a cell density of 3×10$^4$ cells/well and in a volume of 100 μl of DMEM containing 10% FBS per well, and further cultured overnight at 37° C. The cells were washed 3 times with 150 μl of a buffer solution (125 mM KCl, 1.2 mM KH$_2$PO$_4$, 2.5 mM CaCl$_2$, 1.2 mM MgSO$_4$, 4 mM Glutamine, 10 mM HEPES (pH 7.2), 0.1 mg/ml BSA), and cultured for an hour in the same buffer solution to remove the rest of glucose. The buffer solution was removed and replaced with 90 μl of the same buffer solution or the buffer solution containing NaCl, or NaCl +100 μM phlorizin (Sigma), or NaCl +1 mM phlorizin in place of KCl. After one-hour incubation with 10 μl of 1 mM α-methyl glucose (containing 0.02 μCi of [$^{14}$C]-α-methyl glucose (Amersham Pharmacia Biotech)) per well, the cells were washed 3 times with 200 μl of cold PBS. The radioactivity of $^{14}$C incorporated into the cells was counted with 100 μl of a liquid scintillator added per well.

Figure 12:
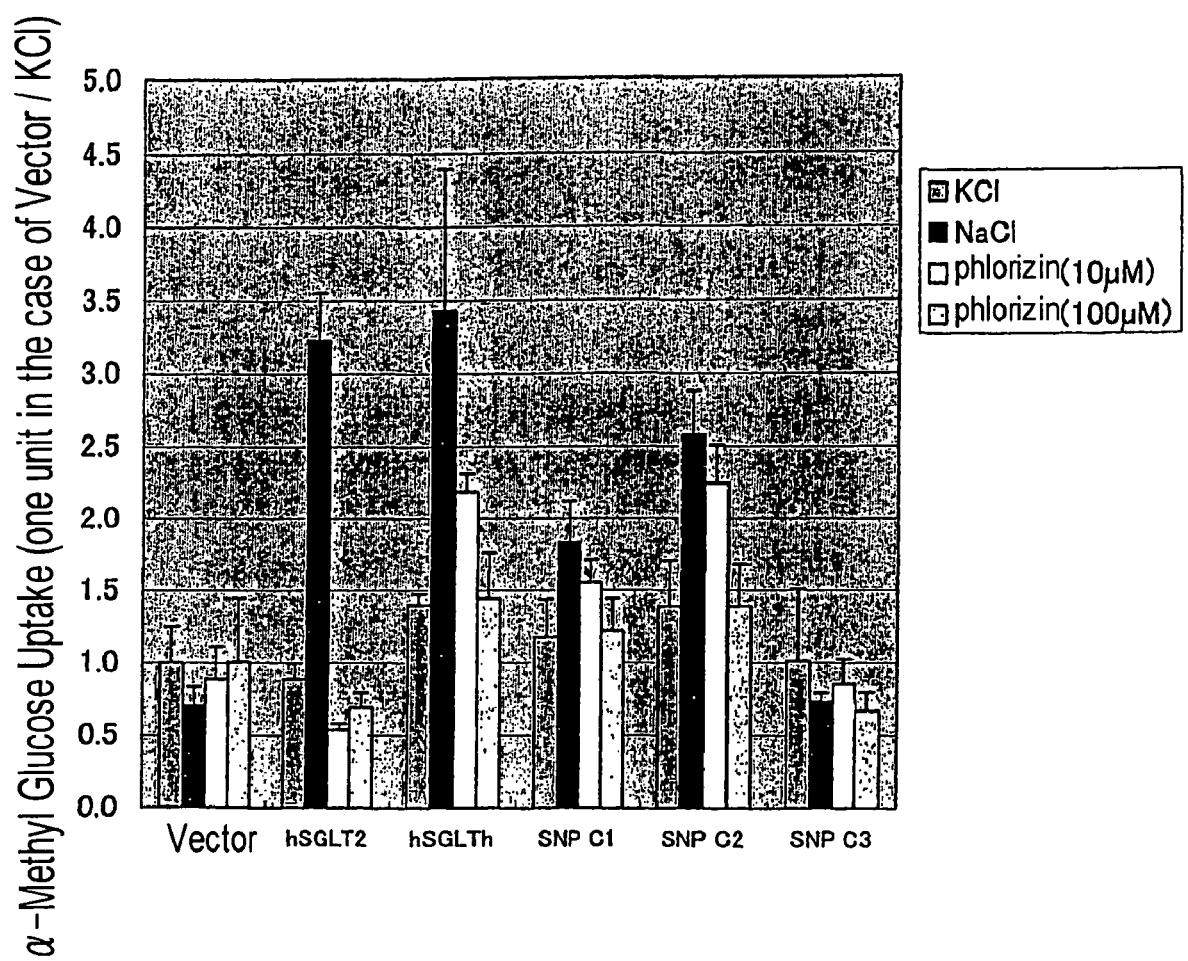
FIG. 12 shows the glucose uptake activity in cells expressing the SNPs of human SGLT homolog, referring to the amount of glucose uptake in COS-7 cells having pME18S vector as one unit.

The results are shown in FIG. 12, with the amount of glucose incorporated into COS-7 cells carrying pME18S vector (KCl) defined as one unit. In the cell expressing the human SGLT homolog, as well as in the cells expressing hSGLT2, the glucose uptake activity was increased in presence of NaCl, and such an activity was inhibited by the specific inhibitor of SGLT, phlorizin. As compared with this, the NaCl-dependent glucose uptake activity in the cell expressing SNP C1 was lower, and the NaCl-dependent glucose uptake activity in the cell expressing SNP C2 was not significantly different. In the cell expressing SNP C3, the NaCl-dependent glucose uptake activity was not observed.

Example 20

Cloning of the Upstream Region of the Human SGLT Homolog Gene and Determination of the Base Sequence A PCR was carried out using human genome genes (CLONTECH) as a template and 2 primers, i.e. primer 27 (SEQ ID NO: 47) and primer 28 (SEQ ID NO: 48). The reaction solution for the PCR contained 1 μl of the said genome DNA as the template, 1 μl of Pfu Turbo DNA polymerase (STRATAGENE), 0.5 μM each of primer 27 (SEQ ID NO: 47) and primer 28 (SEQ ID NO: 48),200 μM dNTPs, and 5 μl of the buffer solution attached to the enzyme product in a total volume of 50 μl. The PCR consisted of a reaction at 94° C. for 1 minute; next 40 cycles of reactions at 96° C. for 20 seconds, at 65° C. for 30 seconds and 72° C. for 4 minutes; and a final elongation reaction at 72° C. for 7 minutes.

A further PCR was carried out using the resulting PCR product as a template and 2 primers, i.e. primer K1 (SEQ ID NO: 49) and primer X1 (SEQ ID NO: 50). The reaction solution for the PCR contained 1 μl of the PCR product as the template, 1 μl of Pfu Turbo DNA polymerase (STRATAGENE), 0.5 μM each of primer K1 (SEQ ID NO: 49) and primer X1 (SEQ ID NO: 50), 200 μM dNTPs, and 5 μl of the buffer solution attached to the enzyme product in a total volume of 50 μl. The PCR consisted of a reaction at 94° C. for 1 minute; next 40 cycles of reactions at 96° C. for 20 seconds, at 65° C. for 30 seconds and 72° C. for 3 minutes; and a final elongation reaction at 72° C. for 7 minutes.

The resulting PCR product and the plasmid vector pGV-B2 (Nippon Gene) for the expression of firefly luciferase were digested overnight at 37° C. with restriction enzymes KpnI (10U) and XhoI (10U). After separated by electrophoresis on 1% agarose gel, 2.3 Kbp DNA fragment (the upstream region of the human SGLT homolog gene) and 4.8 Kbp DNA fragment (pGV-B2) were excised and extracted with Gel Extraction Kit (Qiagen). The upstream region of human SGLT homolog gene was subcloned into pGV-B2 using Ligation Kit (Takara). The resulting product was transfected into *E. coli* DH5α, and clones containing the cDNA were selected on LB agar media containing ampicillin. After analysis of the sequence of each clone, the DNA sequence (SEQ ID NO: 51) of the region from 2261 bp to 8 bp upstream of the translation start point of the human SGLT homolog gene was obtained. The transformant was referred to as *Escherichia coli* DH5α/pTB2254.

Figure 13:
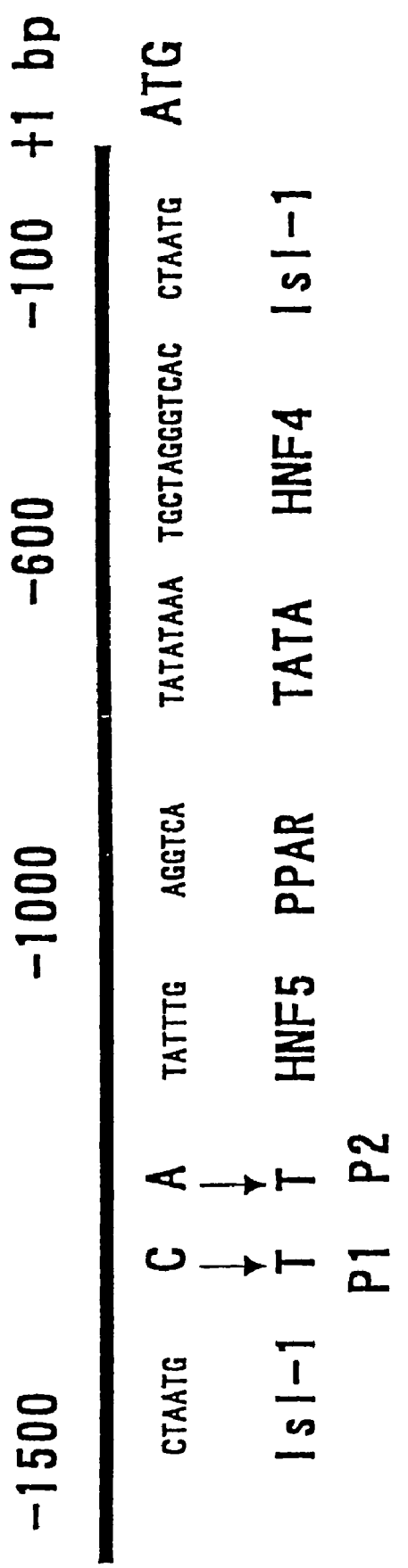
FIG. 13 shows the SNPs in the upstream region of the human SGLT homolog gene.

The DNA sequence of the upstream region of the human SGLT homolog gene contains specific binding sites for transcription factors such as Is11, HNF5, PPAR, and HNF4, and TATA box, which RNA polymerase can be bound to (FIG. 13).

Example 21

Preparation of SNPs of the upstream region of the human SGLT homolog gene

After the Celela's SNP Database was searched for the upstream region of the human SGLT homolog gene, 2 different SNPs were found (FIG. 13). The base substitution of C at 1564 bp upstream of the translation start with T was referred to as SNP-P1, and the base substitution of A at 1438 bp upstream of the translation start with T was referred to as SNP-P2.

The base substitutions of SNP P1 and P2 were introduced into pGV-B2-[upstream region of human SGLT homolog gene] (pTB2254) DNA using QuickChange XL Site-Directed Mutagenesis Kit (STRATAGENE). The reaction solution contained 10 ng of pTB2254, 5 μl of the reaction buffer, 125 ng of a primer for P1 mutation (SEQ ID NO: 52) or a primer for P2 mutation (SEQ ID NO: 53), 1 μl of dNTP mix, 3 μl of QuickSolution and a sufficient volume of distilled water for a total volume of 50 µl, to which 1 µl of Pfu Turbo DNA polymerase (2.5U/µl) was added. The PCR consisted of a reaction at 95° C. for 1 minute; next 18 cycles of reactions at 95° C. for 50 seconds, at 60° C. for 50 seconds and 68° C. for 12 minutes; and a final elongation reaction at 68° C. for 7 minutes.

The resulting PCR product was treated with a restriction enzyme, DpnI (10U) for an hour at 37° C. to digest parent methylated DNAs. This product was transfected into *E. coli* XL1-Blue, and clones containing the plasmid were selected on LB agar media containing ampicillin. After analysis of the sequence of each clone, the DNA sequence (SEQ ID NO: 54) having the P2 base substitution was obtained, and the obtained transformant was referred to as *Escherichia coli* XL1-Blue/pTB2255. The DNA sequence (SEQ ID NO: 55) having the P1 base substitution was obtained, and the obtained transformant was referred to as *Escherichia coli* XL1-Blue/pTB2256. As well, the DNA sequence (SEQ ID NO: 56) having both the P1 and P2 base substitutions was obtained, and the obtained transformant was referred to as *Escherichia coli* DH5α/pTB2257.

Example 22

Preparation of Mutants Having a Deletion in the Upstream Region of the Human SGLT Homolog Gene A PCR was carried out using the upstream region of human SGLT homolog gene (pTB2254) DNA as a template and the following primer-pair sets: primer K2 (SEQ ID NO: 57) and primer X1 (SEQ ID NO: 50); primer K3 (SEQ ID NO: 58) and primer X1 (SEQ ID NO: 50); primer K1 (SEQ ID NO: 49) and primer X2 (SEQ ID NO: 59); and primer K2 (SEQ ID NO: 57) and primer X2 (SEQ ID NO: 59). The reaction solution for the PCR contained 10 ng of pTB2254 DNA as the template, 1 µl of Pfu Turbo DNA polymerase (STRATAGENE), 0.5 µM each primer in each primer set, 200 µM dNTPs, and 5 µl of the buffer solution attached to the enzyme product in a total volume of 50 µl. The PCR consisted of a reaction at 94° C. for 1 minute; next 40 cycles of reactions at 96° C. for 20 seconds, at 65° C. for 30 seconds and 72° C. for 3 minutes; and a final elongation reaction at 72° C. for 7 minutes.

The resulting PCR product and the plasmid vector pGV-B2 (Nippon Gene) for the expression of firefly luciferase were digested overnight at 37° C. with restriction enzymes KpnI (10U) and XhoI (10U). After separated by electrophoresis on 1% agarose gel, 1.3 Kbp DNA fragment (K2X1), 450 bp DNA fragment (K3X1), 1.8 Kbp DNA fragment (K1X2), 0.8 Kbp DNA fragment (K2X2), and 4.8 Kbp DNA fragment (pGV-B2) were excised and extracted with Gel Extraction Kit (Qiagen). These upstream regions of human SGLT homolog gene were subcloned into pGV-B2 using Ligation Kit (Takara). The resulting products were transfected into *E. coli* DH5α, and clones containing the DNAs were selected on LB agar media containing ampicillin. After analysis of the sequence of each clone, the DNA sequences of the upstream region of the human SGLT homolog gene, i.e. K2X1, K3X1, K1X2, K2X2 were obtained (FIG. 14).

Example 23

Preparation of the Cells Transfected with a Plasmid Containing the Upstream Region of Human SGLT Homolog Gene and a Reporter Gene Each (0.5 µg) of the plasmid vector pGV-B2 (Nippon Gene) for the expression of firefly luciferase, which is lacking in a promoter; the plasmid vector pGV-C2 (Nippon Gene) for the expression of firefly luciferase, which has the SV40 early enhancer/promoter; and the plasmids having the upstream regions of human SGLT homolog gene and the reporter gene: K1X1(CA), K1X1(CT), K1X1(TA), K1X1(TT), K2X1, K3X1, K1X2, K2X2 was added to Opti-MEM (Gibco-BRL) 50 µl together with 3 µl of FuGENE 6 (Roche) and pRL-TK (0.5 µg) (expressing seapansy luciferase under control of herpes simplex virus thymidine kinase promoter; Nippon Gene) as the internal control for standardization. After incubated for 15 min at room temperature, each sample was added to 4 wells containing the human hepatic cancer cell line, HepG2 cells ($1\times10^5$ cells/0.2 ml of DMEM containing 10% FBS/well) in 48-well plate in an amount of 10 µl/well for the gene transfection, and these cells were cultured for 2 days.

The promoter activity was determined using PicaGene Dual/SeaPansy Kit (Nippon Gene). These HepG2 cells were washed two times with PBS (200 µl), and then shook with 30 µl/well of the Cell Lysis Buffer attached to the Kit for 15 min at room temperature. An aliquot (10) of the Cell Lysis Buffer from each well was transferred to 96-well Fluoro-Black plate (DAINIPPON Pharmaceutical Co.). Luminescence due to the luciferase was quantified using Luminoskan RS (Labsystems). The firefly luciferase activity was determined by quantifying luminescence for 5 seconds at the delay time of 1 second after addition of 50 µl of PicaGene Luminescence Reagent II to each well. Then, the seapansy luciferase activity was determined by quantifying luminescence for 5 seconds at the delay time of 1 second after addition of 50 µl of Seapansy Luminescence Reagent to each well.

Figure 15:
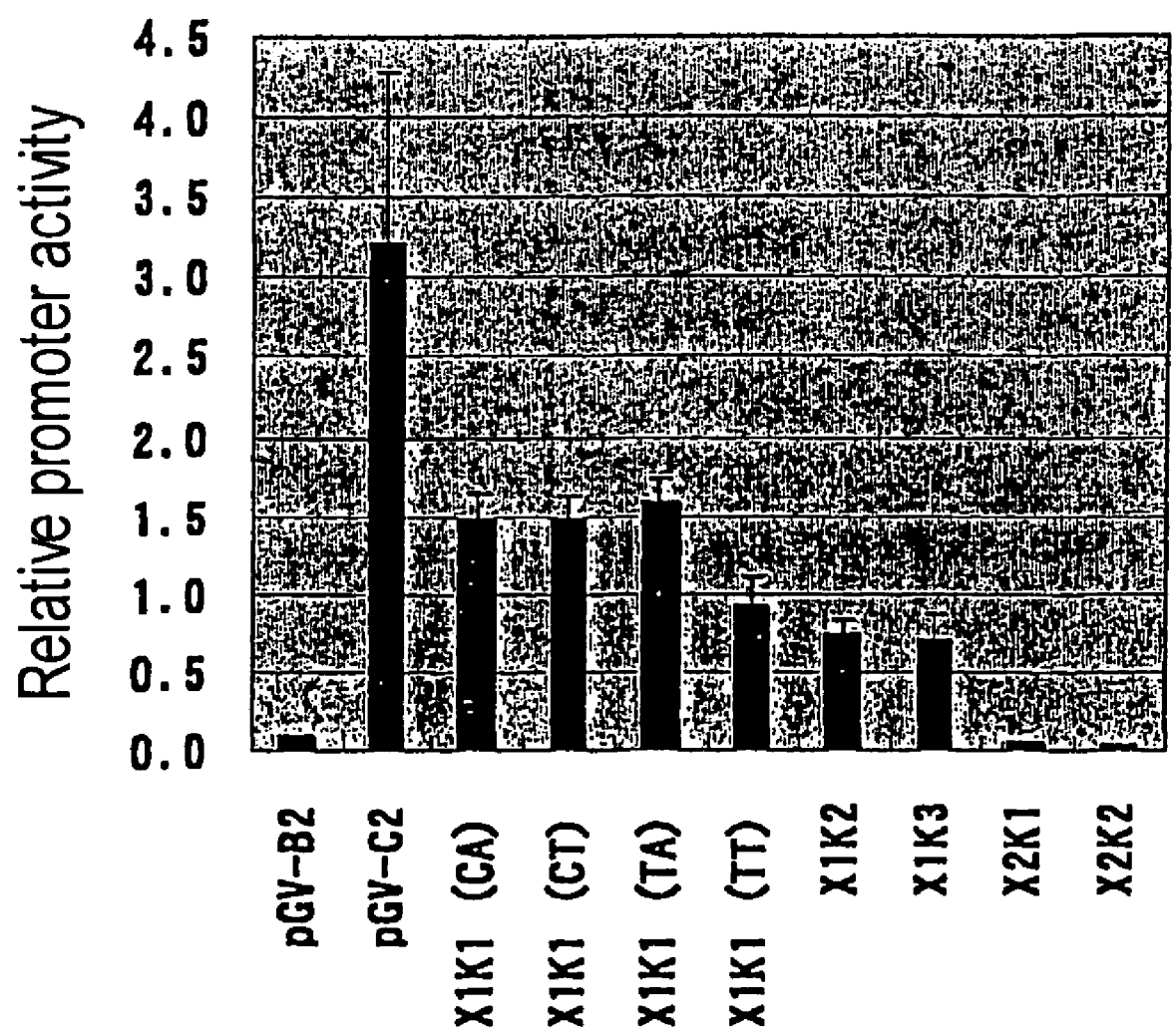
FIG. 15 shows the promoter activity in the upstream region of the human SGLT homolog gene, referring to the activity of Seapansy luciferase as one unit.

The promoter activity was expressed in a ratio of the firefly luciferase activity to the seapansy luciferase activity (FIG. 15) for each well. The results indicate that X1K3 region is essential for the promoter activity of the human SGLT homolog; addition of K1K3 region further enhance the promoter activity; and that there are no difference in the prompter activity among CA-, CT-, and TA-type SNPs, but TT-type SNP shows lower activity.

Example 24

Analysis of SNPs of the Human SGLT Homolog

The SNPs in the promoter of the human SGLT homolog are SNP-P1 and SNP-P2, and the SNPs in the structure gene of the human SGLT homolog are SNP-C1, SNP-C2 and SNP-C3. The base sequences of all the SNPs were confirmed by the direct sequencing of respective PCR fragments.

The reaction solution for the PCR contained 200 ng of the human genome DNA (BCP) as the template, 1 µl of Pfu Turbo DNA polymerase (STRATAGENE), 200 µM dNTPs, 5 µl of the buffer solution attached to the enzyme product, and 0.5 µM each of primer 29 (SEQ ID NO: 60) and primer 30 (SEQ ID NO: 61) for SNP-P1 and P2 in a total volume of 50 µl. Similarly used were primer 32 (SEQ ID NO: 63) and primer 33 (SEQ ID NO: 64) for SNP-C1; primer 35 (SEQ ID NO: 66) and primer 36 (SEQ ID NO: 67) for SNP-C2; and primer 38 (SEQ ID NO: 69) and primer 39 (SEQ ID NO: 70) for SNP-C3. Each PCR consisted of a reaction at 94° C. for 1 minute; next 40 cycles of reactions at 96° C. for 20 seconds, at 57° C. for 30 seconds and 72° C. for 30 seconds; and a final elongation reaction at 72° C. for 7 minutes.

After the resulting PCR product was subjected to electrophoresis on 2% agarose gel, 500 bp DNA fragment was excised and extracted with Gel Extraction Kit (Qiagen) in a final volume of 30 μl. To 5 μl of each extracted DNA, 4 μl of 5× Sequencing Buffer (PE Biosystems, Japan), 4 μl of BigDye Terminator RR Mix (PE Biosystems, Japan) and 3.2 pmol of primer 31 (SEQ ID NO: 62) for SNP-P 1 and P2 were added in a total volume of 20 μl. Similarly used were primer 34 (SEQ ID NO: 65) for SNP-C1; primer 37 (SEQ ID NO: 68) for SNP-C2; and primer 40 (SEQ ID NO: 71) for SNP-C3.

Figure 16:
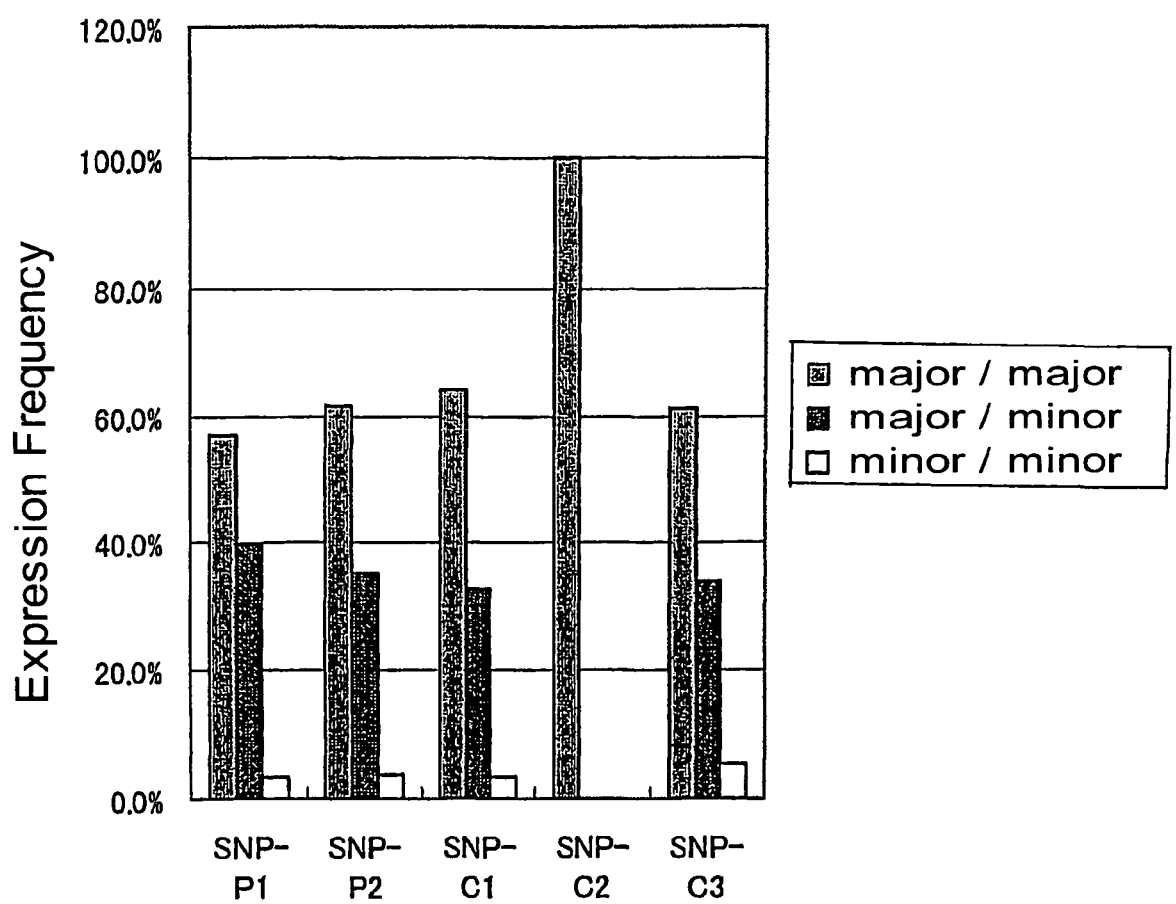
FIG. 16 shows the expression frequency of the SNPs of the human SGLT homolog in healthy subjects (average age=42.3, n=58). The major means C and the minor means T in SNP-P1; the major means A and the minor means T in SNP-P2; the major means G and the minor means A in SNP-C 1; the major means G and the minor means T in SNP-C2; and the major means G and the minor means T in SNP-C3.

For the sequence determination, carried out were a reaction at 94° C. for 1 minute; next 25 cycles of reactions at 96° C. for 10 seconds, at 50° C. for 5 seconds and 60° C. for 4 minutes; and a final elongation reaction at 72° C. for 7 minutes. The reaction products were purified through Sephadex-G50 superfine (Amersham-Pharmacia), and then heated at 100° C. for 3 minutes and cooled on ice. The base sequences of the SNP sites were determined using ABI 3700 Autosequencer. The results are shown in FIG. 16, confirming the expression of the SNPs in 58 healthy subjects, except for SNP-C2.

INDUSTRIAL APPLICABILITY

The proteins having the same or substantially the same amino acid sequence as the amino acid sequence represented by SEQ ID NO: 1, 15 or 26 are useful as a diagnostic marker for a disease such as diabetes. The compounds enhancing or inhibiting the activity of the proteins, obtained the screening method using the proteins, can be used as a prophylactic and/or therapeutic agent for a disease such as diabetes and hyperlipidemia.

The invention claimed is:

1. An isolated protein comprising the amino acid sequence of SEQ ID NO: 1, or a salt thereof.

2. The portein according to claim 1, which consists of the amino acid sequence of SEQ ID NO: 1, or a salt thereof.

3. A composition comprising the protein according to claim 1, or a salt thereof and a pharmaceutically acceptable carrier, excipient or diluent.

4. A kit for screening for a compound or a salt thereof that enhances or inhibits the glucose transporter activity of the protein according to claim 1, comprising the protein according to claim 1.

* * * * *

SEQUENCE LISTING

```
<160> NUMBER OF SEQ ID NOS: 71

<210> SEQ ID NO 1
<211> LENGTH: 674
<212> TYPE: PRT
<213> ORGANISM: Human

<400> SEQUENCE: 1

Met Gly Pro Gly Ala Ser Gly Asp Gly Val Arg Thr Glu Thr Ala Pro
 1               5                  10                  15

His Ile Ala Leu Asp Ser Arg Val Gly Leu His Ala Tyr Asp Ile Ser
             20                  25                  30

Val Val Val Ile Tyr Phe Val Phe Val Ile Ala Val Gly Ile Trp Ser
         35                  40                  45

Ser Ile Arg Ala Ser Arg Gly Thr Ile Gly Gly Tyr Phe Leu Ala Gly
     50                  55                  60

Arg Ser Met Ser Trp Trp Pro Ile Gly Ala Ser Leu Met Ser Ser Asn
 65                  70                  75                  80

Val Gly Ser Gly Leu Phe Ile Gly Leu Ala Gly Thr Gly Ala Ala Gly
                 85                  90                  95

Gly Leu Ala Val Gly Gly Phe Glu Trp Asn Ala Thr Trp Leu Leu Leu
            100                 105                 110

Ala Leu Gly Trp Val Phe Val Pro Val Tyr Ile Ala Ala Gly Val Val
        115                 120                 125

Thr Met Pro Gln Tyr Leu Lys Lys Arg Phe Gly Gly Gln Arg Ile Gln
    130                 135                 140

Val Tyr Met Ser Val Leu Ser Leu Ile Leu Tyr Ile Phe Thr Lys Ile
145                 150                 155                 160

Ser Thr Asp Ile Phe Ser Gly Ala Leu Phe Ile Gln Met Ala Leu Gly
                165                 170                 175

Trp Asn Leu Tyr Leu Ser Thr Gly Ile Leu Leu Val Val Thr Ala Val
            180                 185                 190

Tyr Thr Ile Ala Gly Gly Leu Met Ala Val Ile Tyr Thr Asp Ala Leu
        195                 200                 205

Gln Thr Val Ile Met Val Gly Gly Ala Leu Val Leu Met Phe Leu Gly
    210                 215                 220

Phe Gln Asp Val Gly Trp Tyr Pro Gly Leu Glu Gln Arg Tyr Arg Gln
225                 230                 235                 240

Ala Ile Pro Asn Val Thr Val Pro Asn Thr Thr Cys His Leu Pro Arg
```

-continued

```
                245                 250                 255
Pro Asp Ala Phe His Met Leu Arg Asp Pro Val Ser Gly Asp Ile Pro
                260                 265                 270

Trp Pro Gly Leu Ile Phe Gly Leu Thr Val Leu Ala Thr Trp Cys Trp
            275                 280                 285

Cys Thr Asp Gln Val Ile Val Gln Arg Ser Leu Ser Ala Lys Ser Leu
        290                 295                 300

Ser His Ala Lys Gly Gly Ser Val Leu Gly Gly Tyr Leu Lys Ile Leu
305                 310                 315                 320

Pro Met Phe Phe Ile Val Met Pro Gly Met Ile Ser Arg Ala Leu Phe
                325                 330                 335

Pro Asp Glu Val Gly Cys Val Asp Pro Asp Val Cys Gln Arg Ile Cys
            340                 345                 350

Gly Ala Arg Val Gly Cys Ser Asn Ile Ala Tyr Pro Lys Leu Val Met
        355                 360                 365

Ala Leu Met Pro Val Gly Leu Arg Gly Leu Met Ile Ala Val Ile Met
        370                 375                 380

Ala Ala Leu Met Ser Ser Leu Thr Ser Ile Phe Asn Ser Ser Ser Thr
385                 390                 395                 400

Leu Phe Thr Ile Asp Val Trp Gln Arg Phe Arg Arg Lys Ser Thr Glu
                405                 410                 415

Gln Glu Leu Met Val Val Gly Arg Val Phe Val Val Phe Leu Val Val
            420                 425                 430

Ile Ser Ile Leu Trp Ile Pro Ile Ile Gln Ser Ser Asn Ser Gly Gln
        435                 440                 445

Leu Phe Asp Tyr Ile Gln Ala Val Thr Ser Tyr Leu Ala Pro Pro Ile
        450                 455                 460

Thr Ala Leu Phe Leu Leu Ala Ile Phe Cys Lys Arg Val Thr Glu Pro
465                 470                 475                 480

Gly Ala Phe Trp Gly Leu Val Phe Gly Leu Gly Val Gly Leu Leu Arg
                485                 490                 495

Met Ile Leu Glu Phe Ser Tyr Pro Ala Pro Ala Cys Gly Glu Val Asp
            500                 505                 510

Arg Arg Pro Ala Val Leu Lys Asp Phe His Tyr Leu Tyr Phe Ala Ile
        515                 520                 525

Leu Leu Cys Gly Leu Thr Ala Ile Val Ile Val Ile Val Ser Leu Cys
        530                 535                 540

Thr Thr Pro Ile Pro Glu Glu Gln Leu Thr Arg Leu Thr Trp Trp Thr
545                 550                 555                 560

Arg Asn Cys Pro Leu Ser Glu Leu Glu Lys Glu Ala His Glu Ser Thr
                565                 570                 575

Pro Glu Ile Ser Glu Arg Pro Ala Gly Glu Cys Pro Ala Gly Gly Gly
            580                 585                 590

Ala Ala Glu Asn Ser Ser Leu Gly Gln Glu Gln Pro Glu Ala Pro Ser
        595                 600                 605

Arg Ser Trp Gly Lys Leu Leu Trp Ser Trp Phe Cys Gly Leu Ser Gly
        610                 615                 620

Thr Pro Glu Gln Ala Leu Ser Pro Ala Glu Lys Ala Ala Leu Glu Gln
625                 630                 635                 640

Lys Leu Thr Ser Ile Glu Glu Pro Leu Trp Arg His Val Cys Asn
                645                 650                 655

Ile Asn Ala Val Leu Leu Leu Ala Ile Asn Ile Phe Leu Trp Gly Tyr
            660                 665                 670
```

Phe Ala
674

<210> SEQ ID NO 2
<211> LENGTH: 2022
<212> TYPE: DNA
<213> ORGANISM: Human

<400> SEQUENCE: 2

| | | | | | | |
|---|---|---|---|---|---|---|
| atgggcctg | gagcttcagg | ggacggggtc | aggactgaga | cagctccaca | catagcactg | 60 |
| gactccagag | ttggtctgca | cgcctacgac | atcagcgtgg | tggtcatcta | ctttgtcttc | 120 |
| gtcattgctg | tggggatctg | gtcgtccatc | cgtgcaagtc | gagggaccat | tggcggctat | 180 |
| ttcctggccg | ggaggtccat | gagctggtgg | ccaattggag | catctctgat | gtccagcaat | 240 |
| gtgggcagtg | gcttgttcat | cggcctggct | gggacagggg | ctgccggagg | ccttgccgta | 300 |
| ggtggcttcg | agtggaacgc | aacctggctg | ctcctggccc | ttggctgggt | cttcgtccct | 360 |
| gtgtacatcg | cagcaggtgt | ggtcacaatg | ccgcagtatc | tgaagaagcg | atttggggc | 420 |
| cagaggatcc | aggtgtacat | gtctgtcctg | tctctcatcc | tctacatctt | caccaagatc | 480 |
| tcgactgaca | tcttctctgg | agccctcttc | atccagatgg | cattgggctg | aacctgtac | 540 |
| ctctccacag | ggatcctgct | ggtggtgact | gccgtctaca | ccattgcagg | tggcctcatg | 600 |
| gccgtgatct | acacagatgc | tctgcagacg | gtgatcatgg | tagggggagc | cctggtcctc | 660 |
| atgtttctgg | gctttcagga | cgtgggctgg | tacccaggcc | tggagcagcg | gtacaggcag | 720 |
| gccatcccta | atgtcacagt | ccccaacacc | acctgtcacc | tcccacggcc | cgatgctttc | 780 |
| cacatgcttc | gggaccctgt | gagcggggac | atcccttggc | caggtctcat | tttcgggctc | 840 |
| acagtgctgg | ccacctggtg | ttggtgcaca | gaccaggtca | ttgtgcagcg | gtctctctcg | 900 |
| gccaagagtc | tgtctcatgc | caagggaggc | tccgtgctgg | ggggctacct | gaagatcctc | 960 |
| cccatgttct | tcatcgtcat | gcctggcatg | atcagccggg | ccctgttccc | agacgaggtg | 1020 |
| ggctgcgtgg | accctgatgt | ctgccaaaga | atctgtgggg | cccgagtggg | atgttccaac | 1080 |
| attgcctacc | ctaagttggt | catggccctc | atgcctgttg | gtctgcgggg | gctgatgatt | 1140 |
| gccgtgatca | tggccgctct | catgagctca | ctcacctcca | tcttcaacag | cagcagcacc | 1200 |
| ctgttcacca | ttgatgtgtg | gcagcgcttc | cgcaggaagt | caacagagca | ggagctgatg | 1260 |
| gtggtgggca | gagtgtttgt | ggtgttcctg | gttgtcatca | gcatcctctg | gatccccatc | 1320 |
| atccaaagct | ccaacagtgg | gcagctcttc | gactacatcc | aggctgtcac | cagttacctg | 1380 |
| gccccaccca | tcaccgctct | cttcctgctg | ccatcttct | gcaagagggt | cacagagccc | 1440 |
| ggagctttct | ggggcctcgt | gtttggcctg | ggagtggggc | ttctgcgtat | gatcctggag | 1500 |
| ttctcatacc | cagcgccagc | ctgtggggag | gtggaccgga | ggccagcagt | gctgaaggac | 1560 |
| ttccactacc | tgtactttgc | aatcctcctc | tgcgggctca | ctgccatcgt | cattgtcatt | 1620 |
| gtcagcctct | gtacaactcc | catccctgag | gaacagctca | cacgcctcac | atggtggact | 1680 |
| cggaactgcc | ccctctctga | gctggagaag | gaggcccacg | agcacacc | ggagatatcc | 1740 |
| gagaggccag | ccggggagtg | ccctgcagga | ggtggagcgg | cagagaactc | gagcctgggc | 1800 |
| caggagcagc | ctgaagcccc | aagcaggtcc | tggggaaagt | tgctctggag | ctggttctgt | 1860 |
| gggctctctg | gaacaccgga | gcaggccctg | agcccagcag | agaaggctgc | gctagaacag | 1920 |
| aagctgacaa | gcattgagga | ggagccactc | tggagacatg | tctgcaacat | caatgctgtc | 1980 |
| cttttgctgg | ccatcaacat | cttcctctgg | ggctattttg | cg | | 2022 |

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
ctaacagaga gcaaggagct ggc                                             23

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
aggtctgtgg aatcacgcaa                                                 20

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
tggaattcat ggggcctgga gctt                                            24

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
tctactagtt cacgcaaaat agccccaga                                       29

<210> SEQ ID NO 7
<211> LENGTH: 3140
<212> TYPE: DNA
<213> ORGANISM: Human

<400> SEQUENCE: 7
atggggcctg gagcttcagg ggacggggtc aggactgaga cagctccaca catagcactg      60
gactccagag ttggtctgca cgcctacgac atcagcgtgg tggtcatcta ctttgtcttc     120
gtcattgctg tggggatctg gtcgtccatc cgtgcaagtc gagggaccat tggcggctat     180
ttcctggccg ggaggtccat gagctggtgg ccaattggag catctctgat gtccagcaat     240
gtgggcagtg gcttgttcat cggcctggct gggacagggg ctgccggagg ccttgccgta     300
ggtggcttcg agtggaacgc aacctggctg ctcctggccc ttggctgggt cttcgtccct     360
gtgtacatcg cagcaggtgt ggtcacaatg ccgcagtatc tgaagaagcg atttgggggc     420
cagaggatcc aggtgtacat gtctgtcctg tctctcatcc tctacatctt caccaagatc     480
tcgactgaca tcttctctgg agccctcttc atccagatgc cattgggctg gaacctgtac     540
ctctccacag ggatcctgct ggtggtgact gccgtctaca ccattgcagg tggcctcatg     600
gccgtgatct acacagatgc tctgcagacg gtgatcatgg taggggagc cctggtcctc     660

```
atgtttctgg gctttcagga cgtgggctgg tacccaggcc tggagcagcg gtacaggcag    720
gccatcccta atgtcacagt ccccaacacc acctgtcacc tcccacggcc cgatgctttc    780
cacatgcttc gggaccctgt gagcggggac atcccttggc caggtctcat tttcgggctc    840
acagtgctgg ccacctggtg ttggtgcaca gaccaggtca ttgtgcagcg gtctctctcg    900
gccaagagtc tgtctcatgc caagggaggc tccgtgctgg ggggctacct gaagatcctc    960
cccatgttct tcatcgtcat gcctggcatg atcagccggg ccctgttccc agacgaggtg   1020
ggctgcgtgg accctgatgt ctgccaaaga atctgtgggg cccgagtggg atgttccaac   1080
attgcctacc ctaagttggt catggccctc atgcctgttg gtctgcgggg ctgatgatt    1140 gccgtgatca tggccgctct catgagctca ctcacctcca tcttcaacag cagcagcacc   1200
ctgttcacca ttgatgtgtg gcagcgcttc cgcaggaagt caacagagca ggagctgatg   1260
gtggtgggca gagtgtttgt ggtgttcctg gttgtcatca gcatcctctg gatccccatc   1320
atccaaagct ccaacagtgg gcagctcttc gactacatcc aggctgtcac cagttacctg   1380
gccccaccca tcaccgctct cttcctgctg ccatcttct gcaagagggt cacagagccc    1440
ggagctttct ggggcctcgt gtttggcctg ggagtggggc ttctgcgtat gatcctggag   1500
ttctcatacc cagcgccagc ctgtggggag gtggaccgga ggccagcagt gctgaaggac   1560
ttccactacc tgtactttgc aatcctcctc tgcgggctca ctgccatcgt cattgtcatt   1620
gtcagcctct gtacaactcc catccctgag gaacagctca cacgcctcac atggtggact   1680
cggaactgcc ccctctctga gctggagaag gaggcccacg agagcacacc ggagatatcc   1740
gagaggccag ccggggagtg ccctgcagga ggtggagcgg cagagaactc gagcctgggc   1800
caggagcagc ctgaagcccc aagcaggtcc tggggaaagt tgctctggag ctggttctgt   1860
gggctctctg gaacaccgga gcaggccctg agcccagcag agaaggctgc gctagaacag   1920
aagctgacaa gcattgagga ggagccactc tggagacatg tctgcaacat caatgctgtc   1980
cttttgctgg ccatcaacat cttcctctgg ggctattttg cgtgattcca cagacctggc   2040
ttcagtgtag acagattaaa caaagcccaa gcctgtcagc cacagaaaca ggctctcctc   2100
ttactttgct gtctaaactg gagatcacag aagtcaagac tgcaagctcc cctgaagaga   2160
atccaactca acctgcacac ttgacaagtg gagaaacaga agctcagaga gagcactggg   2220
tttgttcagg accacccaga aggtgtcaca cggggtttcc ccactctttc tgatatattg   2280
ccttacagac ctacctcaaa cacactgttt ccaccctctt cttgaatgta ttcagtagcc   2340
tttactgaat gtgtgtcttg agagtagaaa atggaggat acaagaaaag gagcaggaag    2400
aaatttgcaa aaatccaaga gcacctttgc tcccccttat cctccttcct cttcccttt     2460 ctagttcccc tacctctcta tctttctatt ctcaccaata atctctttgt tgcatgaatt    2520
tacccaggag agtcctatat ttccattggt ggctccacag tggtggctgt cagacccgaa   2580 gggtgggga gccaagggtg gactttaagc atggtgacag atggtatttt gggcagaaag    2640
ctcttagaca atggactatc caaagcacta tttaaattct gcctcttcct actctctaac   2700
ccaaatatgc acaaactctc tatggccttg agaagcagtt ggagagacat gacttgttaa   2760
aacctcaagg aatcaagaca tgttactctg tatttaaggg taagccccac agcgggcagc   2820
acaaacagcc tggagccac tgtgcctgtg cttctctgtc cttctccctt tgcttgccat    2880
gaatccgcat accttggaat acactgtgac cccagttaag tgtcccttcg ccaggaagct   2940
gccgcaacgt ccagacctgg gtcaagttcc cactcctgct cccatagcct tgacctgctt   3000
ctgtcacagc actgatcaca ctgagatgga agactccagg gggcaaggac caagggccat   3060
```

```
atcccaagtg actttgtacc cagaaaataa cagctgttca ataaatgtgt attgagttaa    3120
aaaaaaaaaa aaaaaaaaaa                                                3140
```

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8

```
ggtctgcggg ggctgatgat tg                                             22
```

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9

```
aggctggcgc tgggtatgag aac                                            23
```

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10

```
cccgatgctt tccacattct tc                                             22
```

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11

```
acaatgacct ggtctgtgca cc                                             22
```

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12

```
acatcccttg gccaggtctc attttcgg                                       28
```

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13

```
gggggccaga ggatccaggt gta                                            23
```

<210> SEQ ID NO 14

```
<211> LENGTH: 22
<212> TYPE: DNA
<213> ORGANISM: Artificial Sequence
<220> FEATURE:
<223> OTHER INFORMATION: Primer

<400> SEQUENCE: 14
gcaatcatca gcccccgcag ac                                              22

<210> SEQ ID NO 15
<211> LENGTH: 678
<212> TYPE: PRT
<213> ORGANISM: Mouse

<400> SEQUENCE: 15
```

| Met | Glu | Pro | Gly | Val | Ser | Arg | Asn | Gly | Val | Arg | Thr | Glu | Thr | Thr | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Asn Pro Ser Leu Gly Leu His Thr Tyr Asp Ile Val Val Val Ile
              20                  25                  30

Tyr Phe Val Phe Val Leu Ala Val Gly Ile Trp Ser Ile Arg Ala
          35                  40                  45

Ser Arg Gly Thr Val Gly Gly Tyr Phe Leu Ala Gly Arg Ser Met Thr
 50                  55                  60

Trp Trp Pro Ile Gly Ala Ser Leu Met Ser Ser Asn Val Gly Ser Gly
 65                  70                  75                  80

Leu Phe Ile Gly Leu Ala Gly Thr Gly Ala Ala Gly Gly Leu Ala Val
                 85                  90                  95

Gly Gly Phe Glu Trp Asn Ala Thr Phe Leu Leu Leu Ala Leu Gly Trp
            100                 105                 110

Ile Phe Val Pro Val Tyr Ile Ala Ala Gly Val Val Thr Met Pro Gln
        115                 120                 125

Tyr Leu Lys Lys Arg Phe Gly Gly Gln Arg Ile Gln Val Tyr Met Ser
130                 135                 140

Val Leu Ser Leu Ile Leu Tyr Ile Phe Thr Lys Ile Ser Thr Asp Ile
145                 150                 155                 160

Phe Ser Gly Ala Leu Phe Ile Gln Met Ala Leu Gly Trp Asn Leu Tyr
                165                 170                 175

Leu Ser Thr Val Ile Leu Leu Val Val Thr Ala Val Tyr Thr Ile Ala
            180                 185                 190

Gly Gly Leu Thr Ala Val Ile Tyr Thr Asp Ala Leu Gln Thr Val Ile
        195                 200                 205

Met Val Gly Gly Ala Leu Val Leu Met Phe Leu Gly Phe Gln Glu Val
    210                 215                 220

Gly Trp Tyr Pro Gly Leu Gln Gln Leu Tyr Arg Gln Ala Ile Pro Asn
225                 230                 235                 240

Thr Thr Val Pro Asn Thr Thr Cys His Leu Pro Arg Pro Asp Ala Phe
                245                 250                 255

His Met Leu Arg Asp Pro Val Asn Gly Asp Ile Pro Trp Pro Gly Leu
            260                 265                 270

Ile Phe Gly Leu Thr Val Leu Ala Thr Trp Cys Trp Cys Thr Asp Gln
        275                 280                 285

Val Ile Val Gln Arg Ser Leu Ala Ala Lys Asn Leu Ser His Ala Lys
    290                 295                 300

Gly Gly Ser Val Leu Gly Gly Tyr Leu Lys Ile Leu Pro Met Phe Phe
305                 310                 315                 320

Ile Val Met Pro Gly Met Ile Ser Arg Ala Leu Tyr Pro Asp Glu Val

| | | 325 | | | 330 | | | 335 | | |
|---|---|---|---|---|---|---|---|---|---|---|
Ala Cys Val Asp Pro Asp Ile Cys Gln Arg Val Cys Gly Ala Arg Val
                    340                 345                 350
Gly Cys Ser Asn Ile Ala Tyr Pro Lys Leu Val Met Ala Leu Met Pro
                355                 360                 365
Val Gly Leu Arg Gly Leu Met Ile Ala Val Ile Met Ala Ala Leu Met
            370                 375                 380
Ser Ser Leu Thr Ser Ile Phe Asn Ser Ser Ser Thr Leu Phe Ala Ile
385                 390                 395                 400
Asp Val Trp Gln Arg Phe Arg Arg Gln Ala Ser Glu Gln Glu Leu Met
                    405                 410                 415
Val Val Gly Arg Leu Phe Val Val Phe Leu Val Val Ile Ser Ile Leu
                420                 425                 430
Trp Ile Pro Ile Ile Gln Ser Ser Asn Ser Gly Gln Leu Phe Asp Tyr
            435                 440                 445
Ile Gln Ser Ile Thr Ser Tyr Leu Ala Pro Pro Ile Thr Ala Leu Phe
450                 455                 460
Leu Leu Ala Ile Phe Cys Lys Arg Val Asn Glu Pro Gly Ala Phe Trp
465                 470                 475                 480
Gly Leu Met Phe Gly Leu Val Val Gly Ile Leu Arg Met Ile Leu Glu
                485                 490                 495
Phe Ser Tyr Ser Ala Pro Ala Cys Gly Glu Met Asp Arg Arg Pro Ala
                500                 505                 510
Val Leu Lys Asp Phe His Tyr Leu Tyr Phe Ala Leu Leu Leu Cys Gly
                515                 520                 525
Leu Thr Ala Ile Ile Ile Val Val Ile Ser Phe Phe Thr Glu Pro Ile
530                 535                 540
Pro Asp Asp Lys Leu Ala Arg Leu Thr Trp Trp Thr Arg Asn Cys Ala
545                 550                 555                 560
Val Ser Asp Leu Gln Lys Lys Thr Ser Val Ser Val Asn Asn Thr Glu
                565                 570                 575
Asp Asp Asn Ser Pro Gly Leu Ala Gly Arg Pro Val Val Glu Gly Pro
            580                 585                 590
Ala Gly Asp Glu Glu Glu Ala Asn Thr Thr Gln Gly Pro Glu Gln Pro
                595                 600                 605
Gly Ala Leu His Arg Ser Trp Gly Lys Trp Leu Trp Asn Trp Phe Cys
            610                 615                 620
Gly Leu Ser Gly Ala Pro Gln Gln Ala Leu Ser Pro Ala Glu Lys Ala
625                 630                 635                 640
Val Leu Glu Gln Lys Leu Thr Ser Ile Glu Glu Pro Leu Trp Arg
                    645                 650                 655
Arg Val Cys Asn Ile Asn Ala Ile Ile Leu Leu Ala Ile Asn Ile Phe
                660                 665                 670
Leu Trp Gly Tyr Phe Ala
            675         678

<210> SEQ ID NO 16
<211> LENGTH: 2034
<212> TYPE: DNA
<213> ORGANISM: Mouse

<400> SEQUENCE: 16
atggaaccag gagtgtcaag gaatggagtc agaactgaga caacaacgaa cccaagcctg      60
gggctacata cctatgacat cgtggtggtg gtcatctatt ttgtctttgt tcttgctgtg     120

-continued

```
ggaatttggt catccatccg tgcaagtcga gggaccgttg gtggctattt cctggctggg      180
agatccatga cctggtggcc aattggagca tctctaatgt ccagcaatgt gggcagtggc      240
ttatttatcg gcctggctgg aacagggqct gctggaggac ttgctgttgg tggctttgag      300
tggaacgcaa ccttcctgct tctagccctg gctggatct ttgtccctgt gtacatagca       360
gctggtgtgg tcaccatgcc acagtacctg aagaaacgat tgggggaca gaggatccag       420 gtgtacatgt cagttctttc tctcatcctc tacatcttca ccaagatatc gactgatatc      480
ttctctggag ccctcttcat ccagatggcc ttgggctgga atctctatct ctccacagtc      540
atcttgctgg tggtgacagc tgtctacacc attgcagggg gcctcacagc tgtgatctac     600
acagatgctc tacagactgt gatcatggtt gggggagctc tggtcctcat gtttctgggc     660
tttcaggagg ttggctggta cccaggcctg cagcagctct atagacaggc catccccaat     720
accacagttc caataccac ctgtcacctc ccacggcctg atgccttcca catgcttcga      780
gatcctgtga atggagacat ccctggcca gtctcattt ttggcctcac agtcttggcc       840
acctggtgtt ggtgcacaga ccaggtgatt gtgcagaggt ctctcgcagc caagaatctt    900
tcacatgcca agggaggctc cgtgctaggg gctacctaa agatcctccc aatgttcttc      960
attgtcatgc ctggcatgat cagcagggcc ctgtacccag atgaagttgc ctgtgtggac     1020
cctgacatct gtcaaagagt gtgtgggcc agagttggat gctccaatat tgcctacccc     1080
aagctggtta tggctctcat gcctgtgggg ctgcgaggcc tgatgattgc tgtgatcatg    1140
gctgccctca tgagctcact cacctctatc ttcaacagca gtagcaccct gtttgccata    1200
gatgtgtggc agcgcttccg caggcaggca tcggagcaag agctgatggt ggtaggcagg    1260
ttgttcgtag tcttcctggt agtcatcagc atcctctgga tccccatcat ccagagctcc    1320
aatagtgggc agctctttga ctacatccaa tctatcacca gctacttagc cccacccatc    1380
acagccctct tcctgctggc tatcttctgc aagagggtca cgagcctggt gccttctgg     1440 ggcctcatgt ttggcctggt cgtcggaata ctgcgtatga ttctggagtt ctcatactcg    1500
gccccagcct gtgggagat ggacaggcgg ccagctgttc tgaaggactt ccactacctg     1560
tactttgccc ttctcctctg tggactgacc gcgatcatca ttgtcgtaat cagcttcttc    1620
acggagccca tccccgatga caagcttgct cgcctgacct ggtggacaag gaactgtgcc    1680
gtatctgacc tgcagaagaa aacctctgtg agtgtgaaca acacagagga tgacaactct    1740
ccaggactgg cagggaggcc agtggtagag ggccctgcag agatgaggga agaagcaaac    1800
accactcagg ggcctgaaca accaggagcc ctacacaggt cctggggaaa atggctgtgg    1860
aactggttct gcggactctc aggagcccca cagcaagccc tgagcccagc tgagaaggct    1920
gtgttggagc agaagctgac cagcatcgag gaggagccgc tctggagacg tgtctgcaac    1980
atcaacgcca tcatcctgct agccatcaac atctttctct ggggctattt tgcg          2034
```

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
atggaaccag gagtgtcaag gaa                                              23

<210> SEQ ID NO 18

```
<211> LENGTH: 23
<212> TYPE: DNA
<213> ORGANISM: Artificial Sequence
<220> FEATURE:
<223> OTHER INFORMATION: Primer

<400> SEQUENCE: 18
ggagtcgcaa aatagcccca gag                                              23

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
cggaattcat ggaaccagga gtgtcaag                                         28

<210> SEQ ID NO 20
<211> LENGTH: 29
<212> TYPE: DNA
<213> ORGANISM: Artificial Sequence
<220> FEATURE:
<223> OTHER INFORMATION: Primer

<400> SEQUENCE: 20
tctactagtt cacgcaaaat agccccaga                                        29

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
tgcacagacc aggtgattgt g                                                21

<210> SEQ ID NO 22
<211> LENGTH: 17
<212> TYPE: DNA
<213> ORGANISM: Artificial Sequence
<220> FEATURE:
<223> OTHER INFORMATION: Primer

<400> SEQUENCE: 22
gcacggagcc tcccttg                                                     17

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
ctcgcagcca acaatctttc acatg                                            25

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
```
atctctaatg tccagcaatg tg 22

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
accagcttgg ggtaggcaat 20

<210> SEQ ID NO 26
<211> LENGTH: 681
<212> TYPE: PRT
<213> ORGANISM: Rat

<400> SEQUENCE: 26

Met Glu Pro Gly Ala Ser Arg Asp Gly Leu Arg Ala Glu Thr Thr His
1               5                   10                  15

Gln Ala Leu Gly Ser Gly Val Ser Leu His Thr Tyr Asp Ile Val Val
            20                  25                  30

Val Val Ile Tyr Phe Val Phe Val Leu Ala Val Gly Ile Trp Ser Ser
        35                  40                  45

Ile Arg Ala Ser Arg Gly Thr Ile Gly Gly Tyr Phe Leu Ala Gly Arg
    50                  55                  60

Ser Met Thr Trp Trp Pro Ile Gly Ala Ser Leu Met Ser Ser Asn Val
65                  70                  75                  80

Gly Ser Gly Leu Phe Ile Gly Leu Ala Gly Thr Gly Ala Ala Gly Gly
                85                  90                  95

Leu Ala Val Gly Gly Phe Glu Trp Asn Ala Thr Phe Leu Leu Leu Ala
            100                 105                 110

Leu Gly Trp Ile Phe Val Pro Val Tyr Ile Ala Ala Gly Val Val Thr
        115                 120                 125

Met Pro Gln Tyr Leu Lys Lys Arg Phe Gly Gly Gln Arg Ile Gln Val
    130                 135                 140

Tyr Met Ser Val Leu Ser Leu Ile Leu Tyr Ile Phe Thr Lys Ile Ser
145                 150                 155                 160

Thr Asp Ile Phe Ser Gly Ala Leu Phe Ile Gln Met Ala Leu Gly Trp
                165                 170                 175

Asn Leu Tyr Leu Ser Thr Val Ile Leu Leu Val Val Thr Ala Val Tyr
            180                 185                 190

Thr Ile Ala Gly Gly Leu Thr Ala Val Ile Tyr Thr Asp Ala Leu Gln
        195                 200                 205

Thr Val Ile Met Val Gly Gly Ala Leu Val Leu Met Phe Leu Gly Phe
    210                 215                 220

Arg Glu Val Gly Trp Tyr Pro Gly Leu Gln Gln Leu Tyr Arg Gln Ser
225                 230                 235                 240

Ile Pro Asn Val Thr Val Pro Asn Thr Thr Cys His Leu Pro Arg Ser
                245                 250                 255

Asp Ala Phe His Met Leu Arg Asp Pro Val Asn Gly Asp Ile Pro Trp
            260                 265                 270

Pro Gly Leu Ile Phe Gly Leu Thr Val Leu Ala Thr Trp Cys Trp Cys
        275                 280                 285

Thr Asp Gln Val Ile Val Gln Arg Ser Leu Ser Ala Lys Ser Leu Ser
    290                 295                 300

-continued

```
His Ala Lys Gly Gly Ser Val Leu Gly Gly Tyr Leu Lys Ile Leu Pro
305                 310                 315                 320

Met Phe Phe Ile Val Met Pro Gly Met Ile Ser Arg Ala Leu Tyr Pro
                325                 330                 335

Asp Glu Val Ala Cys Val Asp Pro Asp Ile Cys Gln Arg Val Cys Gly
            340                 345                 350

Ala Arg Val Gly Cys Ser Asn Ile Ala Tyr Pro Lys Leu Val Met Ala
        355                 360                 365

Leu Met Pro Val Gly Leu Arg Gly Leu Met Ile Ala Val Ile Met Ala
370                 375                 380

Ala Leu Met Ser Ser Leu Thr Ser Ile Phe Asn Ser Ser Ser Thr Leu
385                 390                 395                 400

Phe Ala Ile Asp Val Trp Gln Arg Val Arg Arg Gln Ala Ser Glu Gln
                405                 410                 415

Glu Leu Met Val Val Gly Arg Leu Phe Val Phe Leu Val Leu Ile
            420                 425                 430

Ser Ile Leu Trp Ile Pro Ile Ile Gln Ser Ser Asn Ser Gly Gln Leu
        435                 440                 445

Phe Asp Tyr Ile Gln Ser Ile Thr Ser Tyr Leu Ala Pro Pro Ile Thr
450                 455                 460

Ala Leu Phe Leu Leu Ala Ile Phe Cys Lys Arg Val Thr Glu Pro Gly
465                 470                 475                 480

Ala Phe Trp Gly Leu Met Phe Gly Leu Val Val Gly Ile Leu Arg Met
                485                 490                 495

Ile Leu Glu Phe Ser Tyr Ser Ala Pro Ala Cys Gly Glu Lys Asp Arg
            500                 505                 510

Arg Pro Ala Val Leu Lys Asp Phe His Tyr Leu Tyr Phe Ala Leu Leu
        515                 520                 525

Leu Cys Gly Leu Thr Ala Ile Ile Val Ile Ile Ser Phe Phe Thr
530                 535                 540

Glu Pro Ile Pro Asp Glu Lys Leu Ala Arg Leu Thr Trp Trp Thr Arg
545                 550                 555                 560

Ser Cys Pro Ile Ser Glu Leu Gln Lys Lys Val Ser Val Ser Val Asn
                565                 570                 575

Asn Thr Glu Ser Asp Asn Ser Pro Ala Leu Ala Gly Arg Pro Val Met
            580                 585                 590

Glu Gly Thr Ala Gly Asp Glu Glu Ala Asn Thr Thr Ser Glu Pro
        595                 600                 605

Glu Gln Pro Glu Val Leu His Arg Ser Trp Gly Lys Trp Leu Trp Asn
610                 615                 620

Trp Phe Cys Gly Leu Ser Gly Thr Pro Gln Gln Ala Leu Ser Pro Ala
625                 630                 635                 640

Glu Lys Ala Glu Leu Glu Gln Lys Leu Thr Ser Ile Glu Glu Pro
                645                 650                 655

Leu Trp Arg Cys Val Cys Asn Ile Asn Ala Ile Ile Leu Leu Ala Ile
            660                 665                 670

Asn Ile Phe Leu Trp Gly Tyr Phe Ala
        675                 680 681

<210> SEQ ID NO 27
<211> LENGTH: 2043
<212> TYPE: DNA
<213> ORGANISM: Mouse
```

<400> SEQUENCE: 27

```
atggaacctg gagcttcaag ggatggactc agagctgaga caacacacca agccctgggc    60
tctggagtca gcctgcacac ctatgacatc gtggtggtgg tcatctactt tgtctttgtc   120
cttgctgtgg gaatttggtc gtccatccgc gcaagccgag ggaccattgg tggctatttc   180
ctggctggaa gatccatgac ctggtggcca attggagcat ctctaatgtc cagcaatgtg   240
ggcagtggct tattcatcgg cctggctgga acaggggctg ctggaggcct tgctgtgggt   300
ggcttcgagt ggaatgcaac ttttctgctt ctggccctgg gctggatctt tgtccctgtg   360
tacatcgcag ctggtgtggt caccatgcca cagtacctga gaaacgatt tggggggcag   420
aggatccagg tgtacatgtc agtcctgtct ctcatactct acatcttcac caagatatcg   480
actgatatct ctctggagc cctcttcatc cagatgcct tgggctggaa tctctatctc     540
tccacagtca tcctgctggt ggtgacagct gtctacacca ttgcaggggg cctcacagct   600
gtgatctaca cagatgctct acagaccgtg atcatggttg ggggagccct ggtcctcatg   660
tttctgggct tcggggaggt cggctggtac ccaggcttgc agcagctcta tagacagtcc   720
atccccaatg tcacagttcc caacactacc tgtcacctcc cacggtctga tgccttccac   780
atgcttcgag atcctgtgaa cggggacatc ccctggccag gtcttatttt tggcctcaca   840
gtcttggcca cctggtgttg gtgcacggac caggtgattg tgcagaggtc tctctcggcc   900
aagagtcttt cacatgccaa gggaggatca gtgttagggg ctacctaaa gatcctccca   960
atgttcttca ttgtcatgcc cggcatgatc agcaggccc tgtacccaga tgaagtcgcc  1020
tgtgtggacc ctgacatctg tcagagagtg tgtggggcca gagttggatg ctccaatatt  1080
gcctacccca aacttgttat ggctctcatg cctgtgggtc tgcgaggcct gatgattgcc  1140
gtgatcatgg ctgccctcat gagctcactc acctccatct tcaacagcag tagcaccctg  1200
tttgccatag atgtgtggca gcgagtccgc aggcaggcat cggagcaaga gctgatggtg  1260
gtaggcaggt tgtttgtagt cttcctggta ctcatcagca tcctctggat ccccatcatc  1320
cagagctcca atagtgggca gctctttgac tacatccaat ccatcaccag ctacctagcc  1380
ccgcccatca cagccctctt cctgctggcc atcttctgca gagggtcac tgagcctggt  1440
gccttctggg gcctcatgtt tggcctggta gtgggaatac tgcgtatgat tctggagttc  1500
tcatactcag ccccagcctg tggggagaag gacaggcggc cagctgttct taaggacttc  1560
cactacctgt actttgccct cctcctctgt ggacttaccg ccatcatcat tgtcataatc  1620
agcttcttca cggagcccat ccccgacgaa aagcttgctc gcctgacctg gtggacaagg  1680
agctgtccca tatctgaact acagaagaaa gtctctgtga gtgtaacaa cacagagagt  1740
gacaactctc cagcactggc agggaggcca gtgatggagg gcactgcagg agatgaggaa  1800
gaagcaaaca ccacctcaga gcctgaacaa ccagaagtcc tacacaggtc ctgggggaaa  1860
tggctgtgga actggttctg cggactctct ggaacaccac agcaagcact gagcccagct  1920
gagaaggctg agctggagca gaagctgacc agcatcgagg aagagccact ctggagatgt  1980
gtctgcaaca tcaatgccat catcctgctg gccatcaaca tctttctctg gggctatttt  2040
gcg                                                               2043
```

<210> SEQ ID NO 28
<211> LENGTH: 22
<212> TYPE: DNA
<213> ORGANISM: Artificial Sequence
<220> FEATURE:
<223> OTHER INFORMATION: Primer

```
<400> SEQUENCE: 28
caatggaacc tggagcttca ag                                              22

<210> SEQ ID NO 29
<211> LENGTH: 24
<212> TYPE: DNA
<213> ORGANISM: Artificial Sequence
<220> FEATURE:
<223> OTHER INFORMATION: Primer

<400> SEQUENCE: 29
tgacgcaaaa tagccccaga gaag                                            24

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
cggaattcat ggaacctgga gcttc                                           25

<210> SEQ ID NO 31
<211> LENGTH: 29
<212> TYPE: DNA
<213> ORGANISM: Artificial Sequence
<220> FEATURE:
<223> OTHER INFORMATION: Primer

<400> SEQUENCE: 31
tctactagtt cacgcaaaat agccccaga                                       29

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ctcacagtct tggccacctg                                                 20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
agaaccggct ctctctggag                                                 20

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
tgcacggacc aggtgattgt gc                                              22

<210> SEQ ID NO 35
```

```
<211> LENGTH: 22
<212> TYPE: DNA
<213> ORGANISM: Artificial Sequence
<220> FEATURE:
<223> OTHER INFORMATION: Primer

<400> SEQUENCE: 35
tctggagtca gcctgcacac ct                                             22

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
cagccttctc agctgggctc ag                                             22

<210> SEQ ID NO 37
<211> LENGTH: 16
<212> TYPE: PRT
<213> ORGANISM: Human

<400> SEQUENCE: 37

His Met Leu Arg Asp Pro Val Ser Gly Asp Ile Pro Trp Pro Gly Cys
1               5                   10                  15

<210> SEQ ID NO 38
<211> LENGTH: 25
<212> TYPE: DNA
<213> ORGANISM: Artificial Sequence
<220> FEATURE:
<223> OTHER INFORMATION: Primer

<400> SEQUENCE: 38
cagaggatcc agatgtacat gtctg                                          25

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
tgctttccac attcttcggg accct                                          25

<210> SEQ ID NO 40
<211> LENGTH: 2022
<212> TYPE: DNA
<213> ORGANISM: Human

<400> SEQUENCE: 40
atggggcctg gagcttcagg ggacggggtc aggactgaga cagctccaca catagcactg    60
gactccagag ttggtctgca cgcctacgac atcagcgtgg tggtcatcta ctttgtcttc   120
gtcattgctg tggggatctg gtcgtccatc cgtgcaagtc gagggaccat tggcggctat   180
ttcctggccg ggaggtccat gagctggtgg ccaattggag catctctgat gtccagcaat   240
gtgggcagtg gcttgttcat cggcctggct gggacagggg ctgccggagg ccttgccgta   300
ggtggcttcg agtggaacgc aacctggctg ctcctggccc ttggctgggt cttcgtccct   360
gtgtacatcg cagcaggtgt ggtcacaatg ccgcagtatc tgaagaagcg atttgggggc   420
```

-continued

```
cagaggatcc agatgtacat gtctgtcctg tctctcatcc tctacatctt caccaagatc    480
tcgactgaca tcttctctgg agccctcttc atccagatgg cattgggctg gaacctgtac    540
ctctccacag ggatcctgct ggtggtgact gccgtctaca ccattgcagg tggcctcatg    600
gccgtgatct acacagatgc tctgcagacg gtgatcatgt aggggggagc cctggtcctc    660
atgtttctgg gctttcagga cgtgggctgg tacccaggcc tggagcagcg gtacaggcag    720
gccatcccta atgtcacagt ccccaacacc acctgtcacc tcccacggcc cgatgctttc    780
cacatgcttc gggaccctgt gagcggggac atcccttggc caggtctcat tttcgggctc    840
acagtgctgg ccacctggtg ttggtgcaca gaccaggtca ttgtgcagcg gtctctctcg    900
gccaagagtc tgtctcatgc caagggaggc tccgtgctgg ggggctacct gaagatcctc    960
cccatgttct tcatcgtcat gcctggcatg atcagccggg ccctgttccc agacgaggtg   1020
ggctgcgtgg accctgatgt ctgccaaaga atctgtgggg cccgagtggg atgttccaac   1080
attgcctacc ctaagttggt catggccctc atgcctgttg gtctgcgggg gctgatgatt   1140
gccgtgatca tggccgctct catgagctca ctcacctcca tcttcaacag cagcagcacc   1200
ctgttcacca ttgatgtgtg gcagcgcttc cgcaggaagt caacagagca ggagctgatg   1260
gtggtgggca gagtgtttgt ggtgttcctg gttgtcatca gcatcctctg gatccccatc   1320
atccaaagct ccaacagtgg gcagctcttc gactacatcc aggctgtcac cagttacctg   1380
gccccaccca tcaccgctct cttcctgctg gccatcttct gcaagagggt cacagagccc   1440
ggagctttct ggggcctcgt gtttggcctg ggagtggggc ttctgcgtat gatcctggag   1500
ttctcatacc cagcgccagc ctgtggggag gtggaccgga ggccagcagt gctgaaggac   1560
ttccactacc tgtactttgc aatcctcctc tgcgggctca ctgccatcgt cattgtcatt   1620
gtcagcctct gtacaactcc catccctgag gaacagctca cacgcctcac atggtggact   1680
cggaactgcc ccctctctga gctggagaag gaggcccacg agagcacacc ggagatatcc   1740
gagaggccag ccggggagtg ccctgcagga ggtggagcgg cagagaactc gagcctgggc   1800
caggagcagc ctgaagcccc aagcaggtcc tggggaaagt tgctctggag ctggttctgt   1860
gggctctctg gaacaccgga gcaggccctg agcccagcag agaaggctgc gctagaacag   1920
aagctgacaa gcattgagga ggagccactc tggagacatg tctgcaacat caatgctgtc   1980
cttttgctgg ccatcaacat cttcctctgg ggctattttg cg                      2022
```

<210> SEQ ID NO 41
<211> LENGTH: 674
<212> TYPE: PRT
<213> ORGANISM: Human

<400> SEQUENCE: 41

```
Met Gly Pro Gly Ala Ser Gly Asp Gly Val Arg Thr Glu Thr Ala Pro
1               5                   10                  15

His Ile Ala Leu Asp Ser Arg Val Gly Leu His Ala Tyr Asp Ile Ser
            20                  25                  30

Val Val Val Ile Tyr Phe Val Phe Val Ile Ala Val Gly Ile Trp Ser
        35                  40                  45

Ser Ile Arg Ala Ser Arg Gly Thr Ile Gly Gly Tyr Phe Leu Ala Gly
    50                  55                  60

Arg Ser Met Ser Trp Trp Pro Ile Gly Ala Ser Leu Met Ser Ser Asn
65                  70                  75                  80

Val Gly Ser Gly Leu Phe Ile Gly Leu Ala Gly Thr Gly Ala Ala Gly
                85                  90                  95
```

```
Gly Leu Ala Val Gly Gly Phe Glu Trp Asn Ala Thr Trp Leu Leu Leu
                100                 105                 110

Ala Leu Gly Trp Val Phe Val Pro Val Tyr Ile Ala Ala Gly Val Val
            115                 120                 125

Thr Met Pro Gln Tyr Leu Lys Lys Arg Phe Gly Gly Gln Arg Ile Gln
        130                 135                 140

Met Tyr Met Ser Val Leu Ser Leu Ile Leu Tyr Ile Phe Thr Lys Ile
145                 150                 155                 160

Ser Thr Asp Ile Phe Ser Gly Ala Leu Phe Ile Gln Met Ala Leu Gly
                165                 170                 175

Trp Asn Leu Tyr Leu Ser Thr Gly Ile Leu Leu Val Val Thr Ala Val
            180                 185                 190

Tyr Thr Ile Ala Gly Gly Leu Met Ala Val Ile Tyr Thr Asp Ala Leu
        195                 200                 205

Gln Thr Val Ile Met Val Gly Gly Ala Leu Val Leu Met Phe Leu Gly
    210                 215                 220

Phe Gln Asp Val Gly Trp Tyr Pro Gly Leu Glu Gln Arg Tyr Arg Gln
225                 230                 235                 240

Ala Ile Pro Asn Val Thr Val Pro Asn Thr Thr Cys His Leu Pro Arg
                245                 250                 255

Pro Asp Ala Phe His Met Leu Arg Asp Pro Val Ser Gly Asp Ile Pro
            260                 265                 270

Trp Pro Gly Leu Ile Phe Gly Leu Thr Val Leu Ala Thr Trp Cys Trp
        275                 280                 285

Cys Thr Asp Gln Val Ile Val Gln Arg Ser Leu Ser Ala Lys Ser Leu
    290                 295                 300

Ser His Ala Lys Gly Gly Ser Val Leu Gly Gly Tyr Leu Lys Ile Leu
305                 310                 315                 320

Pro Met Phe Phe Ile Val Met Pro Gly Met Ile Ser Arg Ala Leu Phe
                325                 330                 335

Pro Asp Glu Val Gly Cys Val Asp Pro Asp Val Cys Gln Arg Ile Cys
            340                 345                 350

Gly Ala Arg Val Gly Cys Ser Asn Ile Ala Tyr Pro Lys Leu Val Met
        355                 360                 365

Ala Leu Met Pro Val Gly Leu Arg Gly Leu Met Ile Ala Val Ile Met
    370                 375                 380

Ala Ala Leu Met Ser Ser Leu Thr Ser Ile Phe Asn Ser Ser Ser Thr
385                 390                 395                 400

Leu Phe Thr Ile Asp Val Trp Gln Arg Phe Arg Arg Lys Ser Thr Glu
                405                 410                 415

Gln Glu Leu Met Val Val Gly Arg Val Phe Val Val Phe Leu Val Val
            420                 425                 430

Ile Ser Ile Leu Trp Ile Pro Ile Ile Gln Ser Ser Asn Ser Gly Gln
        435                 440                 445

Leu Phe Asp Tyr Ile Gln Ala Val Thr Ser Tyr Leu Ala Pro Pro Ile
    450                 455                 460

Thr Ala Leu Phe Leu Leu Ala Ile Phe Cys Lys Arg Val Thr Glu Pro
465                 470                 475                 480

Gly Ala Phe Trp Gly Leu Val Phe Gly Leu Val Gly Leu Leu Arg
                485                 490                 495

Met Ile Leu Glu Phe Ser Tyr Pro Ala Pro Ala Cys Gly Glu Val Asp
            500                 505                 510
```

```
Arg Arg Pro Ala Val Leu Lys Asp Phe His Tyr Leu Tyr Phe Ala Ile
        515                 520                 525

Leu Leu Cys Gly Leu Thr Ala Ile Val Ile Val Ile Val Ser Leu Cys
        530                 535                 540

Thr Thr Pro Ile Pro Glu Glu Gln Leu Thr Arg Leu Thr Trp Trp Thr
545                 550                 555                 560

Arg Asn Cys Pro Leu Ser Glu Leu Glu Lys Glu Ala His Glu Ser Thr
                565                 570                 575

Pro Glu Ile Ser Glu Arg Pro Ala Gly Glu Cys Pro Ala Gly Gly Gly
            580                 585                 590

Ala Ala Glu Asn Ser Ser Leu Gly Gln Glu Gln Pro Glu Ala Pro Ser
        595                 600                 605

Arg Ser Trp Gly Lys Leu Leu Trp Ser Trp Phe Cys Gly Leu Ser Gly
610                 615                 620

Thr Pro Glu Gln Ala Leu Ser Pro Ala Glu Lys Ala Ala Leu Glu Gln
625                 630                 635                 640

Lys Leu Thr Ser Ile Glu Glu Pro Leu Trp Arg His Val Cys Asn
                645                 650                 655

Ile Asn Ala Val Leu Leu Leu Ala Ile Asn Ile Phe Leu Trp Gly Tyr
            660                 665                 670

Phe Ala
    674

<210> SEQ ID NO 42
<211> LENGTH: 2022
<212> TYPE: DNA
<213> ORGANISM: Human

<400> SEQUENCE: 42
atggggcctg agcttcagg  ggacggggtc aggactgaga cagctccaca catagcactg    60
gactccagag ttggtctgca cgcctacgac atcagcgtgg tggtcatcta ctttgtcttc   120
gtcattgctg tggggatctg gtcgtccatc cgtgcaagtc gagggaccat tggcggctat   180
ttcctggccg ggaggtccat gagctggtgg ccaattggag catctctgat gtccagcaat   240
gtgggcagtg gcttgttcat cggcctggct gggacagggg ctgccggagg ccttgccgta   300
ggtggcttcg agtggaacgc aacctggctg ctcctggccc ttggctgggt cttcgtccct   360
gtgtacatcg cagcaggtgt ggtcacaatg ccgcagtatc tgaagaagcg atttggggc    420 cagaggatcc aggtgtacat gtctgtcctg tctctcatcc tctacatctt caccaagatc   480
tcgactgaca tcttctctgg agccctcttc atccagatgg cattgggctg aacctgtac    540 ctctccacag ggatcctgct ggtggtgact gccgtctaca ccattgcagg tggcctcatg   600
gccgtgatct acacagatgc tctgcagacg gtgatcatgg taggggggagc cctggtcctc   660 atgtttctgg gctttcagga cgtgggctgg tacccaggcc tggagcagcg gtacaggcag   720
gccatcccta atgtcacagt ccccaacacc acctgtcacc tccacggcc  cgatgctttc   780 cacattcttc gggaccctgt gagcggggac atcccttggc caggtctcat tttcgggctc   840
acagtgctgg ccacctggtg ttggtgcaca gaccaggtca ttgtgcagcg gtctctctcg   900
gccaagagtc tgtctcatgc caagggaggc tccgtgctgg ggggctacct gaagatcctc   960
cccatgttct tcatcgtcat gcctggcatg atcagccggg ccctgttccc agacgaggtg  1020
ggctgcgtgg accctgatgt ctgccaaaga atctgtgggg cccgagtggg atgttccaac  1080
attgcctacc ctaagttggt catggccctc atgcctgttg gtctgcgggg gctgatgatt  1140
```

-continued

```
gccgtgatca tggccgctct catgagctca ctcacctcca tcttcaacag cagcagcacc   1200
ctgttcacca ttgatgtgtg gcagcgcttc cgcaggaagt caacagagca ggagctgatg   1260
gtggtgggca gagtgtttgt ggtgttcctg gttgtcatca gcatcctctg gatccccatc   1320
atccaaagct ccaacagtgg gcagctcttc gactacatcc aggctgtcac cagttacctg   1380
gccccaccca tcaccgctct cttcctgctg ccatcttct gcaagagggt cacagagccc    1440
ggagctttct ggggcctcgt gtttggcctg ggagtggggc ttctgcgtat gatcctggag   1500
ttctcatacc cagcgccagc ctgtggggag gtggaccgga ggccagcagt gctgaaggac   1560
ttccactacc tgtactttgc aatcctcctc tgcgggctca ctgccatcgt cattgtcatt   1620
gtcagcctct gtacaactcc catccctgag aacagctca cacgcctcac atggtggact    1680
cggaactgcc ccctctctga gctggagaag gaggcccacg agcacacc ggagatatcc     1740
gagaggccag ccggggagtg ccctgcagga ggtggagcgg cagagaactc gagcctgggc   1800
caggagcagc ctgaagcccc aagcaggtcc tggggaaagt tgctctggag ctggttctgt   1860
gggctctctg gaacaccgga gcaggccctg agcccagcag agaaggctgc gctagaacag   1920
aagctgacaa gcattgagga ggagccactc tggagacatg tctgcaacat caatgctgtc   1980
cttttgctgg ccatcaacat cttcctctgg ggctattttg cg                      2022
```

<210> SEQ ID NO 43
<211> LENGTH: 674
<212> TYPE: PRT
<213> ORGANISM: Human

<400> SEQUENCE: 43

```
Met Gly Pro Gly Ala Ser Gly Asp Gly Val Arg Thr Glu Thr Ala Pro
1               5                   10                  15

His Ile Ala Leu Asp Ser Arg Val Gly Leu His Ala Tyr Asp Ile Ser
                20                  25                  30

Val Val Val Ile Tyr Phe Val Phe Val Ile Ala Val Gly Ile Trp Ser
            35                  40                  45

Ser Ile Arg Ala Ser Arg Gly Thr Ile Gly Gly Tyr Phe Leu Ala Gly
        50                  55                  60

Arg Ser Met Ser Trp Trp Pro Ile Gly Ala Ser Leu Met Ser Ser Asn
65                  70                  75                  80

Val Gly Ser Gly Leu Phe Ile Gly Leu Ala Gly Thr Gly Ala Ala Gly
                85                  90                  95

Gly Leu Ala Val Gly Gly Phe Glu Trp Asn Ala Thr Trp Leu Leu Leu
            100                 105                 110

Ala Leu Gly Trp Val Phe Val Pro Val Tyr Ile Ala Ala Gly Val Val
        115                 120                 125

Thr Met Pro Gln Tyr Leu Lys Lys Arg Phe Gly Gly Gln Arg Ile Gln
130                 135                 140

Val Tyr Met Ser Val Leu Ser Leu Ile Leu Tyr Ile Phe Thr Lys Ile
145                 150                 155                 160

Ser Thr Asp Ile Phe Ser Gly Ala Leu Phe Ile Gln Met Ala Leu Gly
                165                 170                 175

Trp Asn Leu Tyr Leu Ser Thr Gly Ile Leu Leu Val Val Thr Ala Val
            180                 185                 190

Tyr Thr Ile Ala Gly Gly Leu Met Ala Val Ile Tyr Thr Asp Ala Leu
        195                 200                 205

Gln Thr Val Ile Met Val Gly Gly Ala Leu Val Leu Met Phe Leu Gly
210                 215                 220
```

```
Phe Gln Asp Val Gly Trp Tyr Pro Gly Leu Glu Gln Arg Tyr Arg Gln
225                 230                 235                 240

Ala Ile Pro Asn Val Thr Val Pro Asn Thr Thr Cys His Leu Pro Arg
            245                 250                 255

Pro Asp Ala Phe His Ile Leu Arg Asp Pro Val Ser Gly Asp Ile Pro
        260                 265                 270

Trp Pro Gly Leu Ile Phe Gly Leu Thr Val Leu Ala Thr Trp Cys Trp
    275                 280                 285

Cys Thr Asp Gln Val Ile Val Gln Arg Ser Leu Ser Ala Lys Ser Leu
290                 295                 300

Ser His Ala Lys Gly Gly Ser Val Leu Gly Gly Tyr Leu Lys Ile Leu
305                 310                 315                 320

Pro Met Phe Phe Ile Val Met Pro Gly Met Ile Ser Arg Ala Leu Phe
                325                 330                 335

Pro Asp Glu Val Gly Cys Val Asp Pro Asp Val Cys Gln Arg Ile Cys
            340                 345                 350

Gly Ala Arg Val Gly Cys Ser Asn Ile Ala Tyr Pro Lys Leu Val Met
        355                 360                 365

Ala Leu Met Pro Val Gly Leu Arg Gly Leu Met Ile Ala Val Ile Met
370                 375                 380

Ala Ala Leu Met Ser Ser Leu Thr Ser Ile Phe Asn Ser Ser Ser Thr
385                 390                 395                 400

Leu Phe Thr Ile Asp Val Trp Gln Arg Phe Arg Arg Lys Ser Thr Glu
                405                 410                 415

Gln Glu Leu Met Val Val Gly Arg Val Phe Val Phe Leu Val Val
            420                 425                 430

Ile Ser Ile Leu Trp Ile Pro Ile Ile Gln Ser Ser Asn Ser Gly Gln
        435                 440                 445

Leu Phe Asp Tyr Ile Gln Ala Val Thr Ser Tyr Leu Ala Pro Pro Ile
    450                 455                 460

Thr Ala Leu Phe Leu Leu Ala Ile Phe Cys Lys Arg Val Thr Glu Pro
465                 470                 475                 480

Gly Ala Phe Trp Gly Leu Val Phe Gly Leu Val Gly Leu Leu Arg
                485                 490                 495

Met Ile Leu Glu Phe Ser Tyr Pro Ala Pro Ala Cys Gly Glu Val Asp
            500                 505                 510

Arg Arg Pro Ala Val Leu Lys Asp Phe His Tyr Leu Tyr Phe Ala Ile
        515                 520                 525

Leu Leu Cys Gly Leu Thr Ala Ile Val Ile Val Ile Val Ser Leu Cys
530                 535                 540

Thr Thr Pro Ile Pro Glu Glu Gln Leu Thr Arg Leu Thr Trp Trp Thr
545                 550                 555                 560

Arg Asn Cys Pro Leu Ser Glu Leu Glu Lys Glu Ala His Glu Ser Thr
                565                 570                 575

Pro Glu Ile Ser Glu Arg Pro Ala Gly Glu Cys Pro Ala Gly Gly Gly
            580                 585                 590

Ala Ala Glu Asn Ser Ser Leu Gly Gln Glu Gln Pro Glu Ala Pro Ser
        595                 600                 605

Arg Ser Trp Gly Lys Leu Leu Trp Ser Trp Phe Cys Gly Leu Ser Gly
    610                 615                 620

Thr Pro Glu Gln Ala Leu Ser Pro Ala Glu Lys Ala Ala Leu Glu Gln
625                 630                 635                 640
```

| Lys | Leu | Thr | Ser | Ile | Glu | Glu | Glu | Pro | Leu | Trp | Arg | His | Val | Cys | Asn |
|---|---|---|---|---|---|---|---|---|---|---|---|---|---|---|---|
| | | | | 645 | | | | 650 | | | | | 655 | | |

| Ile | Asn | Ala | Val | Leu | Leu | Leu | Ala | Ile | Asn | Ile | Phe | Leu | Trp | Gly | Tyr |
|---|---|---|---|---|---|---|---|---|---|---|---|---|---|---|---|
| | | | 660 | | | | 665 | | | | | 670 | | | |

| Phe | Ala |
|---|---|
| | 674 |

<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44

| ggactagtct acccggctgg cctctcggat | 30 |
|---|---|

<210> SEQ ID NO 45
<211> LENGTH: 1755
<212> TYPE: DNA
<213> ORGANISM: Human

<400> SEQUENCE: 45

| atggggcctg gagcttcagg ggacggggtc aggactgaga cagctccaca catagcactg | 60 |
|---|---|
| gactccagag ttggtctgca cgcctacgac atcagcgtgg tggtcatcta ctttgtcttc | 120 |
| gtcattgctg tggggatctg gtcgtccatc cgtgcaagtc gagggaccat tggcggctat | 180 |
| ttcctggccg ggaggtccat gagctggtgg ccaattggag catctctgat gtccagcaat | 240 |
| gtgggcagtg gcttgttcat cggcctggct gggacagggg ctgccggagg ccttgccgta | 300 |
| ggtggcttcg agtggaacgc aacctggctg ctcctggccc ttggctgggt cttcgtccct | 360 |
| gtgtacatcg cagcaggtgt ggtcacaatg ccgcagtatc tgaagaagcg atttgggggc | 420 |
| cagaggatcc aggtgtacat gtctgtcctg tctctcatcc tctacatctt caccaagatc | 480 |
| tcgactgaca tcttctctgg agccctcttc atccagatgg cattgggctg aacctgtac | 540 |
| ctctccacag ggatcctgct ggtggtgact gccgtctaca ccattgcagg tggcctcatg | 600 |
| gccgtgatct acacagatgc tctgcagacg gtgatcatgg taggggagc cctggtcctc | 660 |
| atgtttctgg gctttcagga cgtgggctgg tacccaggcc tggagcagcg gtacaggcag | 720 |
| gccatcccta atgtcacagt ccccaacacc acctgtcacc tcccacggcc cgatgctttc | 780 |
| cacatgcttc gggaccctgt gagcggggac atcccttggc caggtctcat tttcgggctc | 840 |
| acagtgctgg ccacctggtg ttggtgcaca gaccaggtca ttgtgcagcg gtctctctcg | 900 |
| gccaagagtc tgtctcatgc caagggaggc tccgtgctgg ggggctacct gaagatcctc | 960 |
| cccatgttct tcatcgtcat gcctggcatg atcagccggg ccctgttccc agacgaggtg | 1020 |
| ggctgcgtgg accctgatgt ctgccaaaga atctgtgggg cccgagtggg atgttccaac | 1080 |
| attgcctacc ctaagttggt catggccctc atgcctgttg gtctgcgggg ctgatgatt | 1140 |
| gccgtgatca tggccgctct catgagctca ctcacctcca tcttcaacag cagcagcacc | 1200 |
| ctgttcacca ttgatgtgtg gcagcgcttc cgcaggaagt caacgagca ggagctgatg | 1260 |
| gtggtgggca gagtgtttgt ggtgttcctg gttgtcatca gcatcctctg gatccccatc | 1320 |
| atccaaagct ccaacagtgg gcagctcttc gactacatcc aggctgtcac cagttacctg | 1380 |
| gcccacccca tcaccgctct cttcctgctg gccatcttct gcaagagggt cacagagccc | 1440 |
| ggagctttct ggggcctcgt gtttggcctg ggagtggggc ttctgcgtat gatcctggag | 1500 |

-continued

```
ttctcatacc cagcgccagc ctgtggggag gtggaccgga ggccagcagt gctgaaggac    1560
ttccactacc tgtactttgc aatcctcctc tgcgggctca ctgccatcgt cattgtcatt    1620
gtcagcctct gtacaactcc catccctgag aacagctca cacgcctcac atggtggact    1680
cggaactgcc ccctctctga gctggagaag gaggcccacg agagcacacc ggagatatcc    1740
gagaggccag ccggg                                                     1755
```

<210> SEQ ID NO 46
<211> LENGTH: 585
<212> TYPE: PRT
<213> ORGANISM: Human

<400> SEQUENCE: 46

```
Met Gly Pro Gly Ala Ser Gly Asp Gly Val Arg Thr Glu Thr Ala Pro
1               5                   10                  15

His Ile Ala Leu Asp Ser Arg Val Gly Leu His Ala Tyr Asp Ile Ser
            20                  25                  30

Val Val Val Ile Tyr Phe Val Phe Val Ile Ala Val Gly Ile Trp Ser
        35                  40                  45

Ser Ile Arg Ala Ser Arg Gly Thr Ile Gly Gly Tyr Phe Leu Ala Gly
    50                  55                  60

Arg Ser Met Ser Trp Trp Pro Ile Gly Ala Ser Leu Met Ser Ser Asn
65                  70                  75                  80

Val Gly Ser Gly Leu Phe Ile Gly Leu Ala Gly Thr Gly Ala Ala Gly
                85                  90                  95

Gly Leu Ala Val Gly Gly Phe Glu Trp Asn Ala Thr Trp Leu Leu Leu
            100                 105                 110

Ala Leu Gly Trp Val Phe Val Pro Val Tyr Ile Ala Ala Gly Val Val
        115                 120                 125

Thr Met Pro Gln Tyr Leu Lys Lys Arg Phe Gly Gly Gln Arg Ile Gln
130                 135                 140

Val Tyr Met Ser Val Leu Ser Leu Ile Leu Tyr Ile Phe Thr Lys Ile
145                 150                 155                 160

Ser Thr Asp Ile Phe Ser Gly Ala Leu Phe Ile Gln Met Ala Leu Gly
                165                 170                 175

Trp Asn Leu Tyr Leu Ser Thr Gly Ile Leu Leu Val Val Thr Ala Val
            180                 185                 190

Tyr Thr Ile Ala Gly Gly Leu Met Ala Val Ile Tyr Thr Asp Ala Leu
        195                 200                 205

Gln Thr Val Ile Met Val Gly Gly Ala Leu Val Leu Met Phe Leu Gly
    210                 215                 220

Phe Gln Asp Val Gly Trp Tyr Pro Gly Leu Glu Gln Arg Tyr Arg Gln
225                 230                 235                 240

Ala Ile Pro Asn Val Thr Val Pro Asn Thr Thr Cys His Leu Pro Arg
                245                 250                 255

Pro Asp Ala Phe His Met Leu Arg Asp Pro Val Ser Gly Asp Ile Pro
            260                 265                 270

Trp Pro Gly Leu Ile Phe Gly Leu Thr Val Leu Ala Thr Trp Cys Trp
        275                 280                 285

Cys Thr Asp Gln Val Ile Val Gln Arg Ser Leu Ser Ala Lys Ser Leu
    290                 295                 300

Ser His Ala Lys Gly Gly Ser Val Leu Gly Gly Tyr Leu Lys Ile Leu
305                 310                 315                 320

Pro Met Phe Phe Ile Val Met Pro Gly Met Ile Ser Arg Ala Leu Phe
```

```
                     325                 330                 335
Pro Asp Glu Val Gly Cys Val Asp Pro Asp Val Cys Gln Arg Ile Cys
                340                 345                 350
Gly Ala Arg Val Gly Cys Ser Asn Ile Ala Tyr Pro Lys Leu Val Met
            355                 360                 365
Ala Leu Met Pro Val Gly Leu Arg Gly Leu Met Ile Ala Val Ile Met
        370                 375                 380
Ala Ala Leu Met Ser Ser Leu Thr Ser Ile Phe Asn Ser Ser Ser Thr
385                 390                 395                 400
Leu Phe Thr Ile Asp Val Trp Gln Arg Phe Arg Arg Lys Ser Thr Glu
                405                 410                 415
Gln Glu Leu Met Val Val Gly Arg Val Phe Val Val Phe Leu Val Val
                420                 425                 430
Ile Ser Ile Leu Trp Ile Pro Ile Ile Gln Ser Ser Asn Ser Gly Gln
            435                 440                 445
Leu Phe Asp Tyr Ile Gln Ala Val Thr Ser Tyr Leu Ala Pro Pro Ile
        450                 455                 460
Thr Ala Leu Phe Leu Leu Ala Ile Phe Cys Lys Arg Val Thr Glu Pro
465                 470                 475                 480
Gly Ala Phe Trp Gly Leu Val Phe Gly Leu Gly Val Gly Leu Leu Arg
                485                 490                 495
Met Ile Leu Glu Phe Ser Tyr Pro Ala Pro Ala Cys Gly Glu Val Asp
                500                 505                 510
Arg Arg Pro Ala Val Leu Lys Asp Phe His Tyr Leu Tyr Phe Ala Ile
            515                 520                 525
Leu Leu Cys Gly Leu Thr Ala Ile Val Ile Val Ser Leu Cys
        530                 535                 540
Thr Thr Pro Ile Pro Glu Glu Gln Leu Thr Arg Leu Thr Trp Trp Thr
545                 550                 555                 560
Arg Asn Cys Pro Leu Ser Glu Leu Glu Lys Glu Ala His Glu Ser Thr
                565                 570                 575
Pro Glu Ile Ser Glu Arg Pro Ala Gly
            580                 585

<210> SEQ ID NO 47
<211> LENGTH: 26
<212> TYPE: DNA
<213> ORGANISM: Artificial Sequence
<220> FEATURE:
<223> OTHER INFORMATION: Primer

<400> SEQUENCE: 47
gtctttgtgc ctcagtggca acttcc                                       26

<210> SEQ ID NO 48
<211> LENGTH: 26
<212> TYPE: DNA
<213> ORGANISM: Artificial Sequence
<220> FEATURE:
<223> OTHER INFORMATION: Primer

<400> SEQUENCE: 48
tgctgccagc tccttgctca tctgtt                                       26

<210> SEQ ID NO 49
<211> LENGTH: 29
<212> TYPE: DNA
<213> ORGANISM: Artificial Sequence
```

```
<220> FEATURE:
<223> OTHER INFORMATION: Primer

<400> SEQUENCE: 49
tgaggtacct gggaagacag agcatgcag                                          29

<210> SEQ ID NO 50
<211> LENGTH: 30
<212> TYPE: DNA
<213> ORGANISM: Artificial Sequence
<220> FEATURE:
<223> OTHER INFORMATION: Primer

<400> SEQUENCE: 50
tgcctcgagc tccttgctca tctgttagtg                                         30

<210> SEQ ID NO 51
<211> LENGTH: 2254
<212> TYPE: DNA
<213> ORGANISM: Human

<400> SEQUENCE: 51
tgggaagaca gagcatgcag gcagcagaac actgtcctag tccatcccta ctgctacagc        60
aaaacaccta agaccaggta atttataaag tacaggaatt tatttctcac aattctggag       120
gctggaagtc caagatcaaa gccccagcag gtttggtgtc tggtgagggc ccagtctatg       180
cctccaagac ggcaccttgt ggctgtgtcc tcacatggca gaaggtaaaa aggcaaaagg       240
gcctggctag ttcccttagc cctttttataa ggtactgatc ccacccatga gggagaagcc      300
ctcacgggct aatcactcct aaaggcccta cctcttagta ctgttgcatt ggggattcag       360
tttcaacatg aattttggaa gcaacacaag catccaaact atagcaaacc caagggctg        420 ggtgaggggg ctccttgtgg ggagcataga agaagtaca agactcagct gtcttctccc        480
tgcacattcc ttttcccatc tctggaagag tcatccggat ccagagccct cactatggtg       540
tgctcagagg cctaagctca gaccactcct tccctgctcc ctgattaaca cccagagatc       600
tgccagcctc attccccact gtccctgtat ccagctcacc cccagggacc actgggcacc       660
tggtccatca cattttcctg atgtttctaa tgctgcccct cctgcatccc tgttcgtctg       720
ataaacttgc ctttaaacgt gtatatgaag gactcttcct ctggtatcta atcctaacag       780
gtgctagatc ccacagagcc ctgtccagct ggggactatg ctgacctctc tcccagatca       840
atatccctct cctcggggct cagcctggcc agtgcctgat gttctgggat aggagaactg       900
gggagagaag gcctaggacc ctgcctctca cttttctttc caccaaaagg ggaaaaaga        960 ggatctggtc ctcacaccca gccttgggat acttataaga tgctggggat agggtgtggg      1020
acagggccag tgagagctgg ggatgggtg tgggacaggg ccagtgagat ctgttttcct       1080
gctgctccag tctgggccct acagcagatg catgcagagt aatatttgta agactgaaat      1140
attccaaatg cagctacttt ggaaggacca tgtgagcaga tatctaagtg cgtggcatct      1200 gggcccttg gctagatggt ggtcgatgtt ggtttctttg tgttaacccc aagaacattc       1260
agtagctcag ggtttgcaga ggttctcagg agcacatctt agcctcattg gtggtgtgag      1320
gcaggcaggg cacaggtcac actgatgagg acacccgggc ccagagacat ttagcaacct      1380
gcccaagggc atctgtagtt cagtgagagg tggagctggg actgaaatct aggctgcctg      1440
agtcccagag atggtcttcc ctggacccag ggagcactgt atcttttca gggaaggcct       1500 cctgaccaca accatttcat ctgtcacagt acagaatagg aagtatgggt caggcatcag      1560
```

| | |
|---|---|
| aagatgtgaa ttctggctct gccttttcag agatggccct gcctagttcc ttggaataaa | 1620 |
| tgatgatgtc ttccccagcc tcagtttcct acactatata aaagagaaa gcaacatcta | 1680 |
| ggtaggttgg aatgggagta catgaggtgg tggccacttt gctagggtca cagtagactc | 1740 |
| ctcacctcct tcccttgtc ttcctctcac taggtaaaag acaattgtat tgaactctta | 1800 |
| agaaaattgg actccagtcc cggctccacc tttacttccc tgggccttgg ttttcccacc | 1860 |
| acacaggagt ttgaacactt tgatttctga agtccttccc acctctgggg ttccaatatt | 1920 |
| ctgctccttt tctcctcttc ctcctccccc tcctttctcc tcctgctcat ctggggttag | 1980 |
| ggagattgcg tgtatgtgtg tgcctgtgtg tacacatgca tgtatgtgtg tgcacgtagt | 2040 |
| ggcagcaagg aagaggaagg aaggagtcct gcaggggttg gtggtggcag ttgggagaaa | 2100 |
| aggaggcagg actgtatgtg ccagcagggc tcagagtttt ctcaccaact aatggtgctt | 2160 |
| ggggcagttt aatcattaaa ggaaaggaat gaagccagga gcgcctcaaa gtccagcctg | 2220 |
| ctgttgacca acactaacag atgagcaagg agct | 2254 |

<210> SEQ ID NO 52
<211> LENGTH: 25
<212> TYPE: DNA
<213> ORGANISM: Artificial Sequence
<220> FEATURE:
<223> OTHER INFORMATION: Primer

<400> SEQUENCE: 52

| | |
|---|---|
| tctaatgctg cctctcctgc atccc | 25 |

<210> SEQ ID NO 53
<211> LENGTH: 25
<212> TYPE: DNA
<213> ORGANISM: Artificial Sequence
<220> FEATURE:
<223> OTHER INFORMATION: Primer

<400> SEQUENCE: 53

| | |
|---|---|
| gggactatgc tgtcctctct cccag | 25 |

<210> SEQ ID NO 54
<211> LENGTH: 2254
<212> TYPE: DNA
<213> ORGANISM: Human

<400> SEQUENCE: 54

| | |
|---|---|
| tgggaagaca gagcatgcag gcagcagaac actgtcctag tccatcccta ctgctacagc | 60 |
| aaaacaccta agaccaggta atttataaag tacaggaatt tatttctcac aattctggag | 120 |
| gctggaagtc caagatcaaa gccccagcag gtttggtgtc tggtgagggc ccagtctatg | 180 |
| cctccaagac ggcaccttgt ggctgtgtcc tcacatggca gaaggtaaaa aggcaaaagg | 240 |
| gcctggctag ttcccttagc ccttttataa ggtactgatc ccacccatga gggagaagcc | 300 |
| ctcacgggct aatcactcct aaaggcccta cctcttagta ctgttgcatt ggggattcag | 360 |
| tttcaacatg aattttggaa gcaacacaag catccaaact atagcaaacc caagggctg | 420 |
| ggtgaggggg ctccttgtgg ggagcataga agaagtaca agactcagct gtcttctccc | 480 |
| tgcacattcc ttttcccatc tctggaagag tcatccggat ccagagccct cactatggtg | 540 |
| tgctcagagg cctaagctca gaccactcct tccctgctcc ctgattaaca cccagagatc | 600 |
| tgccagcctc attccccact gtccctgtat ccagctcacc cccagggacc actgggcacc | 660 |
| tggtccatca cattttcctg atgtttctaa tgctgcccct cctgcatccc tgttcgtctg | 720 |

-continued

| | |
|---|---|
| ataaacttgc ctttaaacgt gtatatgaag gactcttcct ctggtatcta atcctaacag | 780 |
| gtgctagatc ccacagagcc ctgtccagct ggggactatg ctgtcctctc tcccagatca | 840 |
| atatccctct cctcggggct cagcctggcc agtgcctgat gttctgggat aggagaactg | 900 |
| gggagagaag gcctaggacc ctgcctctca cttttctttc caccaaaagg ggaaaaaaga | 960 |
| ggatctggtc ctcacaccca gccttgggat acttataaga tgctggggat agggtgtggg | 1020 |
| acagggccag tgagagctgg ggatgggtg tgggacaggg ccagtgagat ctgttttcct | 1080 |
| gctgctccag tctgggccct acagcagatg catgcagagt aatatttgta agactgaaat | 1140 |
| attccaaatg cagctacttt ggaaggacca tgtgagcaga tatctaagtg cgtggcatct | 1200 |
| gggcccttg gctagatggt ggtcgatgtt ggtttctttg tgttaacccc aagaacattc | 1260 |
| agtagctcag ggtttgcaga ggttctcagg agcacatctt agcctcattg gtggtgtgag | 1320 |
| gcaggcaggg cacaggtcac actgatgagg acacccgggc ccagagacat ttagcaacct | 1380 |
| gcccaagggc atctgtagtt cagtgagagg tggagctggg actgaaatct aggctgcctg | 1440 |
| agtcccagag atggtcttcc ctggacccag ggagcactgt atcttttca gggaaggcct | 1500 |
| cctgaccaca accatttcat ctgtcacagt acagaatagg aagtatgggt caggcatcag | 1560 |
| aagatgtgaa ttctggctct gccttttcag agatggccct gcctagttcc ttggaataaa | 1620 |
| tgatgatgtc ttccccagcc tcagtttcct acactatata aaaagagaaa gcaacatcta | 1680 |
| ggtaggttgg aatgggagta catgaggtgg tggccacttt gctagggtca cagtagactc | 1740 |
| ctcacctcct tccccttgtc ttcctctcac taggtaaaag acaattgtat tgaactctta | 1800 |
| agaaaattgg actccagtcc cggctccacc tttacttccc tgggccttgg ttttcccacc | 1860 |
| acacaggagt ttgaacactt tgatttctga agtccttccc acctctgggg ttccaatatt | 1920 |
| ctgctccttt tctcctcttc ctcctccccc tcctttctcc tcctgctcat ctggggttag | 1980 |
| ggagattgcg tgtatgtgtg tgcctgtgtg tacacatgca tgtatgtgtg tgcacgtagt | 2040 |
| ggcagcaagg aagaggaagg aaggagtcct gcaggggttg gtggtggcag ttgggagaaa | 2100 |
| aggaggcagg actgtatgtg ccagcagggc tcagagtttt ctcaccaact aatggtgctt | 2160 |
| ggggcagttt aatcattaaa ggaaaggaat gaagccagga gcgcctcaaa gtccagcctg | 2220 |
| ctgttgacca acactaacag atgagcaagg agct | 2254 |

<210> SEQ ID NO 55
<211> LENGTH: 2254
<212> TYPE: DNA
<213> ORGANISM: Human

<400> SEQUENCE: 55

| | |
|---|---|
| tgggaagaca gagcatgcag gcagcagaac actgtcctag tccatcccta ctgctacagc | 60 |
| aaaacaccta agaccaggta atttataaag tacaggaatt tatttctcac aattctggag | 120 |
| gctggaagtc caagatcaaa gccccagcag gtttggtgtc tggtgagggc ccagtctatg | 180 |
| cctccaagac ggcaccttgt ggctgtgtcc tcacatggca gaaggtaaaa aggcaaaagg | 240 |
| gcctggctag ttcccttagc cctttttataa ggtactgatc ccacccatga gggagaagcc | 300 |
| ctcacgggct aatcactcct aaaggcccta cctcttagta ctgttgcatt ggggattcag | 360 |
| tttcaacatg aattttggaa gcaacacaag catccaaact atagcaaacc caagggctg | 420 |
| ggtgaggggg ctccttgtgg ggagcataga agaagtaca agactcagct gtcttctccc | 480 |
| tgcacattcc ttttcccatc tctggaagag tcatccggat ccagagccct cactatggtg | 540 |

-continued

| | |
|---|---|
| tgctcagagg cctaagctca gaccactcct tccctgctcc ctgattaaca cccagagatc | 600 |
| tgccagcctc attccccact gtccctgtat ccagctcacc cccagggacc actgggcacc | 660 |
| tggtccatca cattttcctg atgtttctaa tgctgcctct cctgcatccc tgttcgtctg | 720 |
| ataaacttgc ctttaaacgt gtatatgaag gactcttcct ctggtatcta atcctaacag | 780 |
| gtgctagatc ccacagagcc ctgtccagct ggggactatg ctgacctctc tcccagatca | 840 |
| atatccctct cctcggggct cagcctgcc agtgcctgat gttctgggat aggagaactg | 900 |
| gggagagaag gcctaggacc ctgcctctca ctttcttc caccaaaagg ggaaaaaga | 960 |
| ggatctggtc ctcacaccca gccttgggat acttataaga tgctggggat agggtgtggg | 1020 |
| acagggccag tgagagctgg ggatggggtg tgggacaggg ccagtgagat ctgttttcct | 1080 |
| gctgctccag tctgggccct acagcagatg catgcagagt aatatttgta agactgaaat | 1140 |
| attccaaatg cagctacttt ggaaggacca tgtgagcaga tatctaagtg cgtggcatct | 1200 |
| gggccccttg gctagatggt ggtcgatgtt ggttctttg tgttaacccc aagaacattc | 1260 |
| agtagctcag ggtttgcaga ggttctcagg agcacatctt agcctcattg gtggtgtgag | 1320 |
| gcaggcaggg cacaggtcac actgatgagg cacccgggc ccagagacat ttagcaacct | 1380 |
| gcccaagggc atctgtagtt cagtgagagg tggagctggg actgaaatct aggctgcctg | 1440 |
| agtcccagag atggtcttcc ctggacccag ggagcactgt atctttttca ggaaggcct | 1500 |
| cctgaccaca accatttcat ctgtcacagt acagaatagg aagtatgggt caggcatcag | 1560 |
| aagatgtgaa ttctggctct gccttttcag agatggccct gcctagttcc ttggaataaa | 1620 |
| tgatgatgtc ttccccagcc tcagtttcct acactatata aaagagaaa gcaacatcta | 1680 |
| ggtaggttgg aatgggagta catgaggtgg tggccacttt gctagggtca cagtagactc | 1740 |
| ctcacctcct tcccccttgtc ttcctctcac taggtaaaag acaattgtat tgaactctta | 1800 |
| agaaaattgg actccagtcc cggctccacc tttacttccc tgggccttgg ttttcccacc | 1860 |
| acacaggagt ttgaacactt tgatttctga agtccttccc acctctgggg ttccaatatt | 1920 |
| ctgctccttt tctcctcttc ctcctcccc tcctttctcc tcctgctcat ctggggttag | 1980 |
| ggagattgcg tgtatgtgtg tgcctgtgtg tacacatgca tgtatgtgtg tgcacgtagt | 2040 |
| ggcagcaagg aagaggaagg aaggagtcct gcagggtttg gtggtggcag ttgggagaaa | 2100 |
| aggaggcagg actgtatgtg ccagcagggc tcagagtttt ctcaccaact aatggtgctt | 2160 |
| ggggcagttt aatcattaaa ggaaaggaat gaagccagga gcgcctcaaa gtccagcctg | 2220 |
| ctgttgacca acactaacag atgagcaagg agct | 2254 |

<210> SEQ ID NO 56
<211> LENGTH: 2254
<212> TYPE: DNA
<213> ORGANISM: Human

<400> SEQUENCE: 56

| | |
|---|---|
| tgggaagaca gagcatgcag gcagcagaac actgtcctag tccatcccta ctgctacagc | 60 |
| aaaacaccta agaccaggta atttataaag tacaggaatt tatttctcac aattctggag | 120 |
| gctggaagtc caagatcaaa gccccagcag gtttggtgtc tggtgagggc ccagtctatg | 180 |
| cctccaagac ggcaccttgt ggctgtgtcc tcacatggca gaaggtaaaa aggcaaaagg | 240 |
| gcctggctag ttcccttagc cctttaataa ggtactgatc ccacccatga gggagaagcc | 300 |
| ctcacgggct aatcactcct aaaggcccta cctcttagta ctgttgcatt ggggattcag | 360 |
| tttcaacatg aattttggaa gcaacacaag catccaaact atagcaaacc ccaagggctg | 420 |

-continued

| | |
|---|---|
| ggtgaggggg ctccttgtgg ggagcataga aagaagtaca agactcagct gtcttctccc | 480 |
| tgcacattcc tttcccatc tctggaagag tcatccggat ccagagccct cactatggtg | 540 |
| tgctcagagg cctaagctca gaccactcct tccctgctcc ctgattaaca cccagagatc | 600 |
| tgccagcctc attccccact gtccctgtat ccagctcacc cccagggacc actgggcacc | 660 |
| tggtccatca cattttcctg atgtttctaa tgctgcctct cctgcatccc tgttcgtctg | 720 |
| ataaacttgc ctttaaacgt gtatatgaag gactcttcct ctggtatcta atcctaacag | 780 |
| gtgctagatc ccacagagcc ctgtccagct ggggactatg ctgtcctctc tcccagatca | 840 |
| atatccctct cctcggggct cagcctggcc agtgcctgat gttctgggat aggagaactg | 900 |
| gggagagaag gcctaggacc ctgcctctca cttttctttc caccaaaagg ggaaaaaaga | 960 |
| ggatctggtc ctcacaccca gccttgggat acttataaga tgctggggat agggtgtggg | 1020 |
| acagggccag tgagagctgg ggatgggtgt tgggacaggg ccagtgagat ctgttttcct | 1080 |
| gctgctccag tctgggccct acagcagatg catgcagagt aatatttgta agactgaaat | 1140 |
| attccaaatg cagctacttt ggaaggacca tgtgagcaga tatctaagtg cgtggcatct | 1200 |
| gggccccttg gctagatggt ggtcgatgtt ggtttctttg tgttaacccc aagaacattc | 1260 |
| agtagctcag ggtttgcaga ggttctcagg agcacatctt agcctcattg gtggtgtgag | 1320 |
| gcaggcaggg cacaggtcac actgatgagg acacccgggc ccagagacat ttagcaacct | 1380 |
| gcccaagggc atctgtagtt cagtgagagg tggagctggg actgaaatct aggctgcctg | 1440 |
| agtcccagag atggtcttcc ctggacccag ggagcactgt atcttttca gggaaggcct | 1500 |
| cctgaccaca accatttcat ctgtcacagt acagaatagg aagtatgggt caggcatcag | 1560 |
| aagatgtgaa ttctggctct gccttttcag agatggccct gcctagttcc ttggaataaa | 1620 |
| tgatgatgtc ttccccagcc tcagtttcct acactatata aaagagaaa gcaacatcta | 1680 |
| ggtaggttgg aatgggagta catgaggtgg tggccacttt gctagggtca cagtagactc | 1740 |
| ctcacctcct tccccttgtc ttcctctcac taggtaaaag caattgtat tgaactctta | 1800 |
| agaaaattgg actccagtcc cggctccacc tttacttccc tgggccttgg ttttcccacc | 1860 |
| acacaggagt ttgaacactt tgatttctga agtccttccc acctctgggg ttccaatatt | 1920 |
| ctgctccttt tctcctcttc ctcctccccc tcctttctcc tcctgctcat ctggggttag | 1980 |
| ggagattgcg tgtatgtgtg tgcctgtgtg tacacatgca tgtatgtgtg tgcacgtagt | 2040 |
| ggcagcaagg aagaggaagg aaggagtcct gcaggggttg gtggtggcag ttgggagaaa | 2100 |
| aggaggcagg actgtatgtg ccagcagggc tcagagtttt ctcaccaact aatggtgctt | 2160 |
| ggggcagttt aatcattaaa ggaaaggaat gaagccagga gcgcctcaaa gtccagcctg | 2220 |
| ctgttgacca acactaacag atgagcaagg agct | 2254 |

<210> SEQ ID NO 57
<211> LENGTH: 29
<212> TYPE: DNA
<213> ORGANISM: Artificial Sequence
<220> FEATURE:
<223> OTHER INFORMATION: Primer

<400> SEQUENCE: 57
agaggtaccg gtcctcacac ccagccttg        29

<210> SEQ ID NO 58
<211> LENGTH: 29
<212> TYPE: DNA

<213> ORGANISM: Artificial Sequence
<220> FEATURE:
<223> OTHER INFORMATION: Primer

<400> SEQUENCE: 58
attggtaccc agtcccggct gcaccttta                                29

<210> SEQ ID NO 59
<211> LENGTH: 23
<212> TYPE: DNA
<213> ORGANISM: Artificial Sequence
<220> FEATURE:
<223> OTHER INFORMATION: Primer

<400> SEQUENCE: 59
ggactcgagg agtctactgt gac                                     23

<210> SEQ ID NO 60
<211> LENGTH: 23
<212> TYPE: DNA
<213> ORGANISM: Artificial Sequence
<220> FEATURE:
<223> OTHER INFORMATION: Primer

<400> SEQUENCE: 60
ttgtggggag catagaaaga agt                                     23

<210> SEQ ID NO 61
<211> LENGTH: 19
<212> TYPE: DNA
<213> ORGANISM: Artificial Sequence
<220> FEATURE:
<223> OTHER INFORMATION: Primer

<400> SEQUENCE: 61
caaggctggg tgtgaggac                                          19

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
aggcctaagc tcagaccact cc                                      22

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
gatccatcca aggtcacacg                                         20

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
cttcccctca gcaacacgca cat                                     23

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
ggcctcccac agcacagcac t                                             21

<210> SEQ ID NO 66
<211> LENGTH: 21
<212> TYPE: DNA
<213> ORGANISM: Artificial Sequence
<220> FEATURE:
<223> OTHER INFORMATION: Primer

<400> SEQUENCE: 66
ggctgggctt gctgagtgac a                                             21

<210> SEQ ID NO 67
<211> LENGTH: 21
<212> TYPE: DNA
<213> ORGANISM: Artificial Sequence
<220> FEATURE:
<223> OTHER INFORMATION: Primer

<400> SEQUENCE: 67
gcagcgcagg tagaggagag g                                             21

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
gacaggctca gtgggtttc ag                                             22

<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
tagcacaagc ctggggtaga g                                             21

<210> SEQ ID NO 70
<211> LENGTH: 24
<212> TYPE: DNA
<213> ORGANISM: Artificial Sequence
<220> FEATURE:
<223> OTHER INFORMATION: Primer

<400> SEQUENCE: 70
cgtgggaaag gagttagggt gata                                          24

<210> SEQ ID NO 71
<211> LENGTH: 24
<212> TYPE: DNA
<213> ORGANISM: Artificial Sequence
<220> FEATURE:

```
<223> OTHER INFORMATION: Primer

<400> SEQUENCE: 71
tgttctttgt actctttgct tttg                                         24
```